United States Patent
Douglas

(10) Patent No.: US 7,699,883 B2
(45) Date of Patent: Apr. 20, 2010

(54) VASCULAR GRAFT AND DEPLOYMENT SYSTEM

(76) Inventor: Myles Douglas, 605 Skyhawk Ranch Road, Gardenville, NV (US) 89460

( * ) Notice: Subject to any disclaimer, the term of this patent is extended or adjusted under 35 U.S.C. 154(b) by 64 days.

(21) Appl. No.: 11/337,043

(22) Filed: Jan. 19, 2006

(65) Prior Publication Data
US 2006/0178726 A1 Aug. 10, 2006

Related U.S. Application Data

(63) Continuation-in-part of application No. 10/972,936, filed on Oct. 25, 2004, now abandoned.

(51) Int. Cl.
A61F 2/06 (2006.01)
(52) U.S. Cl. ................ 623/1.11; 623/1.35
(58) Field of Classification Search ............ 606/108; 623/1.11, 1.23, 1.27, 1.35, 1.12; 604/526, 604/527

See application file for complete search history.

(56) References Cited

U.S. PATENT DOCUMENTS

| | | | |
|---|---|---|---|
| 5,104,404 A | 4/1992 | Wolff | |
| 5,695,482 A * | 12/1997 | Kaldany | 604/526 |
| 5,782,906 A | 7/1998 | Marshall et al. | |
| 5,904,713 A | 5/1999 | Leschinsky | |
| 5,925,061 A | 7/1999 | Ogi et al. | |
| 5,938,696 A * | 8/1999 | Goicoechea et al. | 606/194 |
| 6,033,394 A * | 3/2000 | Vidlund et al. | 604/524 |
| 6,056,775 A | 5/2000 | Borghi et al. | |
| 6,068,655 A | 5/2000 | Seguin et al. | |
| 6,086,611 A | 7/2000 | Duffy et al. | |
| 6,093,203 A * | 7/2000 | Uflacker | 623/1.12 |
| 6,096,073 A | 8/2000 | Webster et al. | |
| 6,183,509 B1 | 2/2001 | Dibie | |
| 6,197,049 B1 | 3/2001 | Shaolian et al. | |
| 6,258,117 B1 | 7/2001 | Camrud et al. | |
| 6,287,330 B1 | 9/2001 | Johansson et al. | |
| 6,514,281 B1 * | 2/2003 | Blaeser et al. | 623/1.12 |
| 6,520,988 B1 * | 2/2003 | Colombo et al. | 623/1.35 |
| 6,576,007 B2 | 6/2003 | Dehdashtian | |
| 6,673,107 B1 | 1/2004 | Brandt et al. | |
| 6,749,600 B1 * | 6/2004 | Levy | 604/527 |
| 6,908,477 B2 * | 6/2005 | McGuckin et al. | 623/1.11 |
| 6,911,042 B2 | 6/2005 | Weadock | |
| 6,918,925 B2 | 7/2005 | Tehrani | |
| 6,951,572 B1 | 10/2005 | Douglas | |
| 7,118,539 B2 * | 10/2006 | Vrba et al. | 600/585 |
| 7,125,419 B2 | 10/2006 | Sequin et al. | |

(Continued)

*Primary Examiner*—Todd E Manahan
*Assistant Examiner*—Lindsey Bachman
(74) *Attorney, Agent, or Firm*—McDermott Will & Emery LLP

(57) ABSTRACT

A vascular graft includes a main portion and a branch portion that is coupled to the main portion by an articulating joint. The vascular graft may be inserted into the thoracic aorta with the branch portion positioned within a branch vessel and the main portion positioned within the thoracic aorta. The graft may be deployed within a deployment apparatus comprising an outer member and an inner member and a pusher. The main graft portion may be housed within the inner member while the branch graft portion is housed within the space between the inner and outer members. The inner member may have a longitudinal groove for allowing the articulating joint to pass by when the branch graft portion is deployed.

50 Claims, 36 Drawing Sheets

U.S. PATENT DOCUMENTS

| | | |
|---|---|---|
| 2001/0012943 A1 | 8/2001 | Shaolian et al. |
| 2002/0058905 A1 | 5/2002 | Madrid et al. |
| 2002/0120327 A1 | 8/2002 | Cox et al. |
| 2002/0165602 A1 | 11/2002 | Douglas et al. |
| 2002/0198587 A1 | 12/2002 | Greenberg et al. |
| 2003/0125802 A1 | 7/2003 | Callol et al. |
| 2003/0139803 A1 | 7/2003 | Sequin et al. |
| 2005/0149161 A1* | 7/2005 | Eidenschink et al. ....... 623/1.11 |

* cited by examiner

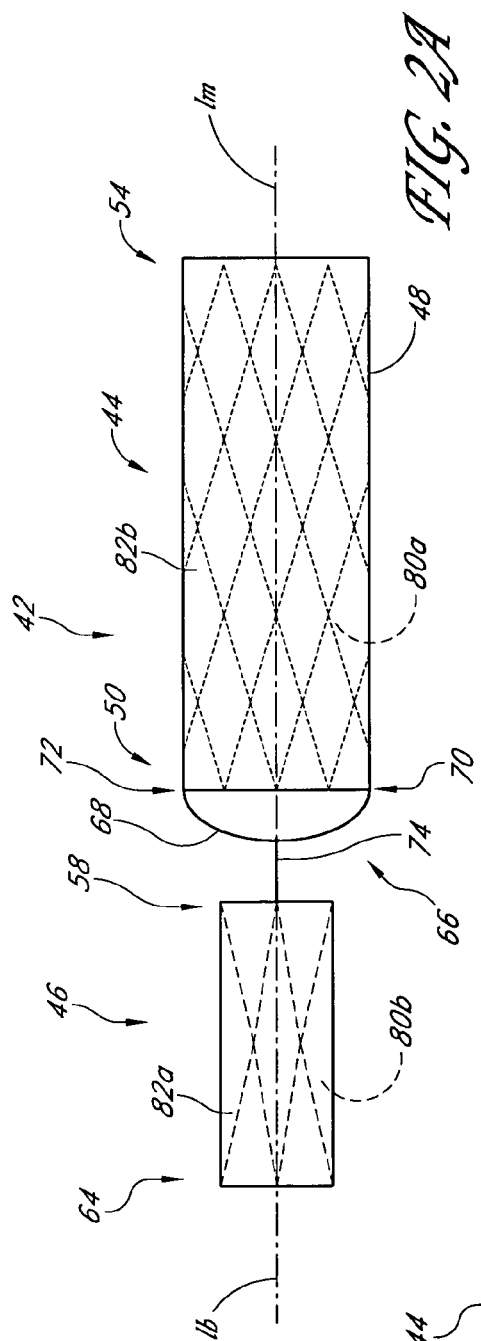
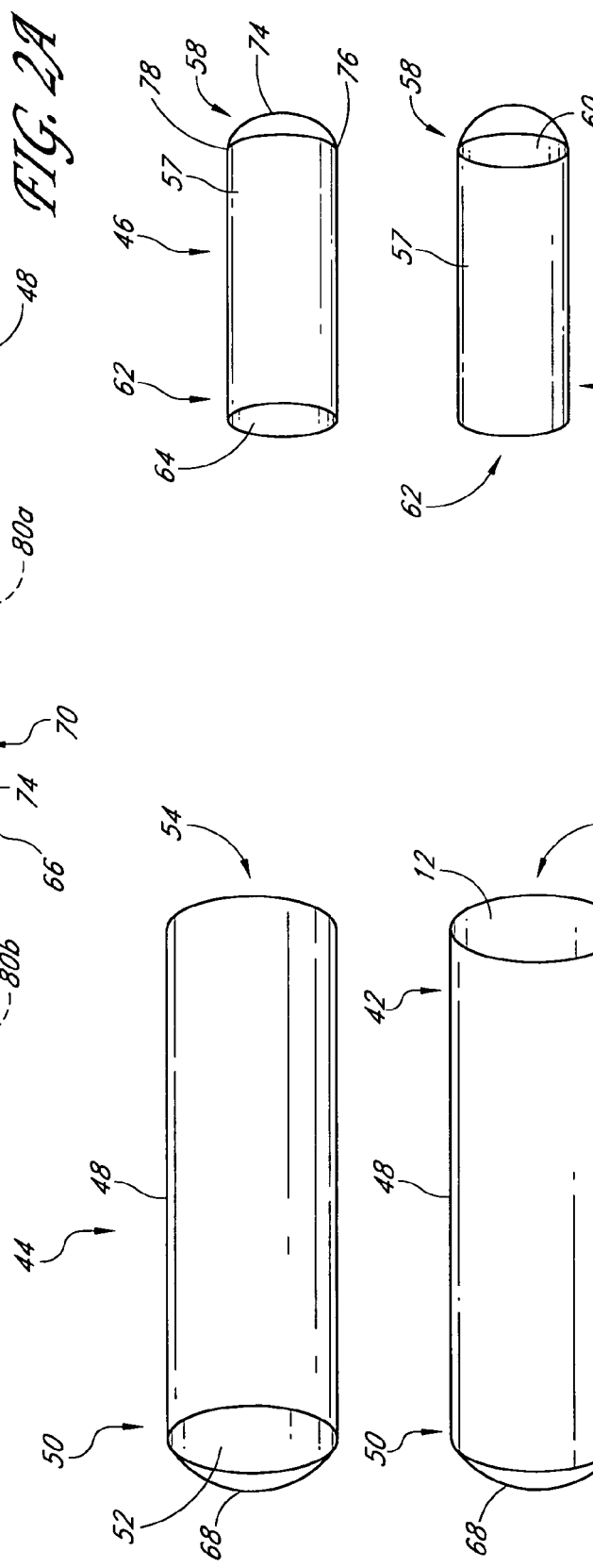

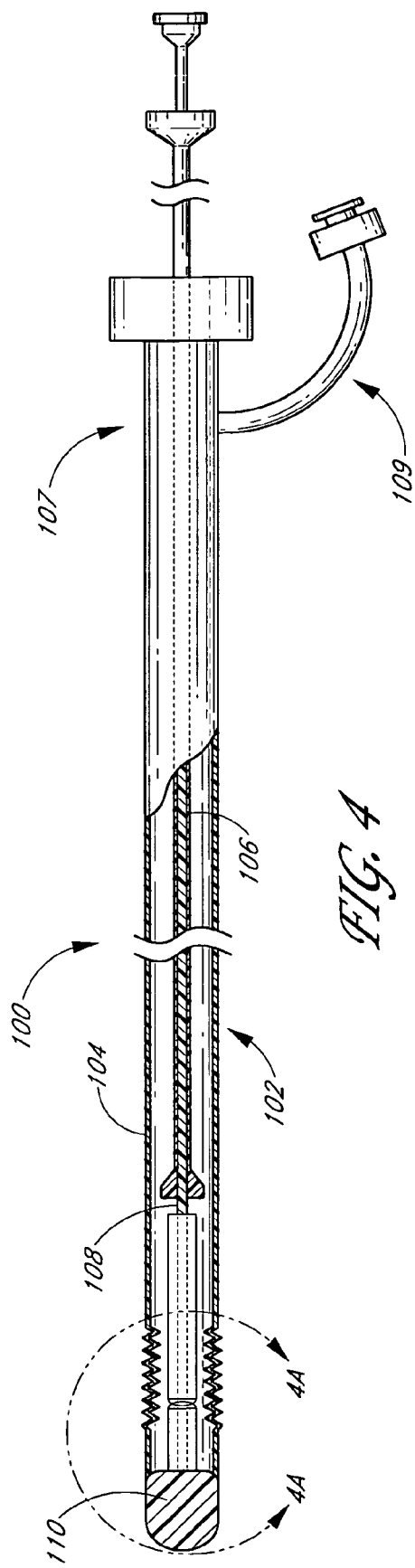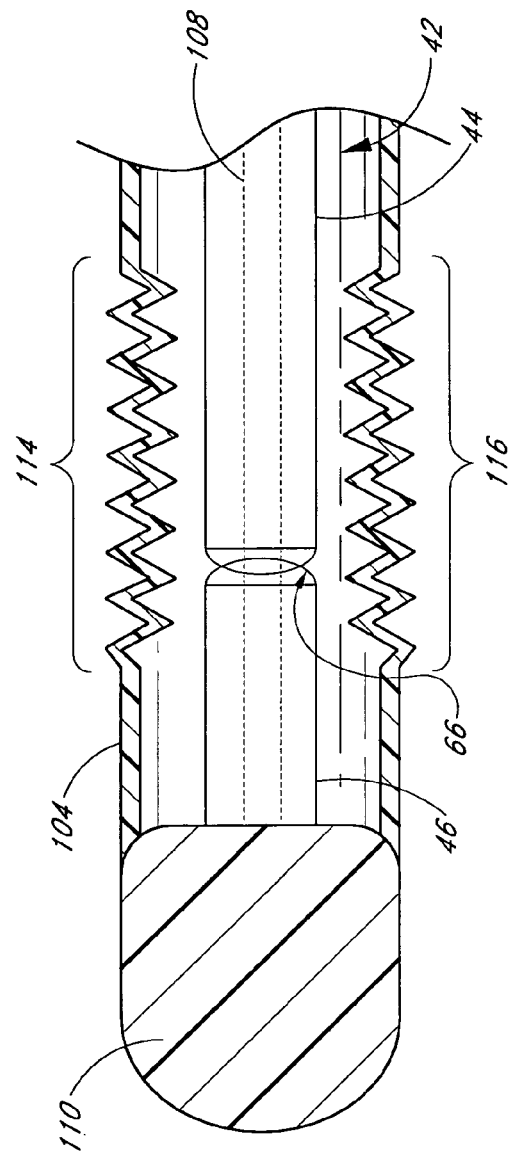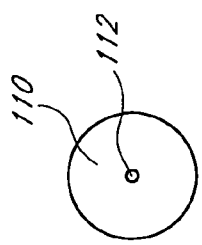

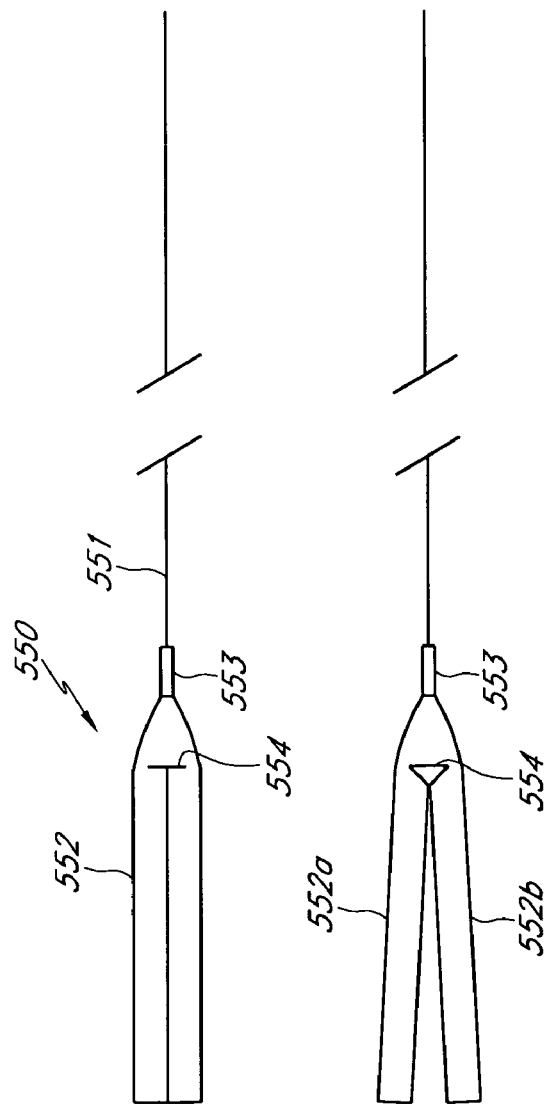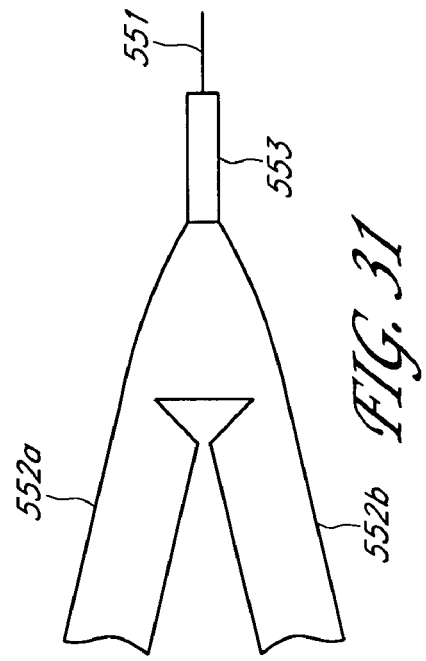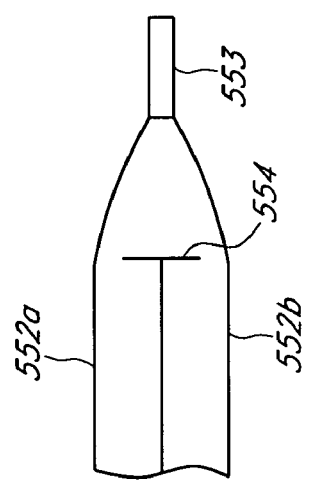
FIG. 29
FIG. 30
FIG. 31
FIG. 32

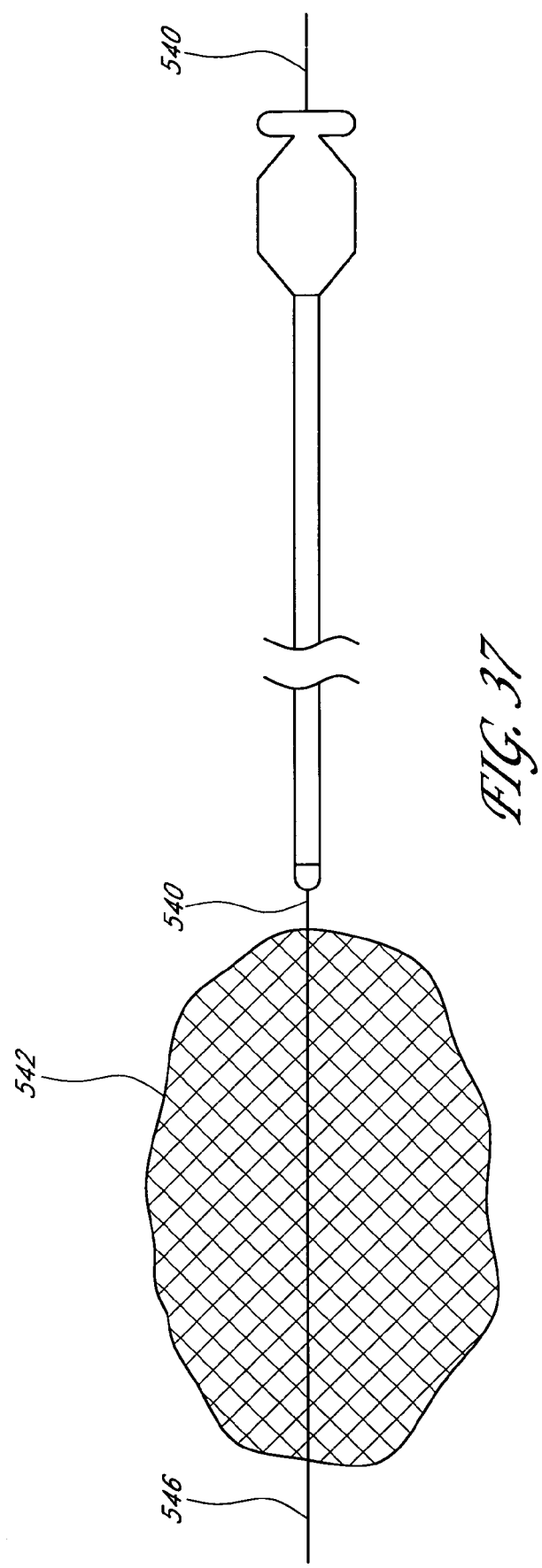

VASCULAR GRAFT AND DEPLOYMENT SYSTEM

PRIORITY INFORMATION

This application is a continuation-in-part of U.S. patent application Ser. No. 10/972,936, filed Oct. 25, 2004, now abandoned, the entire contents of which are hereby incorporated by reference herein.

BACKGROUND OF THE INVENTION

1. Field of the Invention

The present invention relates to medical devices and methods and, more particularly, to vascular grafts and vascular graft deployment systems.

2. Description of the Related Art

The aorta is the largest artery in the body and is responsible for delivering blood from the heart to the organs of the body. The aorta includes the thoracic aorta, which arises from the left ventricle of the heart, passes upward, bends over and passes down towards the thorax, and the abdominal aorta which passes through the thorax and through the abdomen to about the level of the fourth lumbar vertebra, where it divides into the two common iliac arteries. The thoracic aorta is divided into the (i) ascending aorta, which arises from the left ventricle of the heart, (ii) the aorta arch, which arches from the ascending aorta and (iii) the descending aorta which descends from the aorta arch towards the abdominal aortic.

A thoracic aortic aneurysm ("TAA") is a widening, bulge, or ballooning out of a portion of the thoracic aorta, usually at a weak spot in the aortic wall. If left untreated, the aneurysm may progressively expand until the vessel dissects or ruptures. This may lead to severe and even fatal hemorrhaging. Factors leading to thoracic aorta aneurysms include hardening of the arteries (atherosclerosis), hypertension, congenital disorders such as Marfan's syndrome, trauma, or less commonly syphilis. Thoracic aorta aneurysms occur in the ascending aorta about 25% of the time, the aortic arch about 25% of the time and in the descending aorta about 50% of the time.

Treatment of thoracic aorta aneurysms depends upon the location of the aneurysm. For aneurysms in the ascending aorta or aortic arch, surgery is typically required to replace the aorta with an artificial vessel. This surgical procedure typically requires exposure of the aorta and the use of a heart-lung machine. If the aortic arch is involved, a specialized technique called "circulatory arrest" (i.e., a period without blood circulation while on life support) may be necessary. For aneurysms in the descending aorta, the vessel may also be replaced with an artificial vessel through surgery. In some circumstances, an endoluminal vascular graft may be used eliminating the need for open surgery.

As compared to, for example, the abdominal aorta artery, the thoracic aorta is a particularly difficult environment for endovascular grafts. For example, the anatomy and physiology of the thoracic aorta is more complicated than the abdominal aorta. High pulse volumes and challenging pressure dynamics further complicate endovascular procedures. Accordingly, endovascular grafts and surgery are used to treat thoracic aorta aneurysms by only the most experienced and skilled surgeons.

Accordingly, there is a general need for an endovascular graft and deployment systems for treating thoracic aorta aneurysms.

SUMMARY OF THE INVENTION

As such, one embodiment of the present invention comprises a method of treating a thoracic aorta. The method comprises providing a vascular graft comprising a main portion and a branch portion that is coupled to the main portion, the main portion comprising a distal end and a proximal end and a main lumen extending therethrough. A catheter is provided having a distal end and a proximal end. The vascular graft is positioned within the catheter in a first, compressed state such that the branch portion is positioned closer to the distal end of the catheter than the main portion. The distal end of the catheter is advanced up through the descending aorta into a branch vessel of the thoracic aorta. The branch portion of the vascular graft is deployed within the branch vessel and then the main portion of the vascular graft is deployed in the thoracic aorta.

Another embodiment of the present invention comprises a vascular graft having a branch body with a distal end and a proximal end. The graft also includes a main body, having a distal end, proximal end and main lumen extending therethrough. An articulated joint couples the branch body to the main body such that the proximal end of the branch body generally faces the distal end of the main body. The articulated joint is configured to allow angular adjustment of the branch body with respect to the main body generally about a vertex, the vertex being moveable along a first path.

Another embodiment of the present invention comprises the combination of a deployment apparatus and a vascular graft having a main portion and a branch portion that is connected to the main portion by an articulating joint. The combination includes an elongate flexible body having a proximal end, a distal end and a region of increased flexibility located between the distal end and the proximal end. A pusher is moveably positioned within the elongate flexible body. The vascular graft is positioned within the elongated flexible body in a compressed state between the distal end of the elongate flexible body and the pusher, the vascular graft being positioned within the elongate flexible body such that the articulating joint is generally positioned within the area of increased flexibility.

Another embodiment of the present invention comprises a catheter for delivering an endovascular device to the thoracic aorta. The catheter comprises an elongate, flexible body, having a proximal end and a distal end. An endovascular device zone is positioned on the catheter for carrying a deployable endovascular device. A flex point on the catheter is positioned within the endovascular device zone. The flex point has a greater flexibility than the elongate flexible body.

Another embodiment of the present invention comprises a method of treating the thoracic aortic artery. The method comprises deploying an anchor in a branch vessel in communication with the thoracic aorta and deploying an endovascular device within the thoracic aorta. The anchor is flexibly connected to the endovascular device.

Another embodiment of the present invention comprises a method of treating a thoracic aorta, which comprises the ascending aorta, the aorta arch and the descending aorta. The method comprises providing a vascular graft comprising a main portion and a branch portion that is coupled to the main portion, the main portion comprising a distal end and a proximal end and a main lumen extending therethrough, providing a catheter having a distal end and a proximal end, the main portion of the vascular graft being positioned within the catheter in a first, compressed state and providing a removable sheath that is coupled to a pull wire for constraining the branch portion in a compressed state. The distal end of the catheter is advanced up through the descending aorta into the ascending aorta. The constrained branch portion and removable sheath are positioned at least partially within a branch vessel. The main portion of the vascular graft is positioned within the descending aorta by proximally retracting a portion of the deployment catheter. The branch portion of the vascular graft is deployed by proximally withdrawing the pull wire and removing the removable sheath from the branch portion.

Another embodiment of the present invention comprises a combination of a deployment apparatus and a vascular graft having a main portion and a branch portion that is connected to the main portion by an articulating joint. An elongated flexible body comprises an outer sheath and an intermediate member moveably positioned with the outer sheath. A removable sheath is positioned around the branch portion to constrain the branch portion in a reduced profile configuration. The main portion of the vascular graft is positioned within the intermediate member flexible body in a compressed state. The articulating joint extends through an opening in the intermediate member such that the branch portion is positioned within the elongate body between the outer sheath and the intermediate member.

Another embodiment of the present invention comprises a method of treating a thoracic aorta, which comprises the ascending aorta, the aorta arch and the descending aorta. The method comprises providing a vascular graft comprising a main portion and a branch portion that is coupled to the main portion, providing a deployment apparatus having an outer main sheath, a delivery sheath concentrically positioned in the main sheath, wherein the delivery sheath has a groove extending along its longitudinal axis, the main portion of the vascular graft being positioned within the delivery sheath in a compressed state and the branch graft portion stored in a branch sheath in a compressed state and positioned in the main sheath adjacent to the delivery sheath. The distal end of the deployment apparatus is advanced up through the descending aorta into the ascending aorta. The main sheath is retracted to release the branch portion in its branch sheath which is positioned at least partially within a branch vessel. The main portion of the vascular graft is positioned within the descending aorta by and deployed by proximally retracting a portion of the delivery sheath. The branch portion of the vascular graft is deployed by proximally withdrawing the branch sheath from the branch portion.

Another embodiment of the present invention comprises the combination of a deployment apparatus and a vascular graft having a main portion and a branch portion that is connected to the main portion by an articulating joint. The combination includes a main elongate flexible tubular member having a proximal end, a distal end and a lumen extending therebetween, a second elongate tubular member slidably housed in the lumen of the main tubular member, having a proximal end, a distal end and a lumen extending therebetween and groove extending along a longitudinal axis and a pusher slidably housed in the lumen of the main tubular member, proximal to the second tubular member. The main portion of the vascular graft is positioned within the second tubular member in a compressed state between the distal end of the tubular member and the pusher, the branch portion of the vascular graft being positioned within the main tubular member in a compressed state adjacent to the second tubular member body such that the articulating joint is generally positioned within the longitudinal groove of the second tubular member. In addition, the second tubular member may further include a plurality of segmented constricting clips spaced apart along the longitudinal axis of the second tubular member providing additional support and flexibility to the second tubular member.

Another embodiment of the present invention comprises a branch graft deployment apparatus comprising a removable sheath cut on two sides along a longitudinal axis to divide the sheath into two halves, a locking mechanism configured to hold the two sheath halves in a closed position and a release mechanism attached to the locking mechanism. The two sheath halves are configured to hold a branch graft portion in a compressed state when in a closed position. The release mechanism is configured to release the locking mechanism to open the two sheath halves and deploy the enclosed branch graft portion.

Another embodiment of the present invention comprises a method of deploying a branch graft portion with in a branch vessel of the aorta. The method comprises providing a branch vascular graft portion, providing a branch graft delivery system deployment apparatus providing a branch graft delivery system comprising removable sheath cut on two sides along a longitudinal axis to divide the sheath into two halves having distal and proximal ends, a locking mechanism configured to hold the two sheath halves in a closed position, and a guide wire operably connected to the sheath and the locking mechanism, wherein the branch vascular graft portion is enclosed in the two sheath halves in a compressed state. The branch graft delivery system is positioned in a branch vessel of the aorta. The locking mechanism is released to open the two sheath halves and deploy the enclosed branch graft portion. The branch delivery system is withdrawn from the patient by retracting the guide wire. Further features and advantages of the present invention will become apparent to those of ordinary skill in the art in view of the detailed description of preferred embodiments which follow, when considered together with the attached drawings and claims.

BRIEF DESCRIPTION OF THE DRAWINGS

FIG. 2A is a top plan view of the vascular prosthesis of FIG. 1A in a straightened configuration.

FIG. 2C are front and review perspective views of a main body of the vascular prosthesis of FIG. 1A.

FIG. 2D are front and review perspective views of a branch body of the vascular prosthesis of FIG. 1A.

FIG. 4 is a partial cross-sectional view of a deployment apparatus having certain features and advantages according to an embodiment of the present invention.

FIG. 4A is a closer view of a distal portion of FIG. 4.

FIG. 5 is a front view of the deployment apparatus of FIG. 4.

FIG. 29 is a side view of a branch graft delivery system comprising a bifurcated sheath in a closed position.

FIG. 30 is a side view of the branch graft delivery system of FIG. 29 in an open position.

FIG. 31 is a side view of the branch graft delivery system of FIG. 29 in an open position.

FIG. 32 is a side view of the branch graft delivery system of FIG. 29 in a closed position.

FIG. 33A is a cross sectional view of the locking mechanism in a closed position.

FIG. 37 is a side view of a guide wire according to the present invention

DETAILED DESCRIPTION OF THE PREFERRED EMBODIMENT

Figure 1:
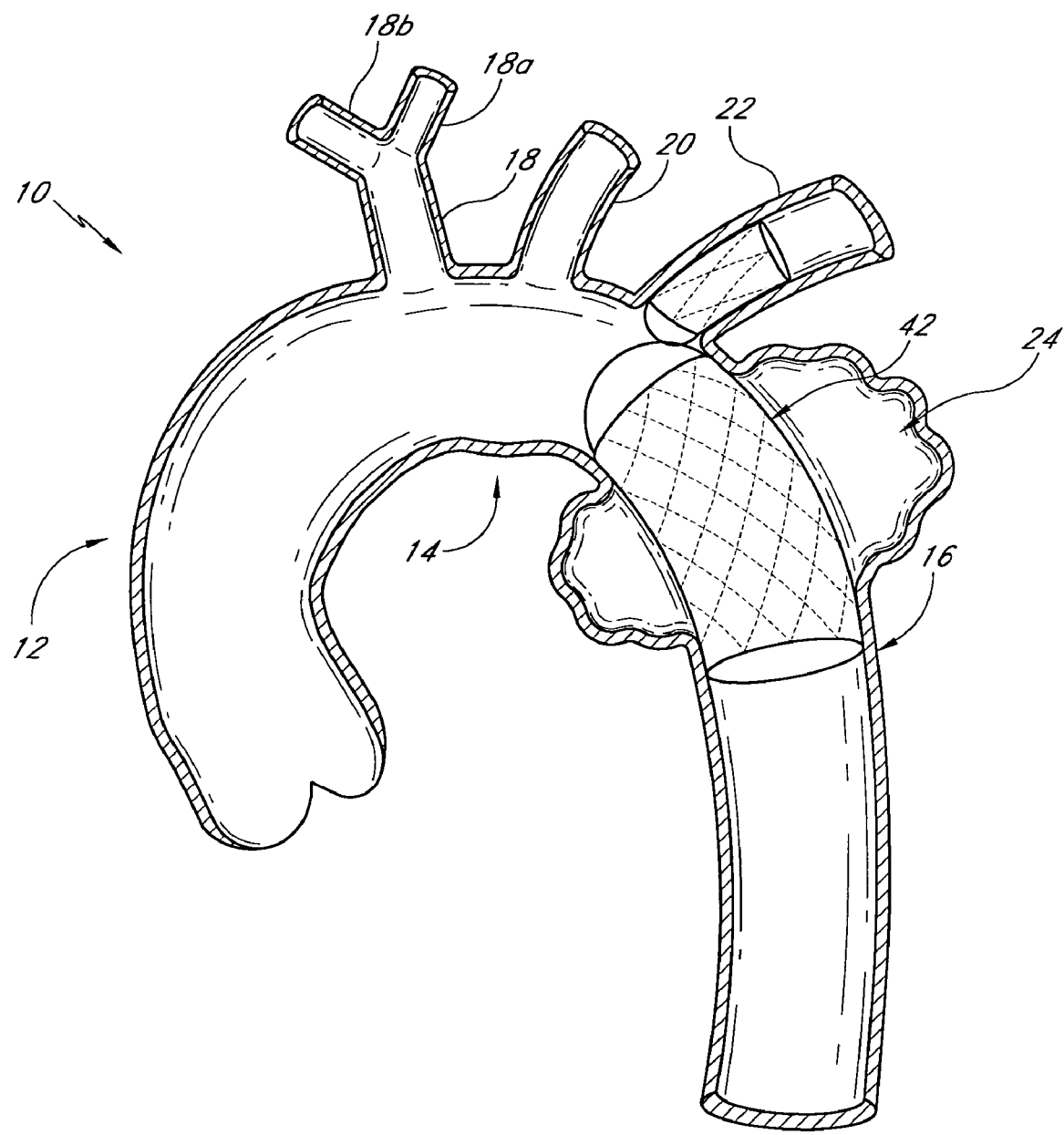
FIG. 1 is a schematic representation of the thoracic aorta and its principle branches.

FIG. 1 illustrates a schematic representation of the thoracic aorta 10. The thoracic aorta 10 is divided into the (i) ascending aorta 12, which arises from the left ventricle of the heart, (ii) the aortic arch 14, which arches from the ascending aorta 12 and (iii) the descending aorta 16 which descends from the aortic arch 14 towards the abdominal aorta. Also shown are the principal branches of the thoracic aorta 10, which include the innomate artery 18 that immediately divides into the right carotid artery 18A and the right subclavian artery 18B, the left carotid 20 and the subclavian artery 22. An aneurysm 24 is illustrated in the descending aorta 16, just below the subclavian artery 22.

FIGS. 2A-3B illustrate an endoluminal vascular prosthesis 42, in accordance with an embodiment of the present invention. As will be explained, in more detail below, the prosthesis 42 may be used to span the aneurysm 24 as shown in FIG. 1.

With initial reference to FIGS. 2A-D, the prosthesis 42 comprises a first or main body 44 and a second or branch body 46. In the illustrated embodiment, the main body 44 comprises a generally tubular body 48 having a distal end 50, which defines a distal opening 52, and a proximal end 54, which defines a proximal opening 56 (see FIG. 2C). As used herein, the terms proximal and distal are defined relative to the deployment catheter, such that the device distal end is positioned in the artery closer to the heart than the device proximal end.

In a similar manner (see FIG. 2D), the branch body 46 comprises a generally tubular body 57 having a proximal end 58, which defines a proximal opening 60, and a distal end 62, which defines a distal opening 64. As will be explained in more detail below, in one embodiment, the main body 44 is configured such that it can extend across at least a portion of the aneurysm 24 while the branch body 46 is configured to be positioned within the subclavian artery 22.

The distal end 50 of the main body 44 and the proximal end 58 of the branch body 46 are coupled together by an articulating joint 66. In one embodiment, the articulating joint 66 is configured to axially couple the branch member 46 to the main body 46 while permitting sufficient flexibility between these bodies 44, 46 such that the branch body 46 may be placed within one of the branch vessels (i.e. the innomate artery 18, the left carotid 20 or subclavian artery 22) while the main body 44 is positioned within the thoracic aorta 10.

Figure 2B:
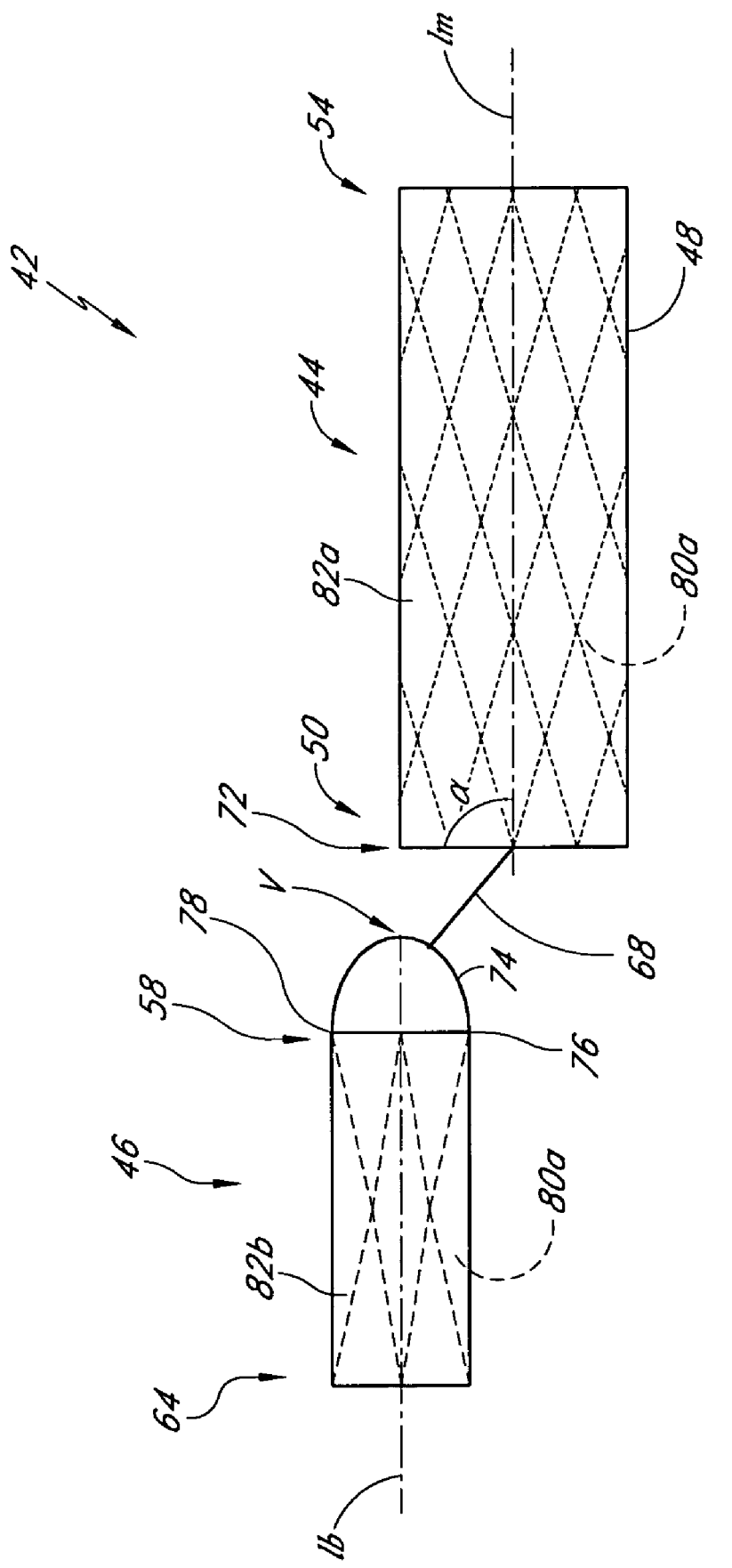
FIG. 2B is a side plan view of the vascular prosthesis of FIG. 1A in a straightened configuration.

With reference to FIGS. 2A and 2B, in the illustrated embodiment, the articulating joint 66 comprises a first semi-circular hoop 68 having a first end 70 and a second end 72 that are coupled to the distal end 50 of the first body 44. A second semi-circular hoop 74 is provided on the branch body 46 and also has a first end 76 and a second end 78 that are attached to the proximal end 58 of the branch body 46. As shown in FIGS. 2A and 2B, the hoops 68, 74 are linked together to form the articulating joint 66. In the illustrated arrangement, the ends 76, 78 of the second hoop 74 are coupled to the proximal end 58 of the branch body 46 such that the second hoop 74 extends generally parallel to the longitudinal axis lb of the branch body 46. In contrast, the ends 70, 72 of the first hoop 68 may be coupled to the distal end 50 of the main body 44 such that the first hoop 68 forms an angle a with respect to the longitudinal axis lm of the main body 44. In this manner, as shown in FIG. 2B, the longitudinal axis lb of the branch body 46 may lie generally above or offset from the longitudinal axis lm of the main body 44. The first and second hoops 68, 74 may be attached to the main and branch bodies 44, 46 in any of a variety of ways. For example, the hoops 68, 74 may be coupled or formed as part of the tubular skeleton described below and/or coupled and/or formed with the sleeve described below.

Preferably, the articulating joint 66 provides a substantial range of motion between the main body 44 and the branch body 46. In this manner, the prosthesis 42 may be installed in a wide variety of patients in which the angles between the innomate artery 18, the left carotid 20, subclavian artery 22 and the thoracic aorta 10 may vary substantially from patient to patient. With reference to FIG. 3A which is a side elevational view of the prosthesis 42, the joint 66 preferably allows the branch body 46 to be adjusted to any of a variety of angular orientations with respect to the main body 44. The angle b represents the angular adjustment between the longitudinal axes lm, lb of the two bodies 44, 46 in a first plane generally about a vertex v positioned generally between the apexes of the first and second loops 68, 74. The angle b is limited primarily by the interference between the distal end 50 of the main body 44 and the proximal end 58 of branch body 46, and the configuration of the joint 66. It should be appreciated that the maximum angle of adjustment between the longitudinal axes lm, lb of the main and branch bodies 44, 46 in an symmetrical joint 66 as illustrated is generally half of the angle b. Depending upon the environment of use, the angle b is preferably at least about 120 degrees and often at least about 180 degrees.

Figure 3B:
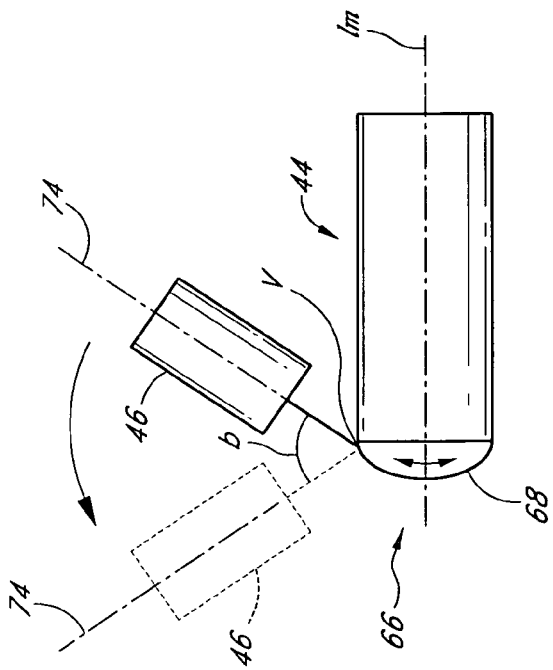
FIG. 3B is a side plan view of the vascular prosthesis of FIG. 1A with the with main portion rotated 180 degrees with respect to FIG. 3A and showing the range of angular adjustment.
Figure 3C:
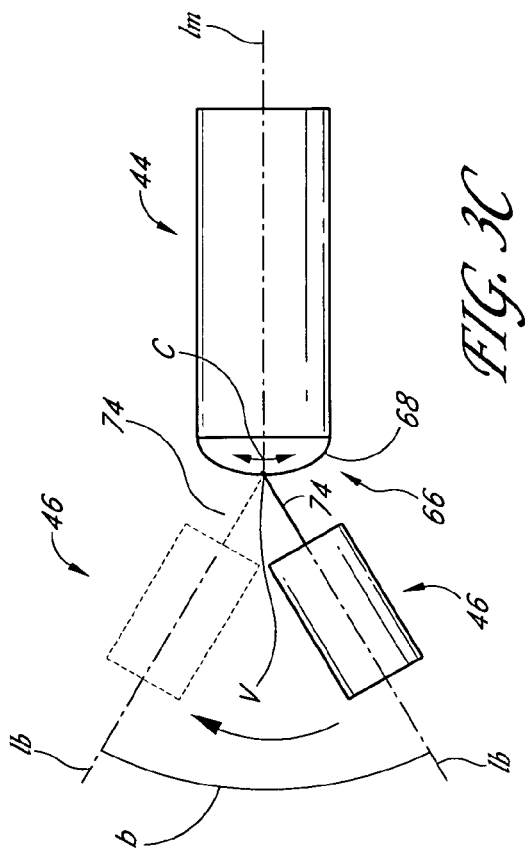
FIG. 3C is a top plan view of the vascular prosthesis of FIG. 1A showing the range of angular adjustment.
Figure 3A:
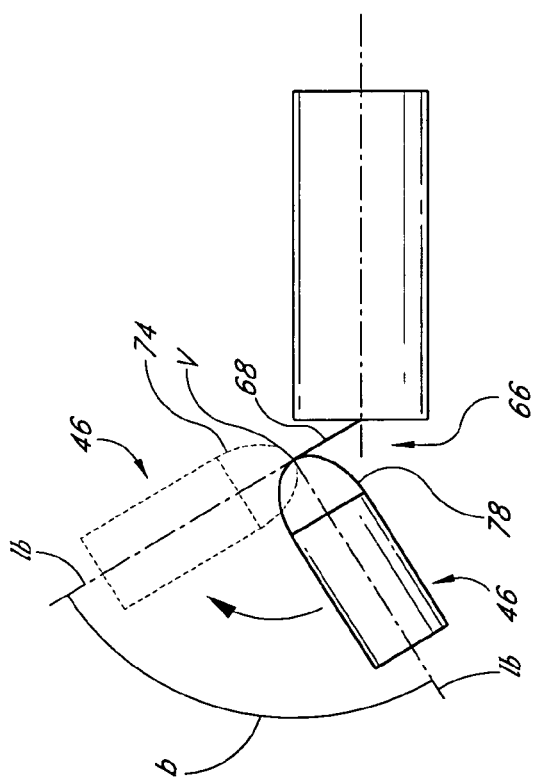
FIG. 3A is a side plan view of the vascular prosthesis of FIG. 1A showing the range of angular adjustment.

With reference now to FIGS. 3B and 3C, the branch body 46 preferably includes another degree of motion with respect to the main body 44. Specifically, as shown in FIG. 3B, the vertex v about which the branch body 46 may be angularly adjusted may be moved laterally with respect to the longitudinal axis of the main body 44 as the second hoop 74 slides along the first hoop 68. This provides the articulating joint 66 with an additional range of movement and flexibility. Advantageously, with reference to FIG. 3B, this arrangement allows the main body 44 to be rotated about its longitudinal axis lm with respect to the branch body 46 while preserving at least some if not all of the angular adjustment about the vertex v described above.

In addition, or in the alternative, the articulating joint 66 may also include additional ranges of motion. For example, as shown in FIG. 3C, the illustrated embodiment advantageously allows the branch body 46 to be adjusted to any of a variety of angular orientations defined within a cone having vertex v that is generally positioned between the apexes of the first and second hoops 68, 74. The angle c represents the angular adjustment between the two bodies and the angle b is the lateral range of angular adjustment in a single plane within which the hoop 68 resides. The maximum angular adjustment between the longitudinal axes lm, lb of the main and branch bodies 44, 46 in the illustrated configuration is generally half of the angle c. Depending upon the environment of use, the angle c is preferably at least about 120 degrees and often at least about 180 degrees.

It should be appreciated that the illustrated articulating joint 66 represents only one possible configuration for the articulating joint 66 and of a variety of other articulating joint structures may be used to provide one or more of the degrees and ranges of angular adjustment described above. Such articulating joint structures include, but are not limited to mechanical linkages (e.g., inter-engaging hoops of different configurations and shapes, sliding structures, rails, hinges, ball joints, etc.), flexible materials (e.g., flexible wires, fabric, sutures, etc.) and the like.

For example, a woven or braided multi-strand connector can extend between the main body 44 and the branch body 46, without the use of first and second interlocking sliding components as illustrated. Filaments for multi-strand or single strand connectors may comprise any of a variety of metals (e.g. Nitinol, stainless steel) or polymers (e.g. Nylon, ePTFE, PET, various densities of polyethylene, etc.) depending upon the desired tensile strength and performance under continuous repeated movement. A single strand or multi-strand connector may extend from one of the main body 44 and branch body 46, with an eye on the free end, slideably carried by a hoop or strut on the other of the main body 44 and branch body 46. As a further alternative, a proximal extension of the frame work for the branch body 46 may be provided, to interlock with a distal extension of the framework for the main body 44. The use of a particular articulating joint 66 will be governed by a variety of considerations, including the desired angles of adjustability and degrees of freedom, as well as materials choices and deployment considerations which can be optimized for specific vascular graft designs.

As compared to the illustrated embodiment, such structures may be configured to have more or less range of motion and/or degrees of adjustment. For example, in some embodiments, it may be advantageous to provide angular adjustment about a vertex v between the main and branch bodies 44, 46 only within a single plane. In other embodiments, it may be advantageous to provide angular adjustment about a vertex v between the main and branch bodies 44, 46 only within a single plane while also permitting the vertex v to move about a path as described above with reference to FIGS. 3B and 3C.

With reference back to FIGS. 2A and 2B, the vascular prosthesis 42 can be formed using a variety of known techniques. For example, in one embodiment, one or both of the bodies 44, 46 comprises an expandable tubular support or skeleton 80a, 80b, and a polymeric or fabric sleeve 82a, 82b that is situated concentrically outside and/or inside of the tubular support 80a, 80b. The sleeve 82a, 82b may be attached to the tubular support 80a, 80b by any of a variety of techniques, including laser bonding, adhesives, clips, sutures, dipping or spraying or others, depending upon, e.g., the composition of the sleeve 82a, 82b and overall prosthesis design. In another embodiment, the tubular support 80a, 80b, may be embedded within a polymeric matrix which makes up the sleeve 82a, 82b.

The sleeve 82a, 82b may be formed from any of a variety of synthetic polymeric materials, or combinations thereof, including ePTFE, PE, PET, Urethane, Dacron, nylon, polyester or woven textiles. In one embodiment, the material of sleeve 82a, 82b is sufficiently porous to permit ingrowth of endothelial cells, thereby providing more secure anchorage of the prosthesis and potentially reducing flow resistance, sheer forces, and leakage of blood around the prosthesis. The porosity characteristics of the polymeric sleeve may be either homogeneous throughout the axial length of the main and branch bodies 44, 46, or may vary according to the axial position along these components. For example, with reference to FIG. 1A, it may be advantageous to configure the distal end 50 and the proximal end 54 of the main body 44, which seat against the native vessel wall, on either side of the aneurysm 24, to encourage endothelial growth, or, to permit endothelial growth to infiltrate portions of the prosthesis in order to enhance anchoring and minimize leakage. Because anchoring may be less of an issue, the central portion of the main body 44, which spans the aneurysm 24, may be configured to maximize lumen diameter and minimizing blood flow through the prosthesis wall and therefore may either be generally nonporous, or provided with pores of relatively lower porosity.

In modified embodiments, the prosthesis 42 may be provided with any of a variety of tissue anchoring structures, such as, for example, barbs, hooks, struts, protrusions, and/or exposed portions of the tubular support 80a, 80b. In other embodiments, the tubular support 80a, 80b may extend beyond one or more of the ends of the sleeve material. Such anchoring structures over time may become embedded in cell growth on the interior surface of the vessel wall. These configurations may help resist migration of the prosthesis 42 within the vessel and reduce leakage around the ends of the prosthesis 42. The specific number, arrangement and/or structure of such anchoring structures can be optimized through routine experimentation.

In one particular embodiment, the branch body 46 comprises an uncovered stent. That is, the branch body 46 may include a tubular wire support structure 80b but does not include a sleeve, or only a portion of the branch body 46 includes a sleeve. In contrast, the main body 44, which may be used to span and isolate the aneurysm 24, is covered partly or wholly by a sleeve. In this manner, the tubular structure 80b of the branch body 46 serves to resist migration and act as an anchoring structure for the main body 44 within the thoracic aorta 10.

In still another embodiment, the branch body 46 may be used to occlude or partially occlude one of the branch vessels (e.g., the right and left carotids 18, 20 and the subclavian 22 artery). In such an embodiment, the branch body 46 may include an occluding body (not shown), such as an end cap or membrane carried by the wire support structure, which is configured to extend across the branch vessel to partially or totally occlude the vessel.

Those of skill in the art will recognize that any of a variety of tubular supports may be utilized with the illustrated embodiment. In one embodiment, the tubular supports are configured to be expanded via an internal expanding device (e.g., a balloon). See e.g., U.S. Pat. No. 6,123,722, which is hereby incorporated by reference herein. In another embodiment, the tubular support is wholly or partially self expandable. For example, a self expandable tubular support may be formed from a shape memory alloy that can be deformed from an original, heat-stable configuration to a second heat-unstable configuration. See e.g., U.S. Pat. No. 6,051,020, which is hereby incorporated by reference herein. The supports may be formed from a piece of metal tubing that is laser cut.

In another embodiment, the support comprises one or more wires, such as the tubular wire supports disclosed in U.S. Pat. Nos. 5,683,448, 5,716,365, 6,051,020, 6,187,036, which are hereby incorporated by reference herein, and other self-expandable configurations known to those of skill in the art. Self expandable tubular structures may conveniently be formed with a series of axially adjacent segments. Each segment generally comprises a zig-zag wire frame having a plurality of apexes at its axial ends, and wire struts extending therebetween. The opposing apexes of adjacent segments may be connected in some or all opposing apex pairs, depending upon the desired performance. In other embodiments, one or more of the individual segments may be separated from adjacent segments and retained in a spaced apart, coaxial orientation by the fabric sleeve or other graft material.

The tubular support or skeleton need not extend through the entire axial length of the branch and/or main bodies. For example, in one embodiment, only the distal and proximal ends 50, 54, 58, 62 of the main and branch bodies 44, 46 are provided with a tubular skeleton or support. In other embodiments, the prosthesis 42 is "fully supported". That is, the tubular support extends throughout the axial length of the branch and/or main bodies 44, 46.

Suitable dimensions for the main and branch bodies 44, 46 can be readily selected taking into account the natural anatomical dimensions in the thoracic aorta 10 and its principal branches (i.e., the innomate artery 18, left carotid 20 and subclavian 22 arteries).

For example, main branch bodies 44 will have a fully expanded diameter within the range of from about 20 mm to about 50 mm, and a length within the range of from about 5 cm to about 20 cm for use in the descending aorta as illustrated in FIG. 1. Lengths outside of these ranges may be used, for example, depending upon the length of the aneurysm to be treated, the tortuosity of the aorta in the affected region and the precise location of the aneurysm. Shorter lengths may be desirable for the main body 44 when treating aneurysms in the ascending aorta or the aortic arch as will be appreciated by those of skill in the art.

Branch bodies 46 for use in the subclavian artery will generally have a length within the range of from about 10 mm to about 20 mm, and a fully expanded diameter within the range of from about 2 cm to about 10 cm. Both the main body 44 and branch body 46 will preferably have a fully expanded diameter in an unconstrained state which is larger than the inside diameter of the artery within which they are to be deployed, in order to maintain positive pressure on the arterial wall.

The minimum length for the main branch 44 will be a function of the size of the aneurysm 24. Preferably, the axial length of the main branch 44 will exceed the length of the aneurysm, such that a seating zone is formed at each end of the main branch 44 within which the main branch 44 overlaps with healthy vascular tissue beyond the proximal and distal ends of the aneurysm 24.

The minimum axial length of the branch body 46 will depend upon its configuration, and whether or not it includes anchoring structures such as barbs, high radial force, or other features or structures to resist migration. In general, the branch body 46 will be optimized to provide an anchor against migration of the main body 44, and may be varied considerably while still accomplishing the anchoring function.

The length of the joint is considered to be the distance between the expandable wire support for the branch body 46 and for the main body 44. In general, the length of the joint will be at least about 2 mm, and in some embodiments at least about 1 mm. Longer lengths may also be utilized, where desirable to correspond to the distance between the anatomically proximal end of the aneurysm and the desired branch vessel within which the anchoring body is to be placed. Joint lengths of at least about 50% of the expanded diameter of the branch body 44, and in some instances at least 100% and as much as 200% or more of the expanded diameter of the branch body 46 may be utilized, depending upon the anatomical requirements.

FIG. 4 is a partial cross-sectional side view of one embodiment of a deployment apparatus 100, which can be used to deploy the prosthesis 42 described above. FIG. 5 is a front view of the apparatus 100. The deployment apparatus 100 comprises an elongate flexible multi-component tubular body 102 comprising an outer sheath 104 and an inner proximal stop or pusher 106 axially movably positioned within the outer sheath 104. The outer sheath 104 may be provided with a proximal hub or valve 107 and an irrigation side arm 109, which is in fluid communication with the distal end of the catheter such as through the annular lumen formed in the space between the outer sheath 104 and pusher 106.

With continued reference to FIG. 4, a central core 108 having a smaller outer diameter than the pusher 106 may extend from the distal end of the pusher 106. A distal cap or end member 110, in turn, may be coupled to the distal end of the central core 108. A guidewire lumen 112 (FIG. 5) preferably extends through the distal cap 110, central core 108 and pusher 106.

With reference to FIG. 4A, which is a closer view of the distal end of the deployment apparatus 100, the prosthesis 42 may be positioned in a compressed or reduced diameter state within the outer sheath 104 between the distal cap 110 and the distal end of the pusher 106. As will be explained in detail below, proximal (inferior direction) retraction of the outer sheath 104 with respect to the pusher 106 will deploy the prosthesis 42

With continued reference to FIG. 4A, preferably, the outer sheath 104 includes a region of increased flexibility or articulation 114. When the prosthesis 42 is mounted within the outer sheath 104, the articulating connection 66 is preferably axially aligned with the region of increased flexibility or articulation 114. The region of increased flexibility or articulation 114 may be formed in any of a variety of manners. In the illustrated embodiment, the region of increased flexibility or articulation 114 is formed by providing the tubular member with a plurality of scores, grooves or thinned areas 116 such as a plurality of circumferential slots, which increase the flexibility of the outer sheath 104 in this region. In modified embodiments, the region of increased flexibility or articulation 114 may be formed by using a more flexible material and/or providing a mechanical linkage or a bellows configuration. In one embodiment, the central core 108 also includes an area of increased flexibility or articulation, such as an annular recess in the outer wall, which is axially aligned with the region of increased flexibility or articulation 114 on the outer sheath 104.

The tubular body 102 and the other components of the deployment apparatus 100 can be manufactured in accordance with any of a variety of techniques well known in the catheter manufacturing field. Extrusion of tubular catheter body parts from material such as Polyethylene, PEBAX, PEEK, nylon and others is well understood. Suitable materials and dimensions can be readily selected taking into account the natural anatomical dimensions in the thoracic aorta 10 and its principle branches 18, 20, 22, together with the dimensions of the desired implant and percutaneous or other access site.

Figure 6:
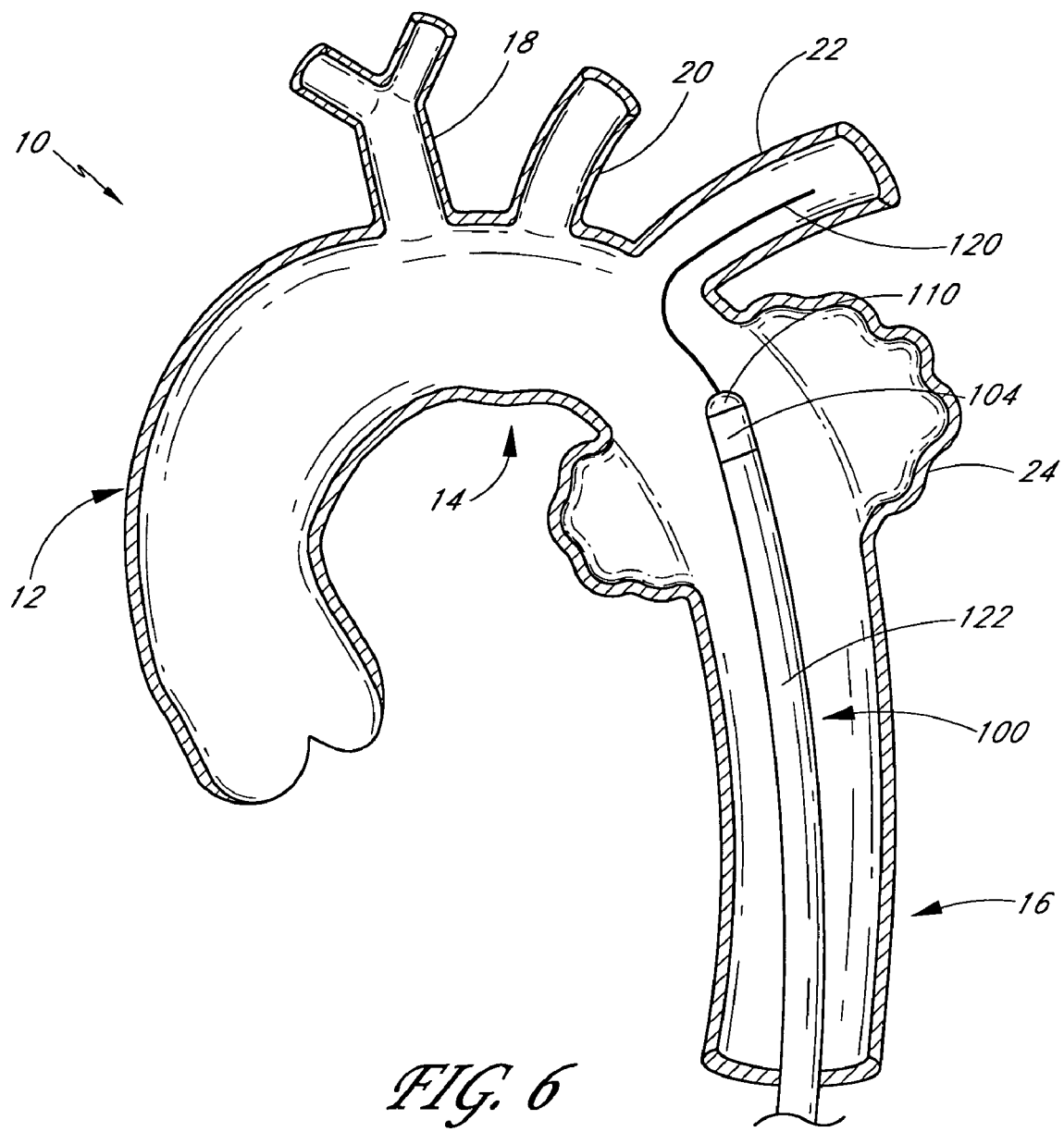
FIG. 6 is a schematic representation of a guide wire and deployment apparatus positioned across an aneurysm positioned in the descending aorta.

A technique for deploying the prosthesis 42 using the deployment apparatus 100 for treating an aneurysm 24 in the descending aorta 16 will now be described with reference to FIGS. 6-9. As shown in FIG. 6, a standard 0.035" diameter guide wire 120 is preferably positioned across the aneurysm 24 and into the subclavian artery 22. The guide wire may be introduced, for example, through a percutaneous puncture, and advanced superiorly towards the aneurysm and thoracic aorta 10. In one embodiment, the percutaneous puncture is formed on the femoral artery.

Figure 7:
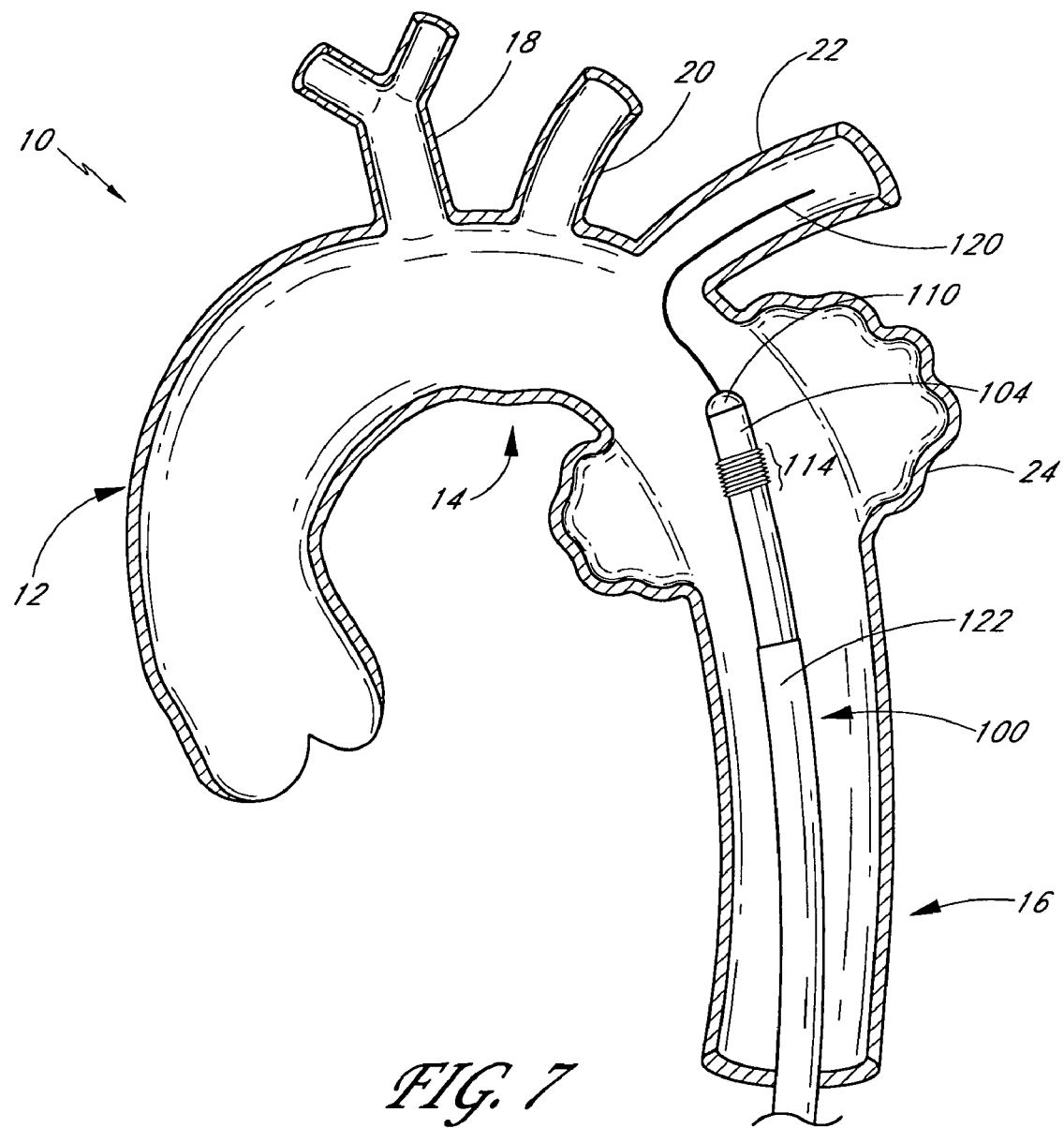
FIG. 7 is a schematic representation as in FIG. 6 with an outer sheath of the deployment apparatus proximally retracted.
Figure 8:
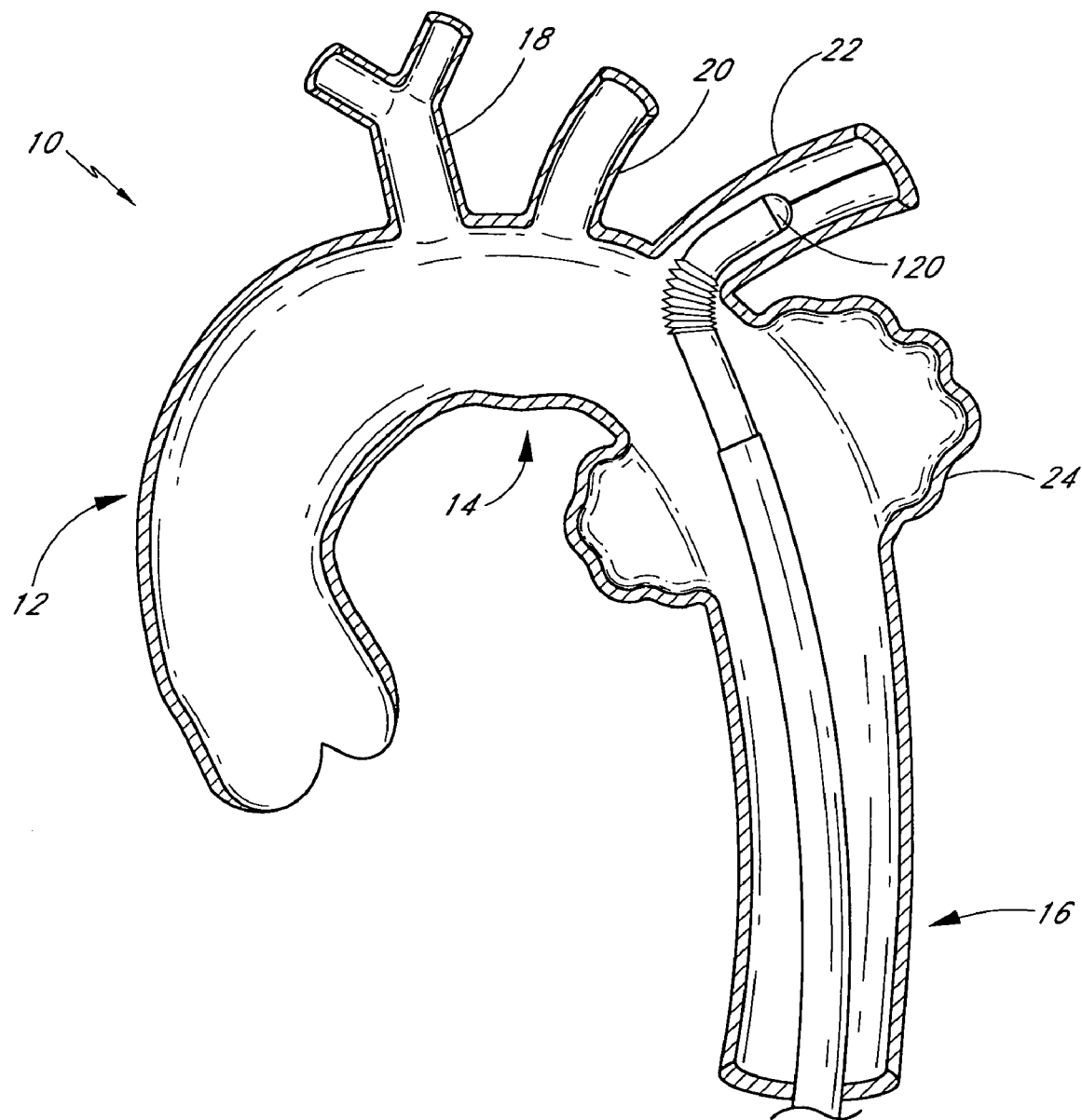
FIG. 8 is a schematic representation as in FIG. 7 with the distal end of the deployment apparatus advanced into the subclavian artery.

The deployment apparatus 100 is advanced over the wire until the distal end of the catheter is positioned at or near the thoracic aorta. During this step, the deployment apparatus 100 may be covered at least in part by an outer tubular member 122, which preferably extends over the area of increased flexibility 114. The outer tubular member 122 advantageously increases the stiffness of the apparatus 100 thereby enhancing its pushability. As shown in FIG. 7, the outer tubular member 122 may be withdrawn exposing the area of increased flexibility 114. The distal end of the deployment apparatus may be then advanced (see FIG. 8) until the branch body (not shown in FIG. 8) within the apparatus 100 is positioned in the subclavian artery 22 and the flex point 114 is positioned in the vicinity of the ostium. The area of increased flexibility 114 advantageously facilitates advancement of the deployment apparatus 100 over the guide wire 120 and permits the catheter to navigate the tortuous turn from the descending aorta 16 into the subclavian artery 22.

Figure 9:
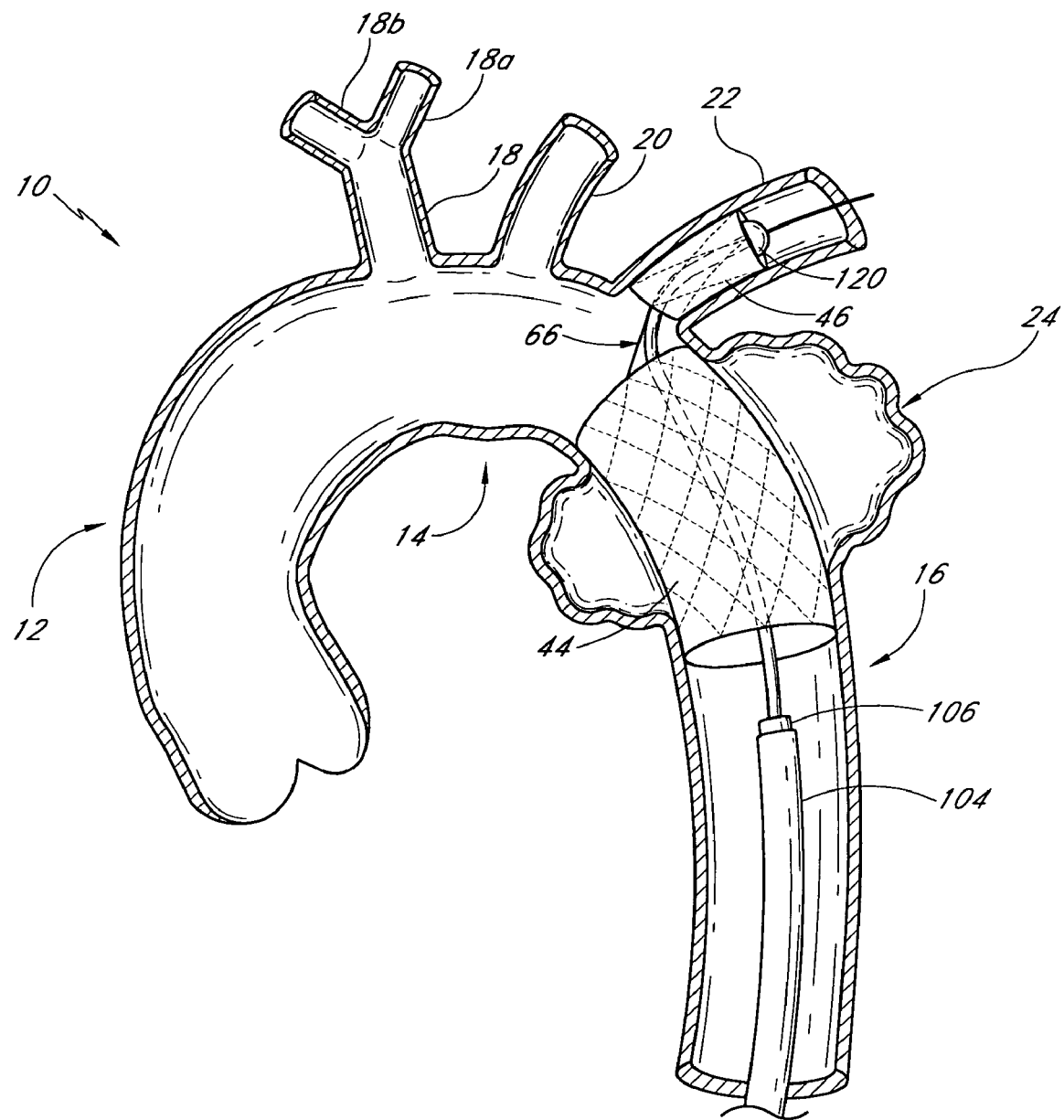
FIG. 9 is a schematic representation as in FIG. 8 with the prosthesis deployed in the subclavian artery and the descending aorta.

With reference to FIG. 9, the outer sheath 104 may be proximally withdrawn thereby allowing the branch body 46 to expand within the branch vessel 22. Further proximal retraction, exposes the main branch 44 allowing it to expand in the thoracic aorta 10, spanning at least a portion, and more preferably the entire aneurysm 24. With the prosthesis 42 deployed, the deployment apparatus 100 may be proximally withdrawn through the deployed prosthesis 42. The deployment catheter 100 may thereafter be proximally withdrawn from the patient by way of the percutaneous access site.

The deployment apparatus 100 and/or the prosthesis 42 may include one or more radio opaque markers such that the apparatus 100 and/or the prosthesis 42 may be properly orientated with respect to the anatomy. For example, with respect to the illustrated embodiment, it is generally desirable that the first hoop 68 of the articulating joint 66 generally point towards the subclavian artery 22. Any of a variety of techniques may be used to provide radio opaque markers, such as, for example, providing the components of the deployment apparatus 100 and/or the prosthesis 42 with bands or staples made of radio opaque material or dispersing radio opaque material into the material that forms the components of the apparatus.

The illustrated embodiment has several advantages over the prior art. For example, some prior art techniques involve placing an inverted bifurcated or "Y" graft into the aorta 10 from a branch vessel. In these techniques, a deployment catheter is inserted into the aorta 10 through one of the branch vessels (typically one of the carotids 18b, 20). The legs of Y-graft are then deployed within the aorta 10 with the main trunk extending into the branch vessel. This technique has several disadvantages. For example, inserting a deployment catheter into the branch vessels, especially the carotids, may dislodge plague thereby resulting in a stroke. In addition, the deployment step may temporarily occlude the carotid arteries vessel potentially obstructing cerebral blood flow causing severe damage to the patient. Another technique for inserting a vascular graft into the aorta 10 involves advancing a deployment catheter up through the descending aorta 16. The vascular graft is then deployed in the aorta. The vascular graft may include openings or fenestrations that must be aligned with the branch vessels. Branch grafts for the branch vessels may then be attached in situ to the main graft. Such techniques are time intensive and require a high degree skill and experience. In addition, these arrangements may create leakages near or around the fenestrations, leading to endoleaks and eventual graft failure.

In contrast, in the illustrated embodiment, the deployment apparatus 100 may be advanced through the descending aorta 16 avoiding the risks associated with advancing a catheter through the carotids. The prosthesis 42 may be deployed with the branch body 46 inserted into the branch vessel and the main body 44 in the aorta 10 by withdrawing the outer sheath 104. In this manner, the branch body 46 provides an anchor for the main body 44. This is particularly advantageous for aneurysms 24 that are positioned near a branch vessel. In such circumstances, the aorta 10 may not provide a large enough landing zone to properly support and anchor a graft positioned solely in the aorta, which may lead to endoleaks. The range of motion provided by the articulating joint 66 advantageously allows the prosthesis 42 to be used by surgeons with varying degrees of skill and experience. Specifically, because of the articulated joint 66, the prosthesis 42 may be misaligned rotationally with respect to the branch vessels.

Figure 10:
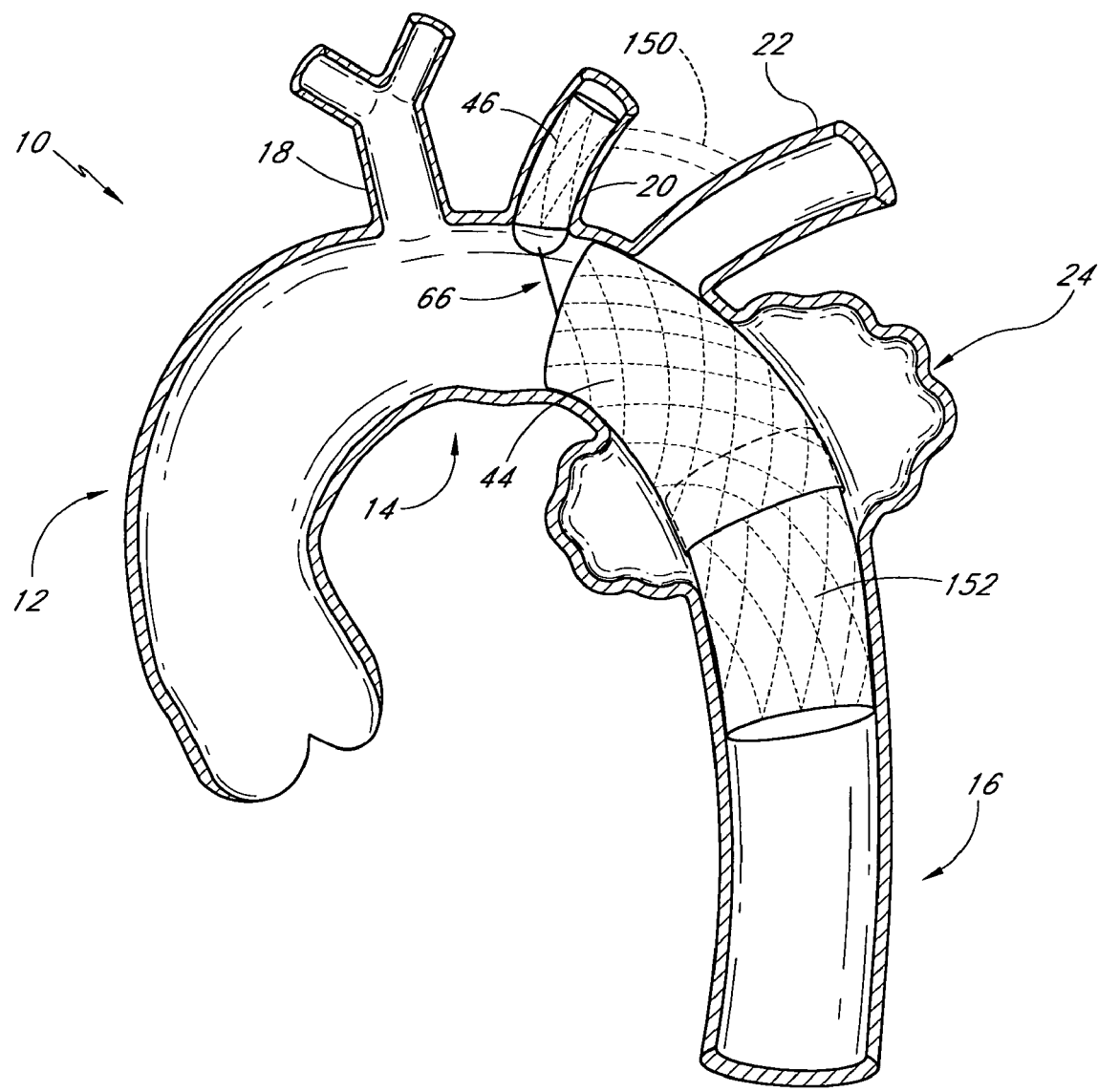
FIG. 10 is a schematic representation of an aneurysm in the descending thoracic aorta with a prosthesis having certain features and advantages according to the present invention positioned therein.

With reference to FIG. 10, the above-described procedure may be adapted to treat an aneurysm 24 positioned close the subclavian artery 22 and/or an aneurysm that includes the subclavian artery 22. This significantly reduces the landing zone available for grafts positioned within the aorta 10. In such a procedure, the branch body 46 may be deployed within the left carotid 20 while the main body 44 may deployed at least partially within the aortic arch 14 and may extend across the subclavian artery 22. As part of such a method, a carotid-subclavian bypass 150 may be performed to direct flow from the left carotid 20 to the subclavian artery 22. In another embodiment, the main body 46 may include may include openings and/or gaps in the sleeve material to allow blood flow from the thoracic aortic artery into the subclavian artery 22. Other arrangements for allowing blood from the aorta 10 to pass through the prosthesis 42 may also be used. For example, the porosity of the sleeve in the main body 44 may be increased and/or various holes or openings may be formed in the sleeve.

As shown in FIG. 10, an extension or cuff graft 152 may be positioned within the main body 44 to effectively lengthen the prosthesis 42. In one embodiment, the cuff 152 may be arranged in a similar manner as the main body 44. The cuff 152 may be deployed with a second deployment apparatus and in a manner such that the distal end of the cuff 152 is expanded within proximal end of the main body 44 in an overlapping relationship. In some embodiments, it may be advantageous to provide any of a variety of complementary retaining structures between the main body 44 and the cuff 152. Such structures include, but are not limited to, hooks, barbs, ridges, grooves, etc. The cuff 152 may be attached in situ (see e.g., U.S. Pat. No. 6,685,736, the disclosure of which is hereby incorporated by reference in its entirety herein) or before deployment.

Figure 11:
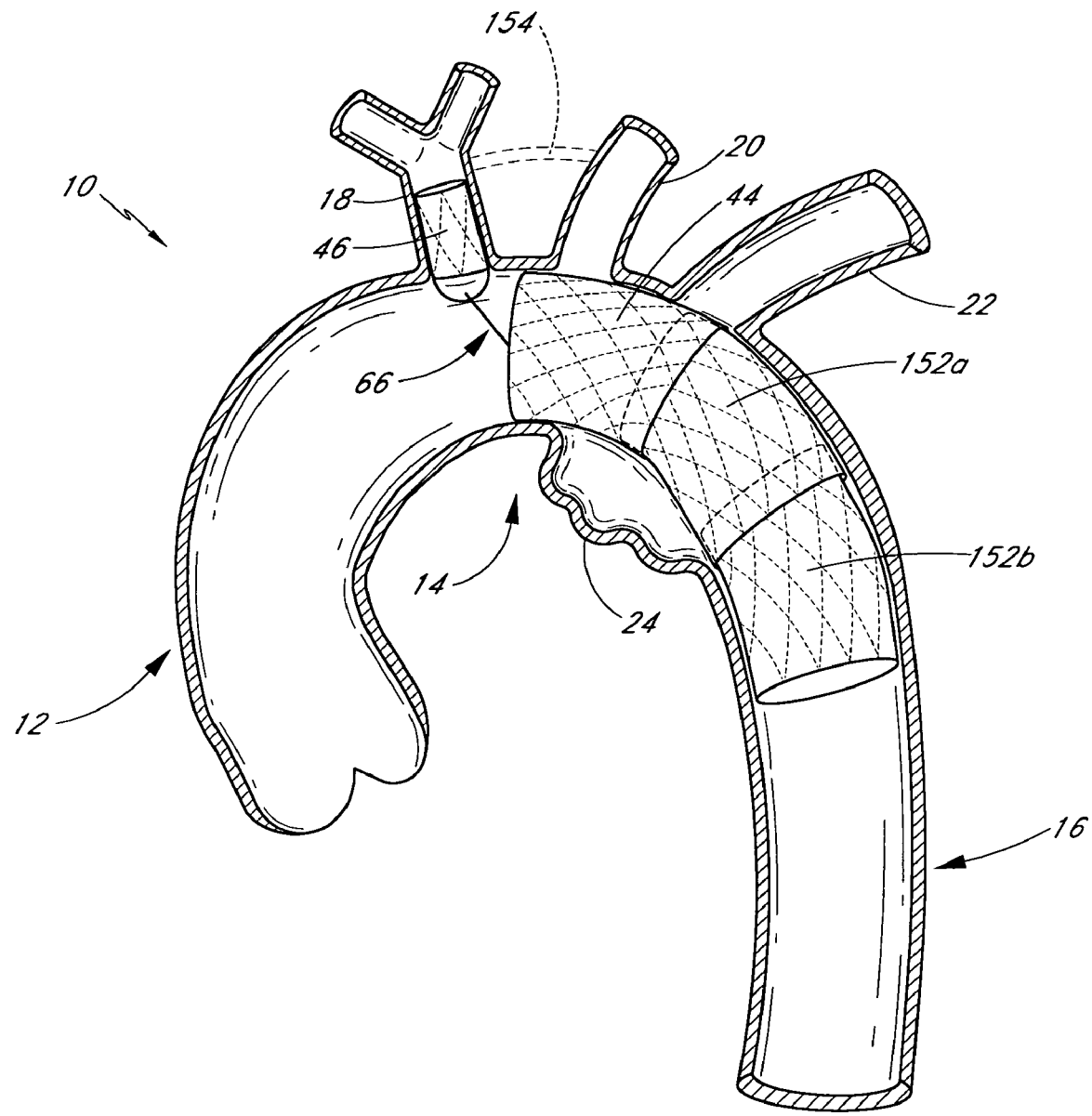
FIG. 11 is a schematic representation of an aneurysm in the aortic arch of the thoracic aorta with a prosthesis having certain features and advantages according to the present invention positioned therein.

With reference to FIG. 11, the above-described procedure may also be adapted to treat an aneurysm 24 positioned in the aortic arch 14. For example, the branch body 46 may deployed in the in a manner similar to that described above. The main body 44, in turn, may extend across the left carotid 20 and/or subclavian artery 22. One or more cuffs 152a, 152b may be provided and deployed as described above, to extend the prosthesis 42 through the aortic arch 14 to isolate the aneurysm 24. In another embodiment, the main body 44 may be configured to extend through the entire aortic arch 14. As shown in FIG. 11, in embodiments where the left carotid and/or subclavian are effectively closed by the main body 44 and/or the cuffs 152a, 152b, a carotid to carotid bypass 154 may be accomplished using open surgical techniques. In a modified embodiment, the main body 44 and/or cuffs 152a, 152b may include openings and/or gaps in the sleeve material to allow blood flow into the left carotid 20 and/or subclavian artery 22. As described above, other arrangements for allowing blood to pass through the prosthesis 42 may also be used.

Figure 12:
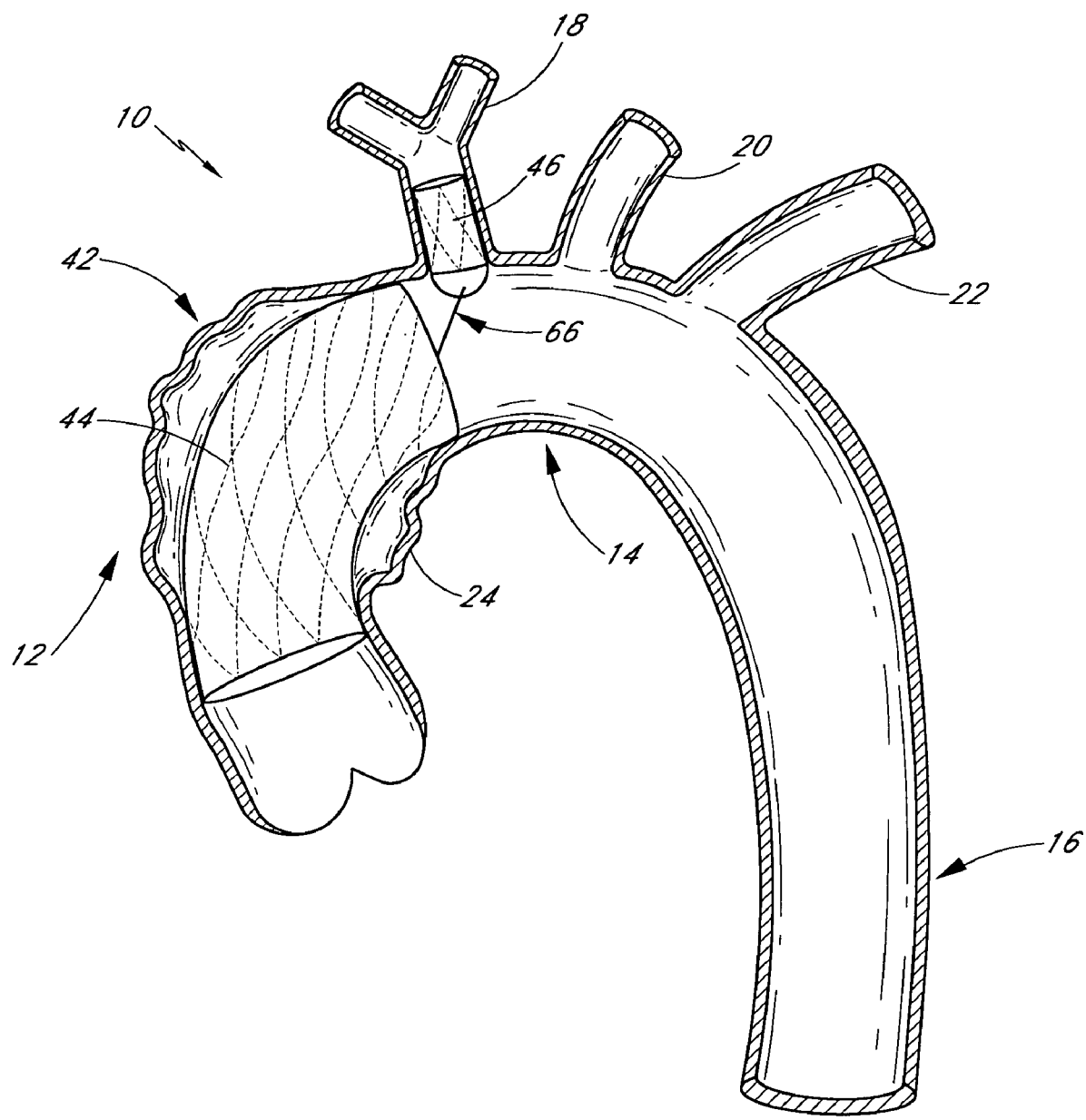
FIG. 12 is a schematic representation of an aneurysm in the ascending thoracic aorta with a prosthesis having certain features and advantages according to the present invention positioned therein.

FIG. 12 illustrates the prosthesis 42 described above placed within the aorta 10 to isolate an aneurysm 24 in the ascending aorta 14. In this embodiment, the deployment apparatus 100 may be inserted into the aorta 12 from the innomate artery 18 and the main branch 44 may be deployed first by proximally withdrawing the outer sheath 104 into the right carotid innomate artery 18.

Figure 14:
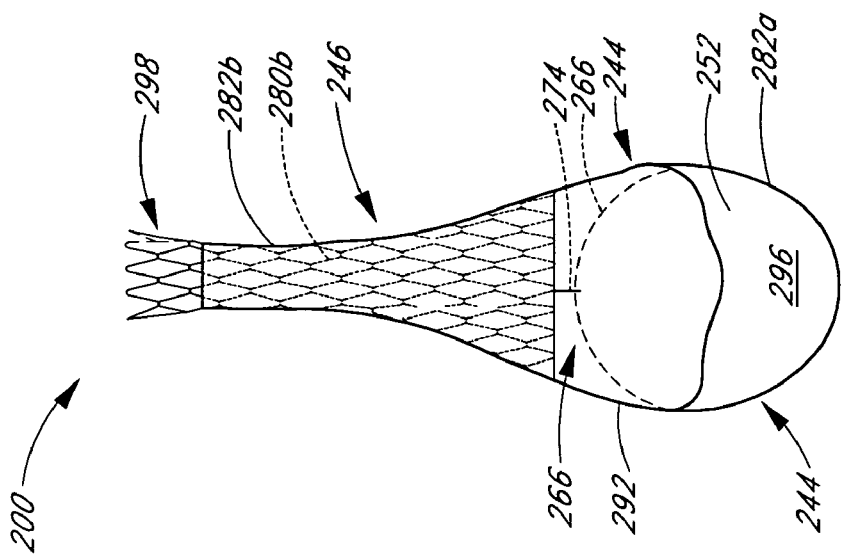
FIG. 14 is a front view of the prosthesis of FIG. 13.
Figure 13:
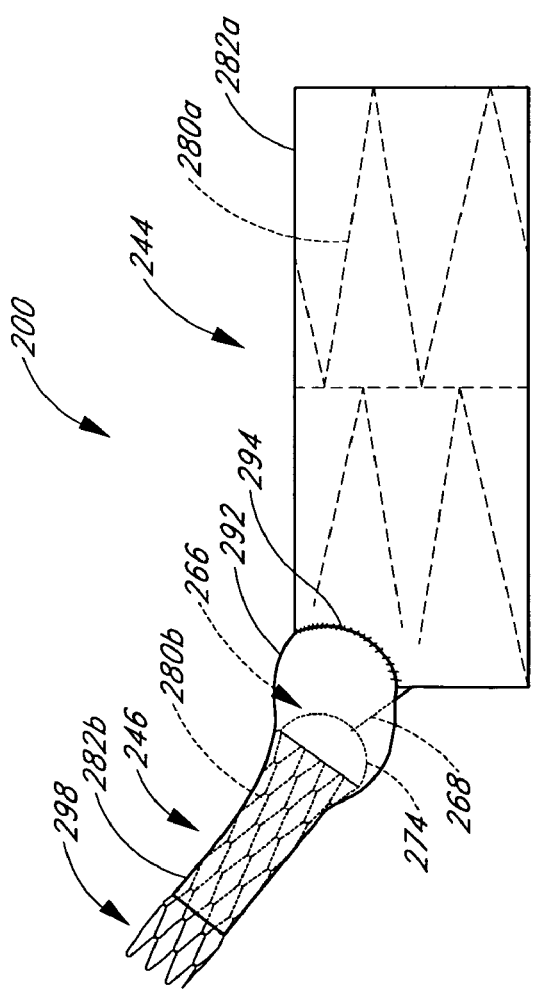
FIG. 13 is a side view of another embodiment of a vascular prosthesis.

FIGS. 13 and 14 are side and front views, respectively, of a modified embodiment of vascular graft 200. In these figures, like elements to those shown in FIGS. 2A-2D are designated with like reference numerals, preceded by the numeral "2". As shown, the vascular graft 200 generally comprises a first or main body 244 and a second or branch body 246, which are coupled together by an articulating joint 266. As described above, the articulating joint 266 may be configured as described above and in the illustrated embodiment includes a first hoop 268 and a second hoop 274. The bodies 244, 246 may comprise a tubular support or skeleton 280a, 280b and a polymeric or fabric sleeve 282a, 282b as described above.

In this embodiment, a connection portion 292 extends between the fabric sleeves 282a, 282b of the bodies 244, 246. The connection portion 292 generally extends over the articulating joint 266 and may be formed of the same material as the sleeves 282a, 282b. In the illustrated embodiment, the connection portion 292 is an extension of the sleeve 282b of the branch body 246 that is attached to the sleeve 282a of the main body 244 by stitches 294. Of course, various other configurations may be used to form the connection portion 292. The connection portion 292 is configured to leave at least a portion 296 of the distal opening 252 of the main body 244 open such that fluid may flow into the main body 244. This embodiment may be particularly advantageous for aneurysms positioned near, at and/or within a branch vessel to the thoracic aorta 10. In such applications, the connection portion 292 may extend across the aneurysm thereby isolating the aneurysm.

With continued reference to FIGS. 13 and 14, in the illustrated arrangement, a portion 298 of the tubular skeleton 280*b* of the branch body 246 extends distally beyond the end of the sleeve 282*b* to provide an additional distal anchoring mechanism for the branch body 246 as described above.

Figure 15:
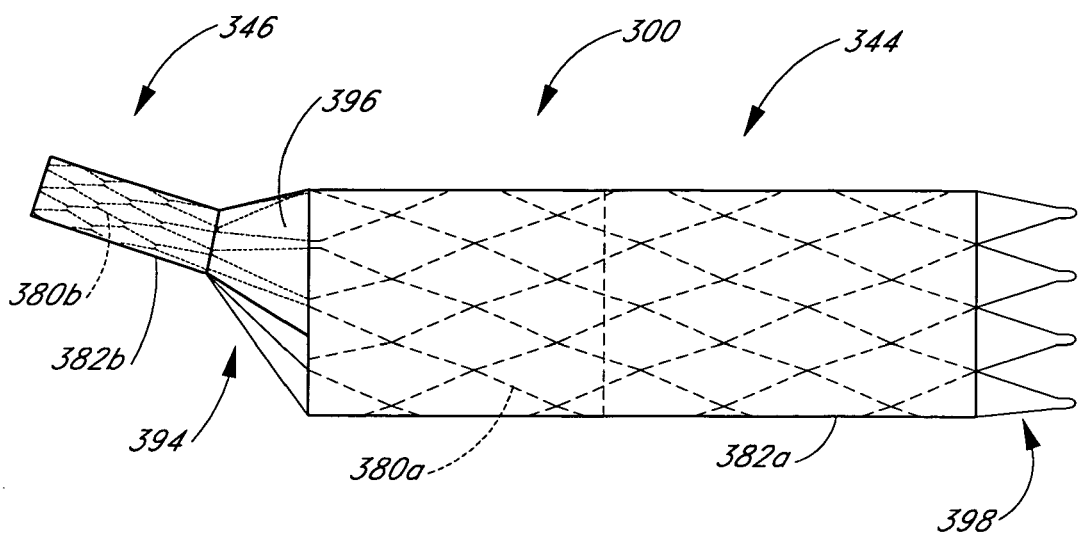
FIG. 15 is a side view of another embodiment of a vascular prosthesis.
Figure 16:
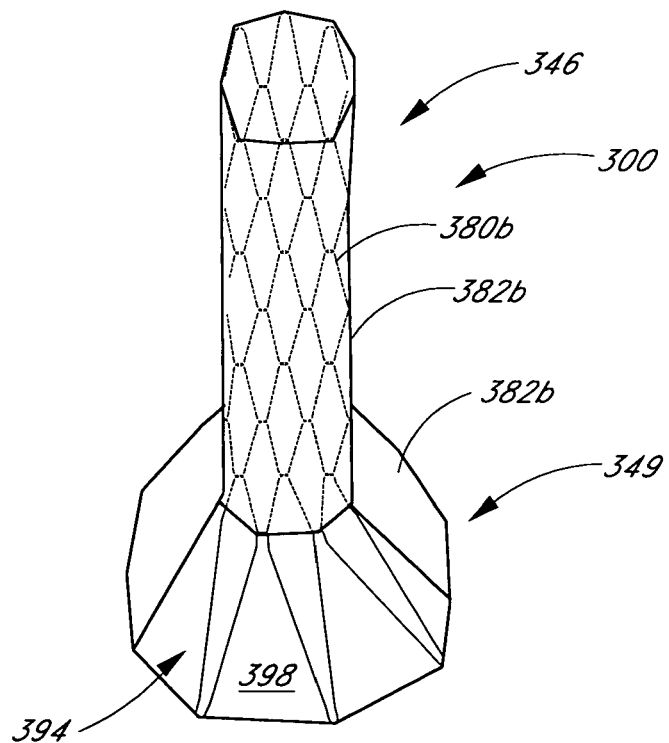
FIG. 16 is a front view of the prosthesis of FIG. 15.

FIGS. 15 and 16 are side and front views, respectively, of another modified embodiment of vascular graft 300. In these figures, like elements to those shown in FIGS. 2A-2D are designated with like reference numerals, preceded by the numeral "3". As with the previous embodiment, the vascular graft 300 generally comprises a first or main body 344 and a second or branch body 346, which are coupled together by an articulating joint 366. The bodies 344, 346 may comprise a tubular support or skeleton 380*a*, 380*b* and a polymeric or fabric sleeve 382*a*, 382*b* as described above.

In this embodiment, the articulating joint 366 is formed by connecting the tubular supports 380*a*, 380*b* of the main and branch bodies 344, 346. In this manner, a portion 394 of the tubular support extends between and connects the bodies 344, 346. In one embodiment, the bodies 344, 346 from a single body support or skeleton that comprise the main and branch bodies 344, 346 and the connection portion 394 extending therebetween.

The connection portion 394 is preferably be configured to allow articulation of the branch body 346 with respect to the main body 344 as described above. As with the previous embodiment, a portion 396 of the tubular sleeve may also extend between the main and branch bodies 344, 366. As shown in FIG. 16, a distal opening 398 remains in the sleeve to allow flow into the main branch 344 and exposing a portion of the connecting portion 394. As with the previous embodiment, this embodiment may be particularly advantageous for aneurysms positioned near, at and/or within a branch vessel to the thoracic aorta 10. In such applications, the connection portion 392 may extend across the aneurysm thereby isolating the aneurysm.

With continued reference to FIGS. 15 and 16, in the illustrated arrangement, a portion 398 of the tubular skeleton 380*a* of the main body 344 extends distally beyond the end of the sleeve 382*a* to provide an additional proximal anchoring mechanism for the main body 344 as described above.

As mentioned above, with reference to FIG. 12, in certain embodiments, the prosthesis 42 described above may be used to isolate an aneurysm 24 in the ascending aorta 14. FIGS. 17A-22 illustrate one embodiment of a deployment device 400 and a method for deploying the prosthesis 42 within the ascending aorta 14.

Figure 17A:
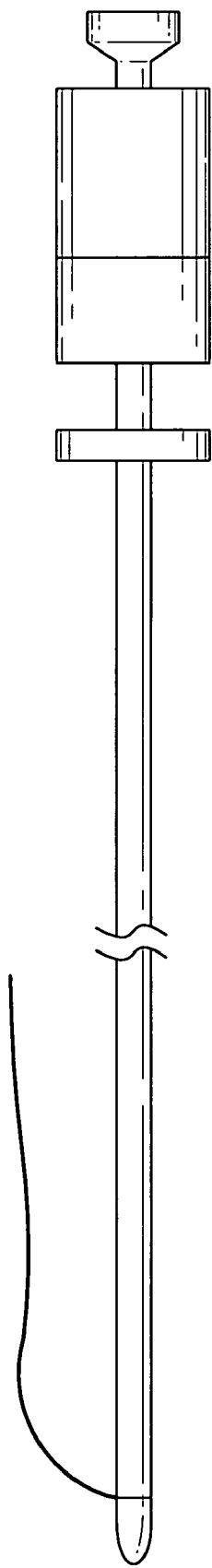
FIG. 17A is a side view of another embodiment of a deployment apparatus comprising an outer sheath, an intermediate member and an inner core.

With initial reference to FIGS. 17A-D, the deployment device 400 for placing a prosthesis in the ascending aorta 14 generally comprises an elongate flexible multi-component tubular body 402 comprising an outer sheath 404, an intermediate member 403, and an inner core 406. As will be explained below, the intermediate member 403 and the core 406 are preferably axially movably positioned within outer sheath 402. With reference to FIG. 17A, the outer sheath 402 may be provided with a proximal hub 408.

Figure 17B:
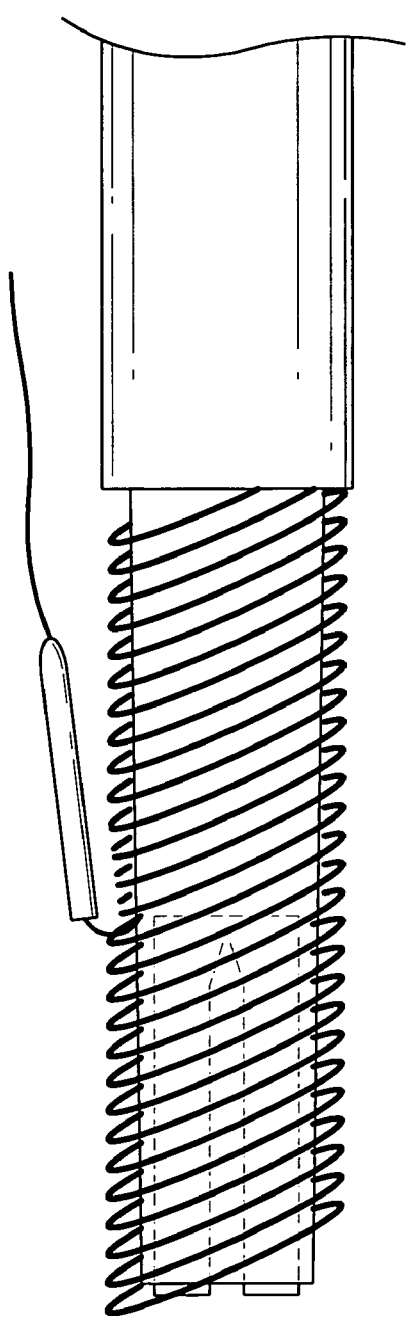
FIG. 17B is a side view of the deployment device of FIG. 17A with the outer sheath proximally retracted.
Figure 17C:
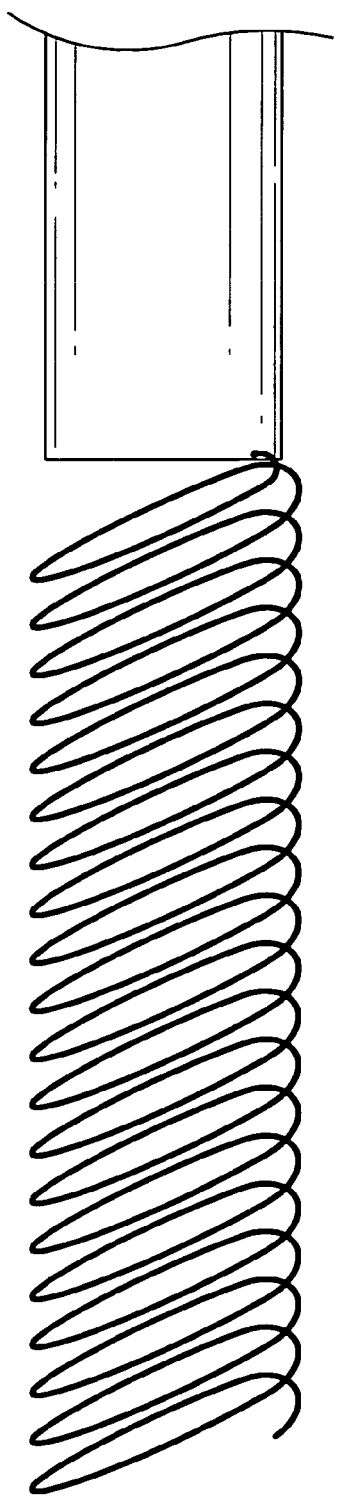
FIG. 17C is a side view of the distal end of the intermediate member.
Figure 17D:
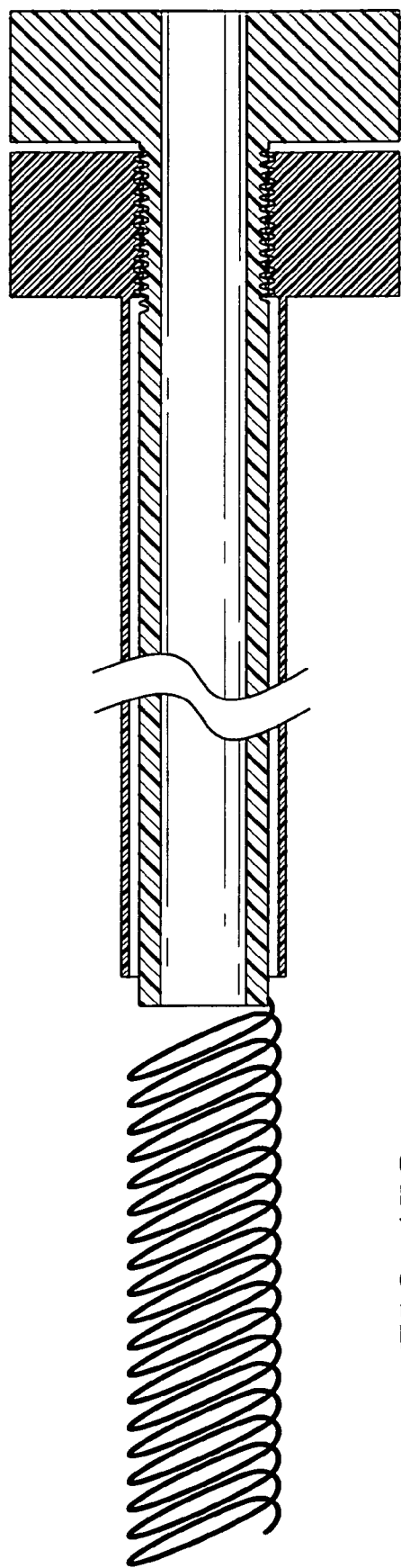
FIG. 17D is a cross-sectional side view of the proximal end of the deployment device of FIG. 17A.

With reference to FIGS. 17C-D, the intermediate member 403 comprises an inner member 410, which is axially and preferably also rotationally moveably positioned within an outer member 412. Both members 410, 412 extend from a distal end of the outer sheath 404 to the proximal end of the outer sheath 404 and terminate at proximal hubs 414, 416. As mentioned above, the inner member 410 is preferably able to rotate with respect to the outer member 412. Preferably, the apparatus 400 includes a mechanism for limiting and/or controlling the rotational movement between the two members 410, 412. As shown in FIG. 17D, in the illustrated embodiment, this mechanism comprises corresponding threads 420*a*, 420*b* positioned on the proximal portions of the inner member 410 and outer member 412 respectively. Of course in modified embodiments, other mechanisms may be used, such as, for example, corresponding grooves or protrusions.

The inner core 406 extends through the inner member 410. The inner core 406 defines a guide wire lumen (not shown) that extends through the inner core 406 from its distal end to proximal end. The proximal end of the inner core 406 may include a hub 424. As seen in FIG. 17B, the distal end of the inner core 406 forms a nose cone or cap 426. As shown in FIG. 17A, the distal end of the outer sheath 404 may abut against the nose cone 426 to provide the deployment device 400 with a tapered or smooth distal end.

With reference now to FIG. 17C, the distal end of the inner member 410 includes a helical coil 428. The helical coil 428 may be formed from any of a variety of materials including a metallic wire. As explained below, the helical coil 428 is configured to restrain the main branch 44 in a reduced profile configuration while providing an opening through which the joint 66 between the main body 44 and branch body 46 may extend. In the illustrated embodiment, this opening is defined by the spaces between the coils of the helical coil 428. With reference to FIG. 17B, the distal end of the outer member 412 advantageously extend through the coil 428. In this manner, the outer member 412 lies between the main body 44 and the coil 428 and minimizes the chances that the main body 44 is snagged or entrapped by the coil 428 during deployment. In modified embodiments, the deployment apparatus 400 may be used without the outer member 412. The distal end of the outer member 412 includes one or more openings or slits 430 through which the joint 66 may extend. As explained below, the slits 430 also allow the distal end of the outer member 412 to expand as the coil 428 is retracted and the main body 44 expands to its unconstrained diameter.

FIG. 17B shows the distal end of the deployment device 400 with the outer sheath 402 retracted to expose the distal end of the inner and outer members 410, 412. As shown, the main body 44 is constrained with in the coil 428. The linkage 66 extends through the gaps 530 in the outer member 412 and between the coil 428. The branch body 46, in turn, is constrained within a tubular sheath 434. The sheath 434 is attached to a pull wire 436, which is used to remove the sheath 434 as explained below. When the outer member 404 is not retracted, the branch body 46 lies within the sheath 434 between the coil 428 and the outer sheath 404. In other embodiments, the coil 428 may be replaced with constraining member having any of a variety of slots and openings which constrain the main body 44 while providing an opening for the linkage 66 to move through as the outer member 410 is retracted to release the main body 44.

The sheath 434 is generally configured such that as the pull wire 436 is proximally withdrawn the branch body 46 is released and can expand from a compressed state within the sheath 434. Those of skill in the art will recognize that the sheath 434 can have a variety of configurations given the goal of releasing the branch body 46 in response to proximal retraction of the pull wire 436. For example, in one embodiment, the sheath 434 has a generally tubular, sock-like configuration. In certain embodiments, the sheath 434 can have tear-lines to facilitate removal of the sheath 434 from the branch body 46.

Figure 18:
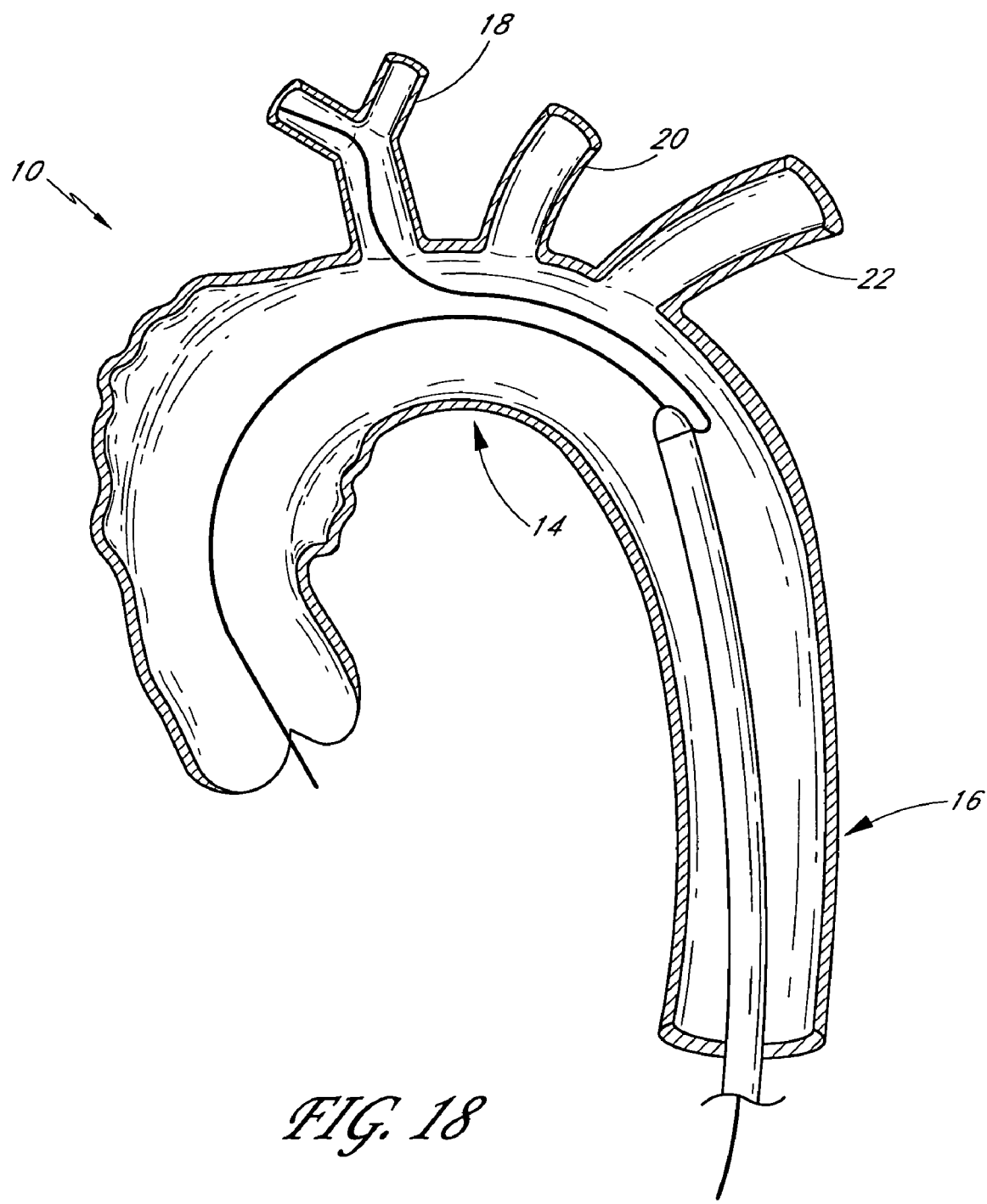
FIG. 18 is a schematic representation of a guide wire and deployment apparatus positioned across an aneurysm positioned in the ascending aorta.

A technique for deploying the prosthesis 42 using the deployment apparatus 400 described above for treating an aneurysm 24 in the ascending aorta 12 will now be described with reference to FIGS. 18-22. In a preferred embodiment, access to the right brachial and left common femoral arteries is provided through the use of insertion sheaths (not shown) as is well know in the art. A guide wire (not shown) is inserted from the right brachial through the left femoral artery. A guiding catheter may then be inserted through the right brachial over the guide wire to the left femoral. After the guiding catheter is in place, the guide wire may be removed. A second guide wire 440 is inserted through the formal access sight and into the aorta 10 until its distal end is positioned in the ascending aorta just above the aortic valve. The pull wire 436 of the deployment apparatus may then be introduced into the guiding catheter until it emerges from the right brachial. In this manner, pull wire 436 may be positioned into the right subclavian artery 18B as shown FIG. 18. The guiding catheter may then be removed and the deployment device 400 may be advanced over the second guide wire 440 into the aorta 10 as shown in FIG. 18.

Figure 19:
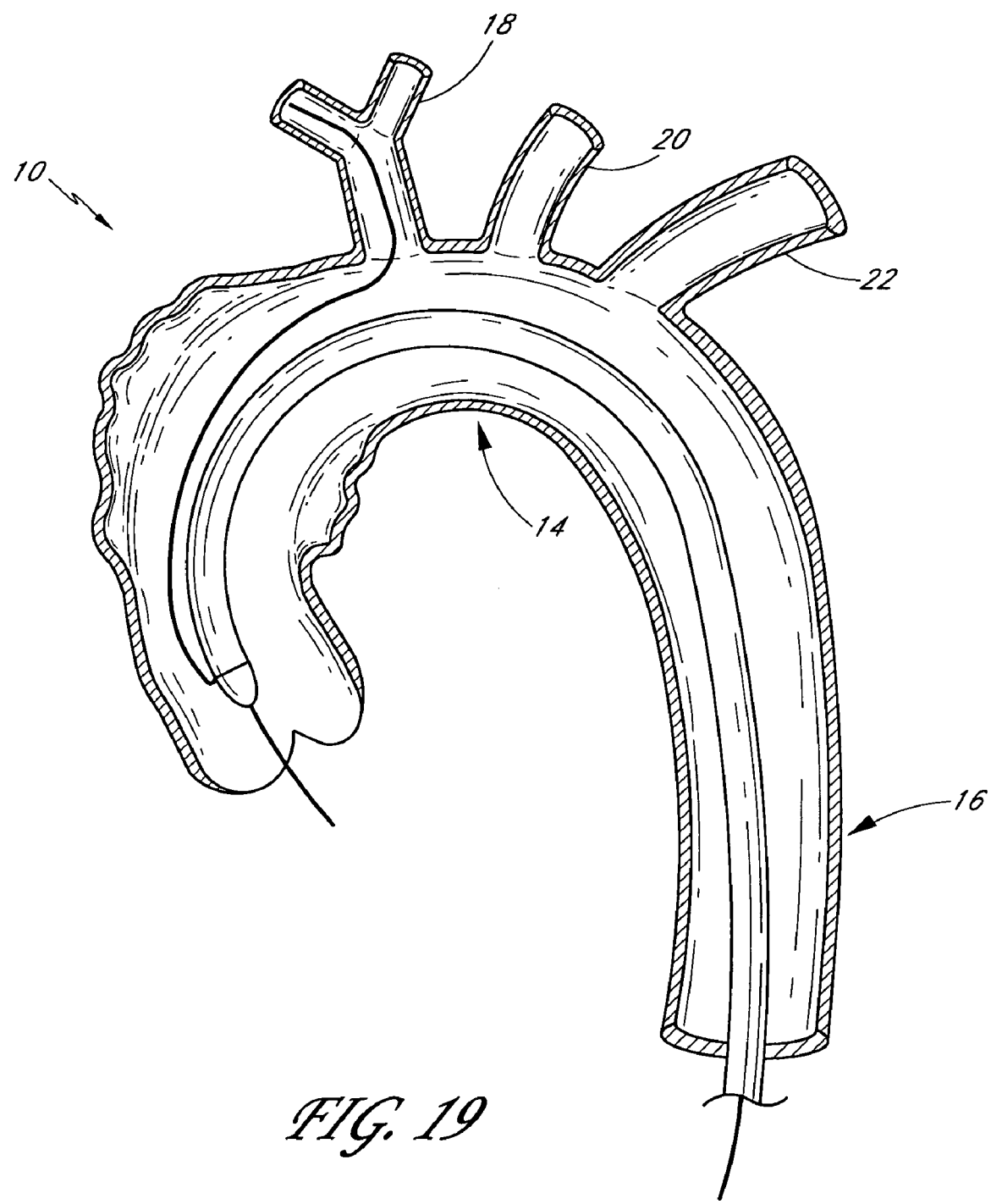
FIG. 19 is a schematic representation as in FIG. 18 the deployment apparatus positioned across the aneurysm.
Figure 20:
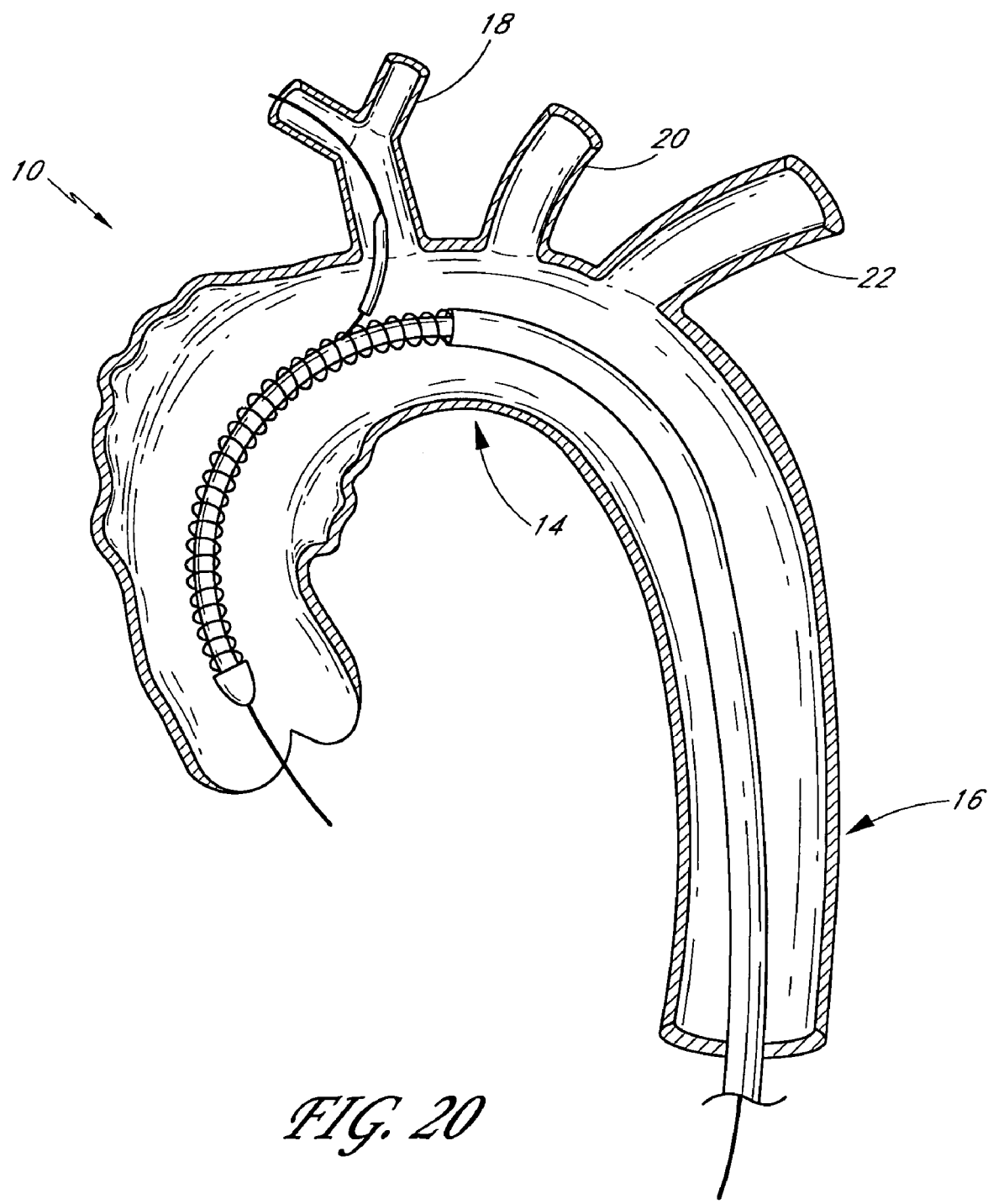
FIG. 20 is a schematic representation as in FIG. 19 with the outer sheath of the deployment apparatus retracted and a branch portion of the prosthesis positioned within the innominate artery.

With reference to FIG. 19, the deployment device 400 is advanced over the guide wire 440 until the distal end of the device is just above the aortic valve. The outer sheath 404 is then retracted to expose the coil 428 and release the branch body 46 constrained within the sheath 435. The pull wire 436 and the apparatus 400 may be adjusted to position the branch body 46 properly within the innomate artery 18. In a modified embodiment, the outer sheath 404 is retracted before the device 400 is advanced into the descending aorta 12.

Figure 21:
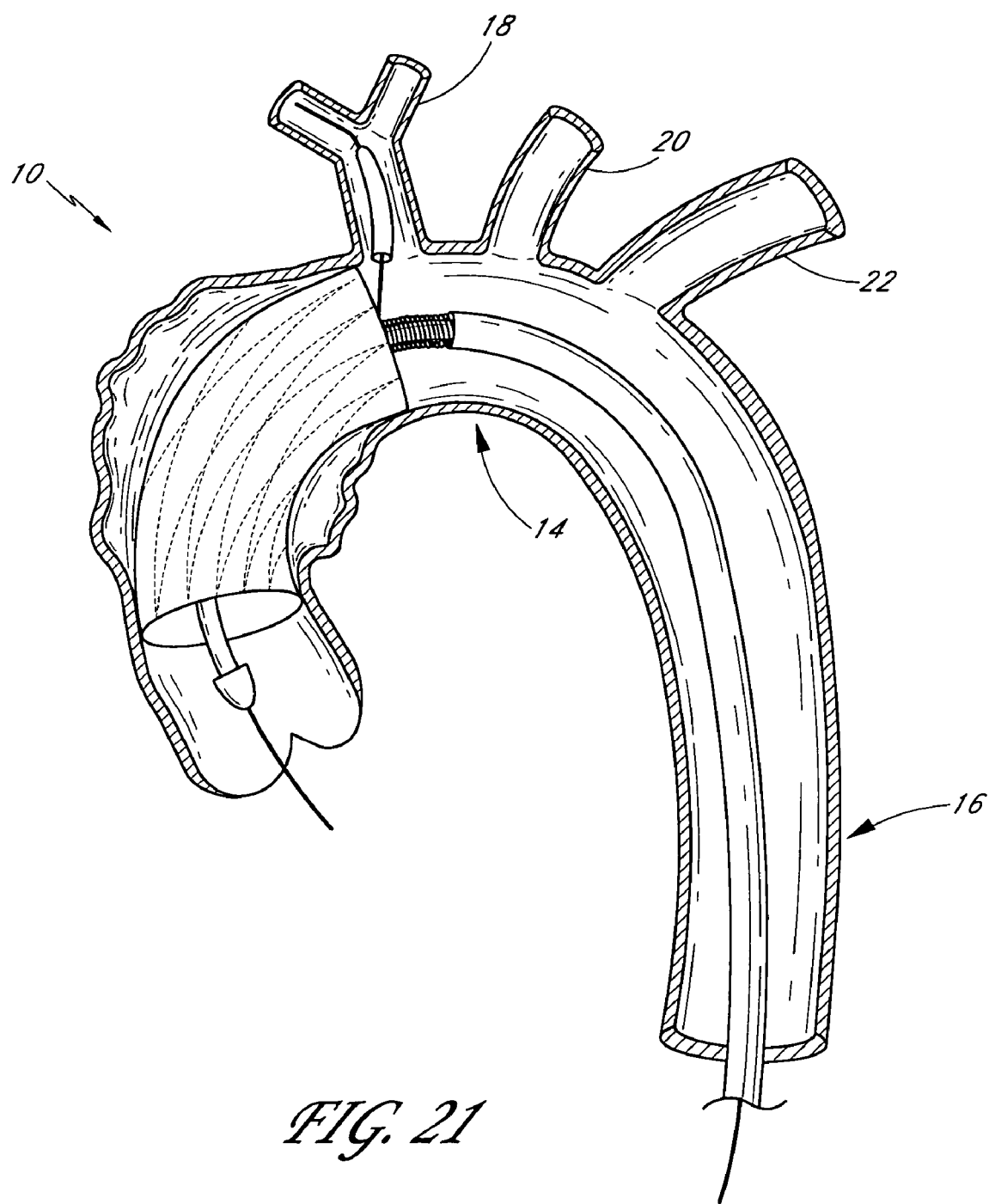
FIG. 21 is a schematic representation as in FIG. 20 with a main portion of the prosthesis deployed in the ascending aorta.
Figure 22:
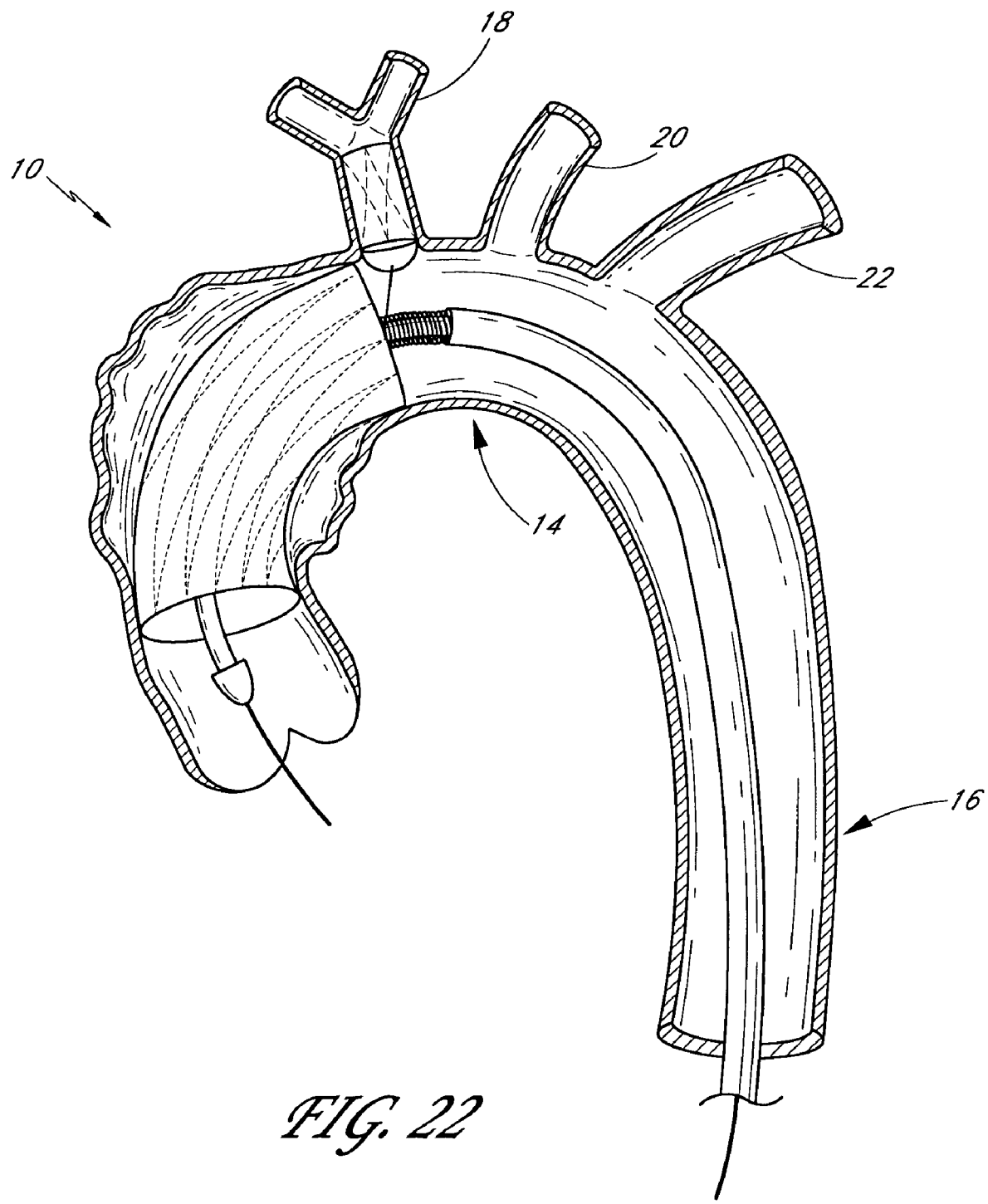
FIG. 22 is a schematic representation as in FIG. 21 with a branch portion of prosthesis deployed within the innominate artery

With the branch body 46 and main body 44 in the desired location, the inner member 410 is rotated with respect to the outer member 412. This causes the coil 428 to unscrew proximally as the linkage 66 moves through the spaces between the coils and the distal end of the coil 428 retracts to expose the distal end of the branch body as shown in FIG. 21. The inner member 410 is preferably rotated until the coil 428 has retracted sufficiently to fully deploy the main body 44 as shown in FIG. 21. With the main body 44 deployed, the pull wire 436 may be withdrawn to pull the sheath of the branch body 46 deploying the branch body 46 within the innomate artery 18. The distal end of the deployment apparatus 400 may then be withdrawn through the deployed prosthesis 42 and withdrawn from the patient.

In modified embodiments, several features of the above described method and apparatus for deploying the prosthesis 42 in the ascending aorta 12 may be modified. For example, one or more of the procedures described above may be omitted or rearranged. In addition, the apparatus 400 may be modified. For example, as mentioned above, the coil 428 may be replaced with a tubular member comprising slots through which the linkage 66 may extend. The tubular member may then be withdrawn while the proximal end of main branch is held in place by a pusher. In this manner, the main branch 44 may be pushed out of the tubular member to deploy the main branch body 44.

Another embodiment of a delivery system 500 for placing a prosthesis 42, which can be configured as described above, in the ascending aorta 14 will now be described with reference to FIGS. 23A-F. With initial reference FIG. 23A, the delivery system 500 includes a main sheath 501, a delivery sheath 502 and a pusher 504, which can be connected to a flexible nose cone 506. The main sheath 501, the delivery sheath 502 and the pusher 504 are preferably configured such that the pusher 504 can be axially moved within the lumen of delivery sheath 502. The delivery sheath 502, in turn, is configured such that it can be axially moved in the lumen of main sheath 501.

Figures 23A, 23B:
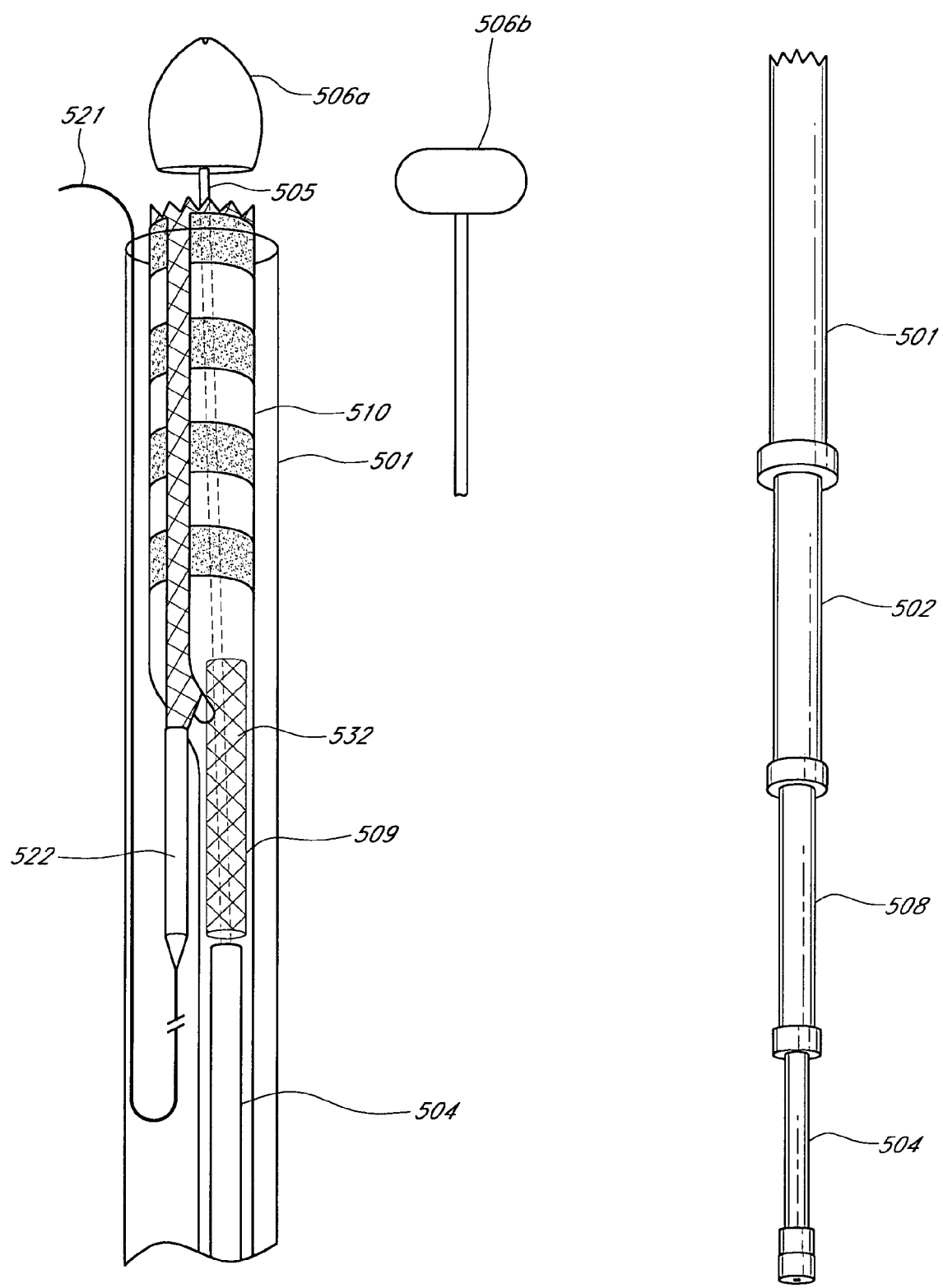
FIG. 23A is a side view of another embodiment of a deployment apparatus comprising an outer sheath, a delivery sheath having a groove extending along its longitudinal axis, and a pusher.
FIG. 23B is a side view of a proximal end of a deployment device further including a third sheath positioned between the delivery sheath and the pusher.

The pusher 504 includes an elongate tubular member 505 that can extend from the distal end of the pusher 50 through the lumens of the delivery sheath 502 and the main sheath 501 as shown in FIG. 23A. The tubular member 505 can define, at least in part, a guidewire lumen 503 that extends through the length of the delivery system 500 such that the system 500 can be advanced over a guidewire. As further shown in FIG. 23C, the nose cone 506 can be coupled to the elongate tubular member 505 at the distal end of the main sheath 501. The guidewire passageway 503 preferably also extends through the nose cone 506. The nose cone 506 can have any of a variety of shapes, such as, for example a conical shape 506a as shown in FIG. 23A or a blunt shape 506b as also shown in FIG. 23A.

Figure 23C:
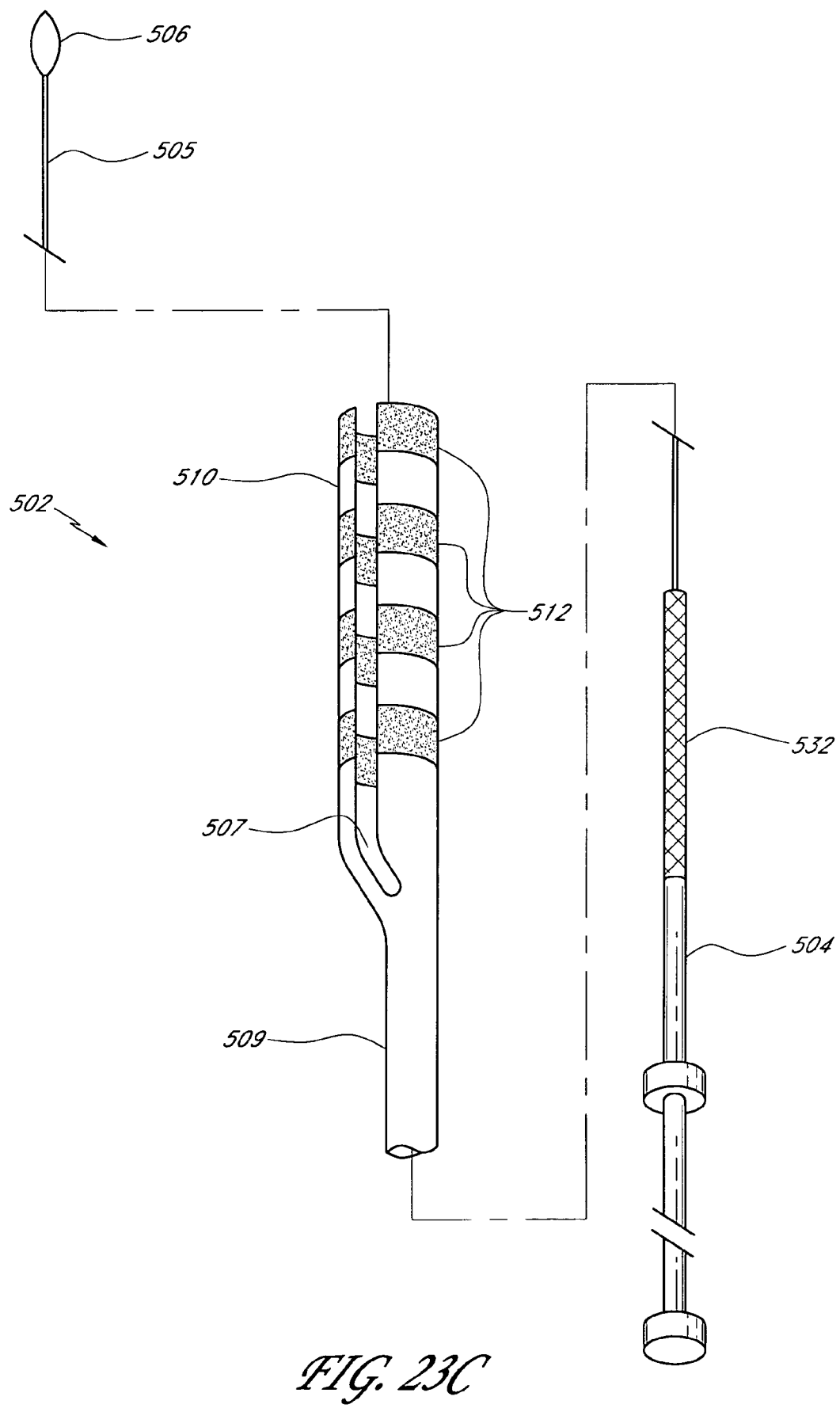
FIG. 23C is an expanded side view of the distal end of the delivery sheath and the pusher to be threaded through the delivery sheath

In one embodiment, the main sheath 501 is generally less flexible (or stiffer) than the delivery sheath 502. With reference to FIG. 23C, the delivery sheath 502 can include a groove 507 that extends longitudinally along a distal section 510 of the delivery sheath 502. The groove 507 can include an open end 511 at the distal end of the delivery sheath 502. As will be explained below, the groove 507 can be generally configured to allow the joint 66 between the branch body 46 and the main body 44 to pass as the delivery sheath 502 is retracted to release the main body 44.

The delivery sheath 502 can include a tapered portion 509 at its proximal end. The tapered portion 509 can have a smaller diameter than the diameter of the distal section 510. As shown in FIG. 23A, the tapered portion 509 advantageously provides additional space in the main sheath 501 for the branch body 46, which is enclosed in a branch sheath 522. The branch body 46 can be positioned in the main sheath 501 generally adjacent to the tapered portion 509. This arrangement advantageously reduces the radial diameter of the distal portion of the system 500. In modified embodiments, the tapered portion 509 can be eliminated.

The sheath 522 is coupled to a pull wire 521 and is generally configured such that as the pull wire 521 proximally withdrawn the branch body 46 is released and can expand from compressed state within the sheath 522. Those of skill in the art will recognize that the sheath 522 can have a variety of configurations given the goal of releasing the branch body 46 as the pull wire 521 is proximally retracted. For example, in one embodiment, the sheath 522 has a generally tubular, sock-like configuration. In certain embodiments, the sheath 522 can have tear-lines to facilitate removal of the sheath 522 from the branch body 46.

With continued reference to FIGS. 23A and 23C, the distal section 510 can be configured to store the main body 44 of the graft 42 in a compressed state during delivery. In certain embodiments, the graft 42 can be provided with a caudal or proximal portion 532 (see FIGS. 27 and 28) that can extend proximally beyond the joint 66 between the branch body 46 and the main body 44. In such an embodiment, the caudal portion 532 can be stored in a compressed configuration in the lumen of the tapered portion 509. Thus, the tapered portion 509 can have differing diameters, depending upon the size of the caudal portion of the graft 42, and the amount of annular space desired between the delivery sheath 501 and the main sheath 501 to store the branch body 46 of the graft 520.

FIG. 23B illustrates a proximal portion of a modified embodiment of the delivery system 500 in which the system 500 can include a third lumen 508 that is moveably positioned in the lumen of the delivery sheath 502. The third lumen 508 can be located between the delivery sheath 502 and the pusher 504. In such an embodiment, the caudal portion 532 of the graft 42 can be stored in a compressed state in the lumen of the third sheath 508, which is positioned within the tapered portion 509 of the delivery sheath 502.

Figures 23D, 23E:
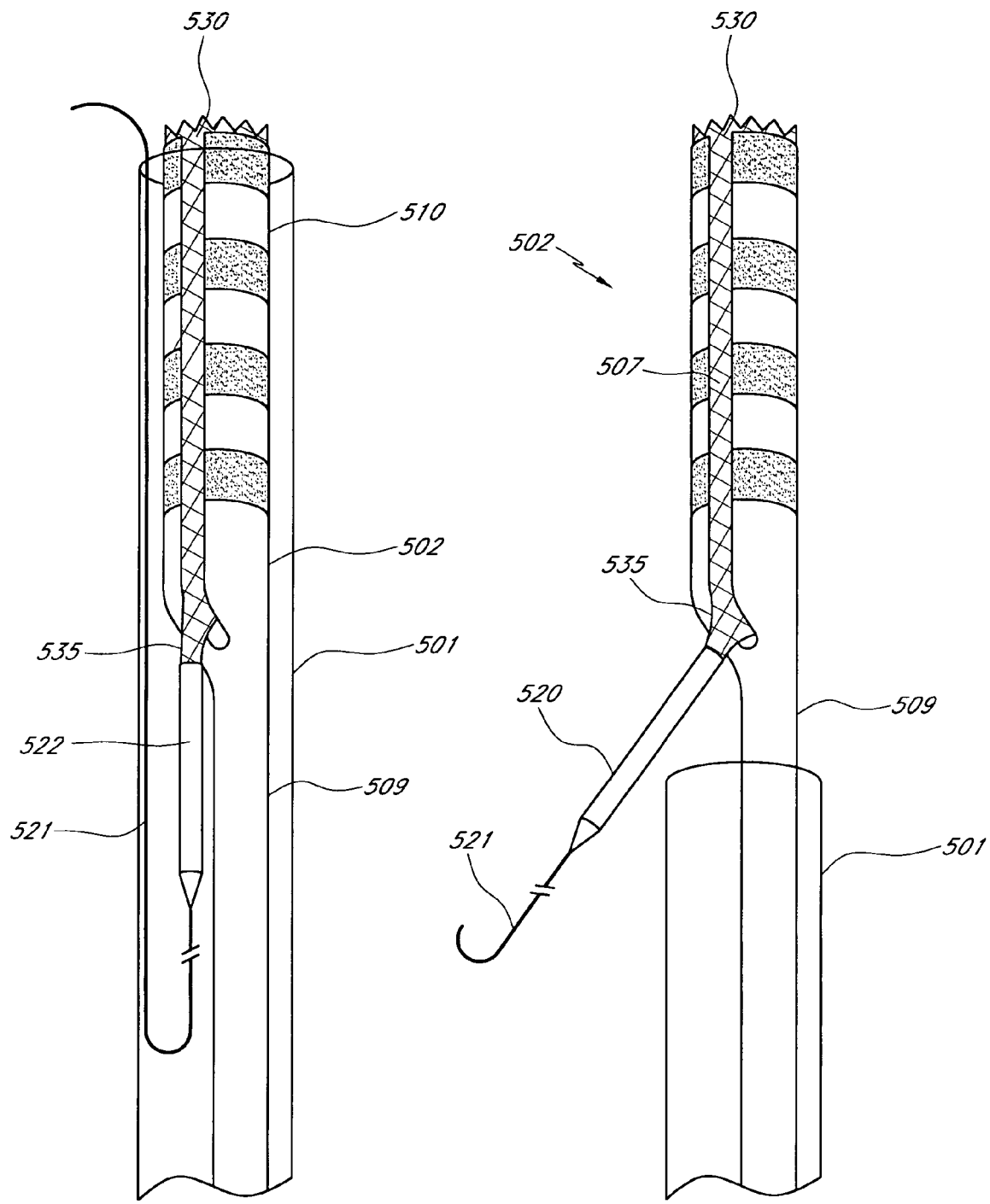
FIG. 23D is side view of the distal end of the deployment device, containing a branch delivery sheath prior to delivery.
FIG. 23E is side view of the distal end of the deployment device containing a branch delivery sheath with the main sheath retracted.
Figure 23F:
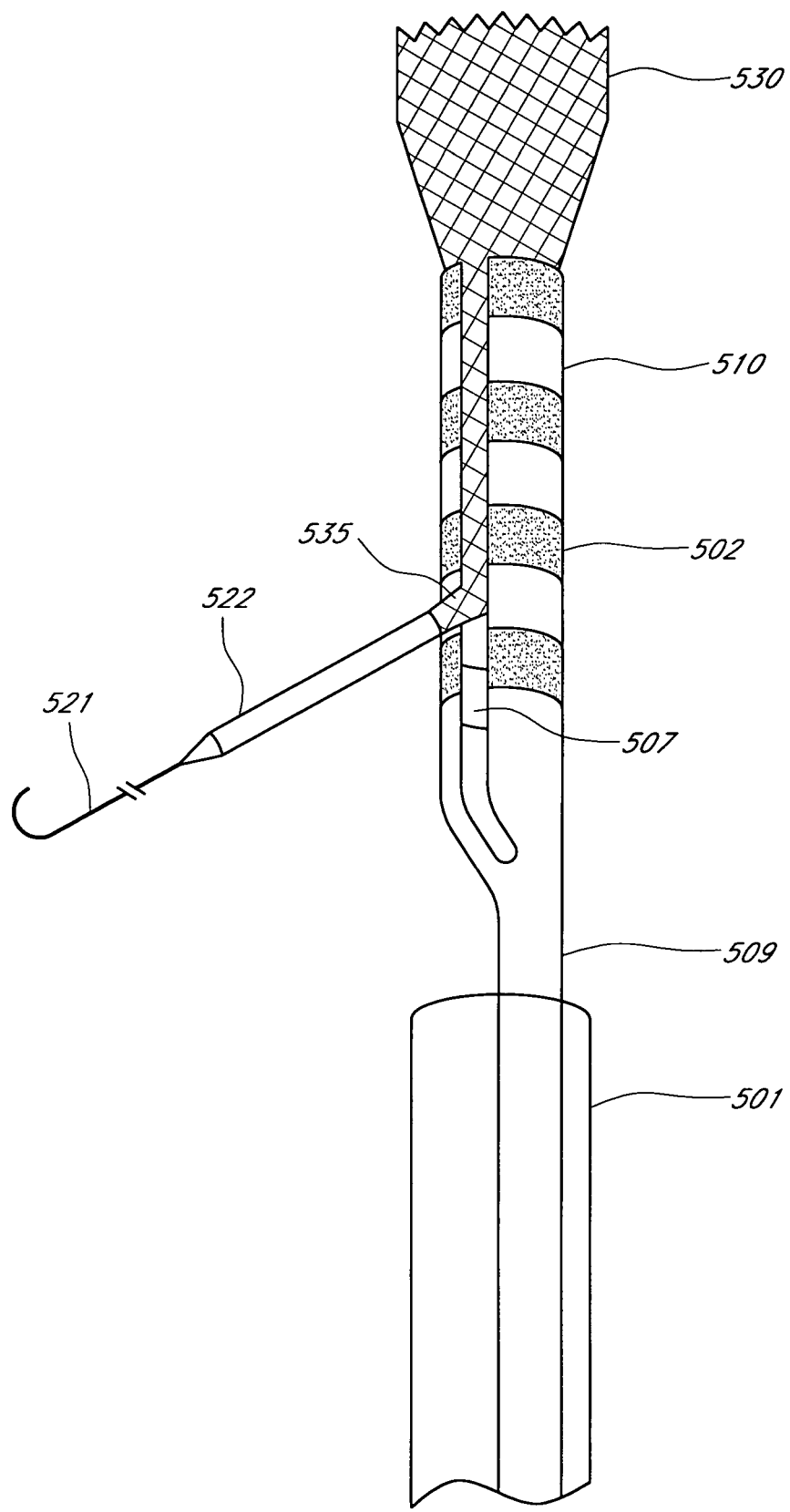
FIG. 23F is side view of the distal end of the deployment device containing a branch delivery sheath with the main sheath retracted and the main graft partially deployed.

FIGS. 23D-F depict the branch body 46 positioned within the branch delivery sheath 522. In FIG. 23D, the main sheath 501 is covering the delivery sheath 502 and the branch delivery sheath 522 is stored generally adjacent to the tapered portion 509 of the delivery sheath 502. The branch delivery sheath 522 can include a branch wire or pull wire 521 that extends from a proximal end of the branch delivery sheath 522. As will be explained below, the branch guide wire 521 can be used to position the branch delivery sheath 522 within a branch vessel of the aorta. As shown in FIG. 23D, prior to delivery, the branch wire or pull wire 521 can extend through the annular space between the delivery sheath 502 and the main sheath 501 and out the lumen of the main sheath 501 so that it may be placed in a branch vessel during initial positioning of the delivery system.

FIG. 23E shows the main sheath 501 in a retracted position. As will be explained in more detail below, in this position, the branch delivery sheath 522 can be released from its stowed position and can be positioned in the branch vessel by using traction on the branch guide wire 521. The distal end of branch body 46 is connected to the main body 44 via a joint 66 as previously described. With reference to FIG. 23F, when the delivery sheath 502 is retracted to deploy the main graft portion 530, the joint 66 can pass unobstructed through the groove 507 in the delivery sheath 502. With a self-expanding (or partially self-expanding) prosthesis 42, this configuration allows the main body 44 to be deployed as the delivery sheath 502 is retracted.

In certain embodiments, as depicted in FIGS. 23A, C-F, the distal portion 510 of delivery sheath 502 can include a plurality of segmented constricting clips or reinforced portions 512 extending along the longitudinal axis of the delivery sheath 502. In the illustrated embodiment, the constricting clips 512 can extend longitudinally along the most of the distal region 510 of the delivery sheath 502 and end at the tapered portion 509. These clips 512 can have a variable diameter to conform to the shape of the delivery sheath 502. Each clip 512 can have an opening that generally corresponds to the groove 507. The clips 512 advantageously function to contain the main portion of the graft 530 in a compressed state within the delivery sheath 502. Since the radial strength of the delivery sheath 502 can be weakened or reduced due to the presence groove 507, the clips 512 serve as skeleton that reinforces the delivery sheath 502. In addition, the extra support of the segmented constricting clips 512 enables the delivery sheath 502 to be made of very thin material and/or a particularly flexible material. Thus, the segmented positioning of the constricting clips 512 alternating with flexible portions of the delivery sheath 502 advantageously form a very flexible distal end 510 of delivery sheath 502. This facilitates navigating the distal end 510 through the aortic arch. The clips 512 can comprise additional elements coupled to the distal end 510. For example, the clips 512 can comprise metallic or polymeric c-shaped elements placed over the delivery sheath 502. In other embodiments, the clips 512 are formed by thinning or removing material on the sheath 502. In still another embodiment, the clips 512 are formed by adding material to the sheath 502. In yet another embodiment, the sheath 502 is formed without the clips.

A technique for deploying the prosthesis 42 using the delivery system 500 described above will now be described with reference to FIGS. 24-28. Initially, a guide wire (not shown) can be inserted from the right brachial artery through the left femoral artery (not shown) as is well known in the prior art. A guiding catheter (not shown) can then be inserted from the right brachial over the guide wire to the left femoral. After the guiding catheter is in place, the guide wire may be removed. A main guidewire 540 can then be inserted through the femoral access site and into the aorta 10 until its distal end is positioned generally in the ascending aorta 12 just above the aortic valve. In one embodiment, the main guidewire 540 may further include a wire mesh or "wisk-like" ventricular segment 542, depicted in FIG. 36, that is advanced through the aortic valve and positioned in the left ventricle to help stabilize the guidewire and provide better tracking during delivery of the guiding catheter and prevent a whip effect in the guidewire tip due to the pressure from the blood flow.

The branch guide wire 521 of the branch deployment apparatus may then be introduced into the guiding catheter until it emerges from the right brachial access. In this manner, the branch guidewire 521 can be positioned into the right subclavian artery 18B as shown FIG. 24. The guiding catheter may then be removed and the delivery system 500 may be advanced over the main guidewire 540. Those of skill in the art will recognize that in modified embodiments described above the branch body 46 may be positioned in the left carotid 20 and/or the subclavian 22 arteries. In such embodiments, the procedure can be modified to place the branch guide wire in the appropriate artery.

Figure 24:
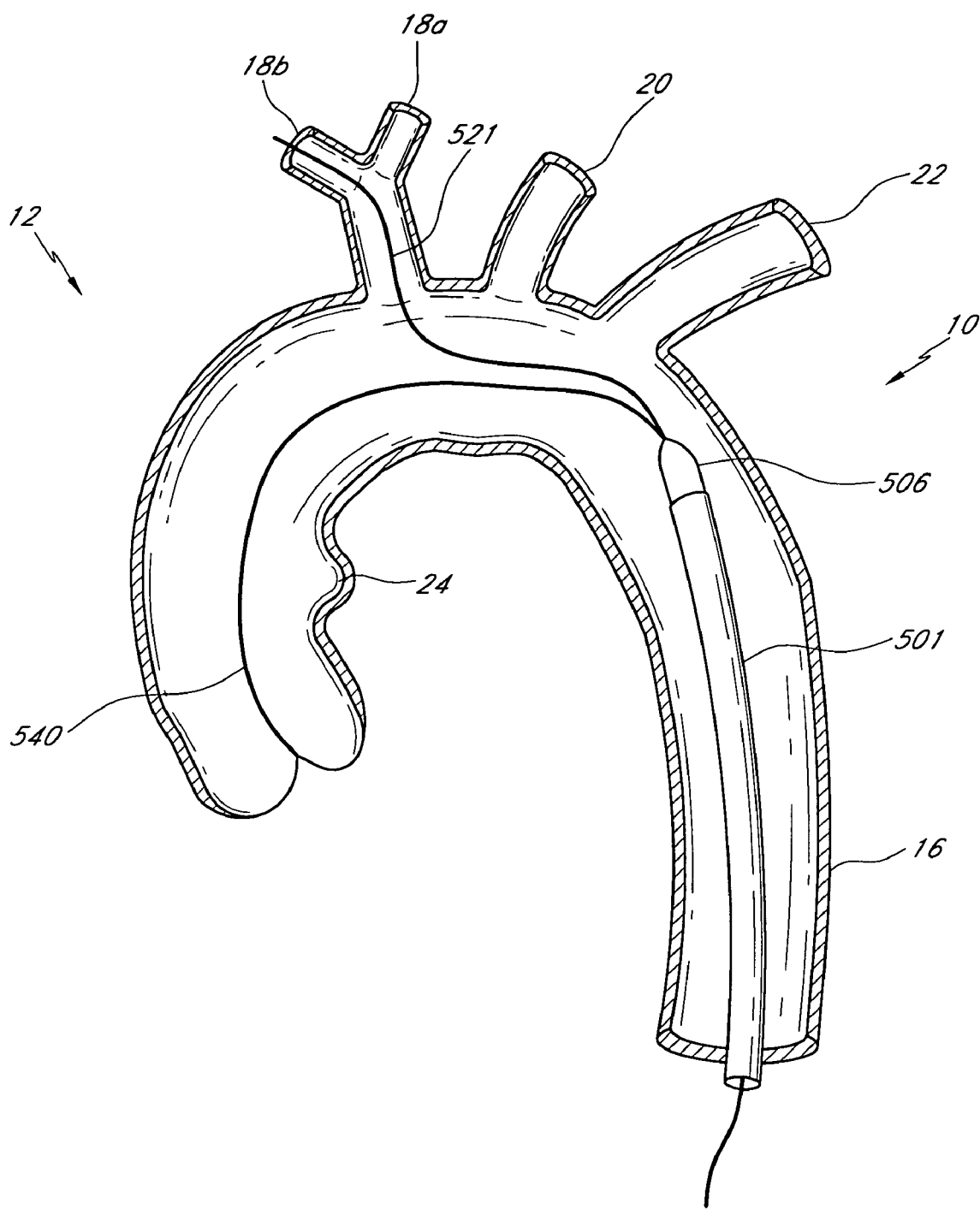
FIG. 24 is a schematic representation of a guide wire and delivery system being delivered to the ascending aorta.
Figure 25:
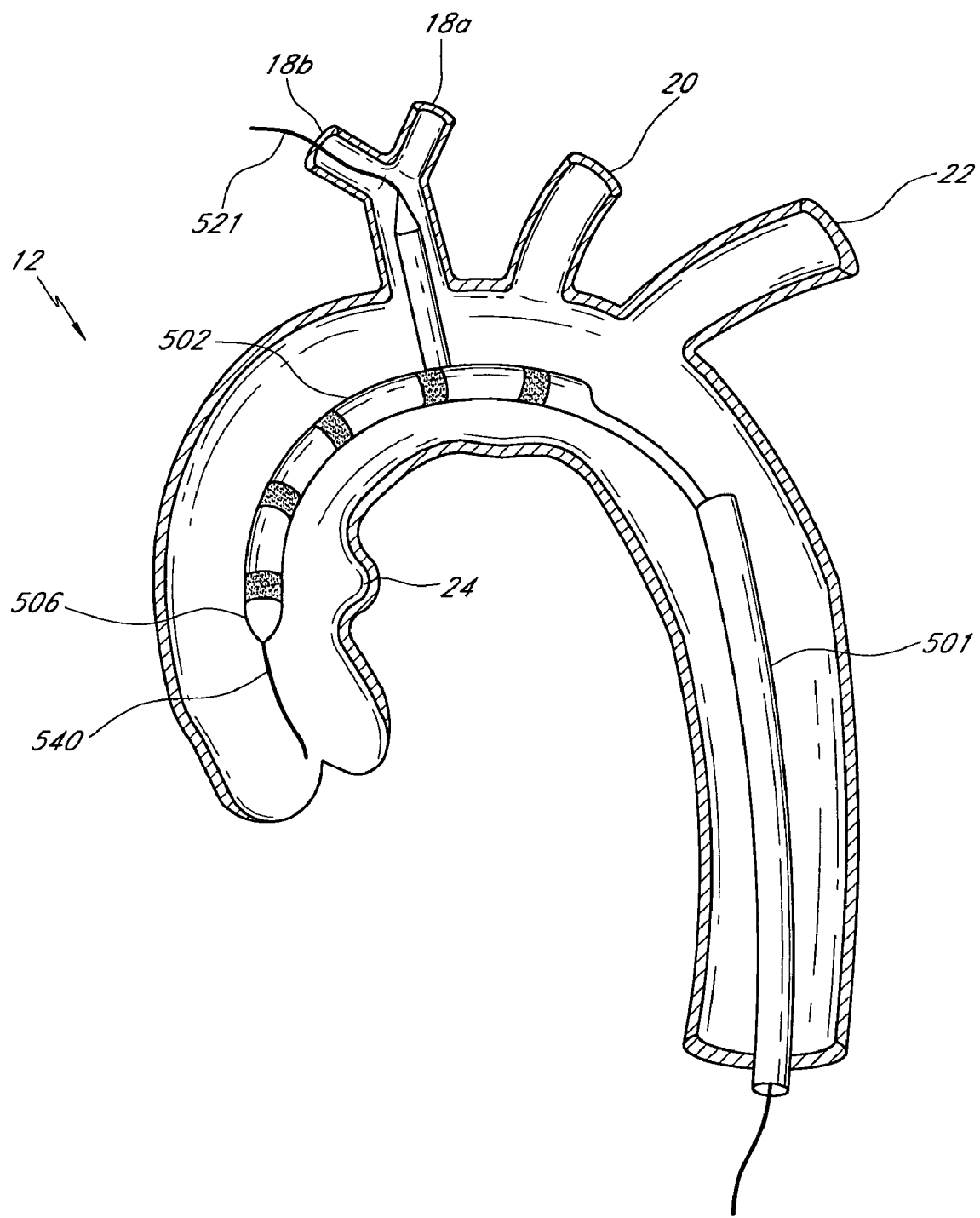
FIG. 25 is a schematic representation of a delivery system as in FIG. 23, with the main sheath of the delivery system retracted and a branch portion of the prosthesis positioned within the innominate artery.

As shown in FIG. 24, the delivery system 500 is introduced and navigated through the iliac arteries into the aorta 10 over the main guidewire 540. With reference to FIG. 25, once the delivery system 500 is at a level distal to the left subclavian artery 22, or as far as the anatomy will allow before significant curvature is required of the system 500, the main sheath 501 can be retracted to expose the delivery sheath 502, and the branch body 46 enclosed in the branch graft sheath 522. The branch sheath 522 can then be manipulated into the branch vessel 18B by retraction of the branch guidewire 521. This step removes excess wire and aids in placement of the branch body 46. Before or while the branch sheath 522 is being placed in the branch vessel 18, the delivery sheath 502 can be advanced, for example under X-ray or fluoroscopic observation, to place the distal end 510 of the delivery sheath 502 adjacent to the aneurysm 24 such that the main body 44 of the prosthesis will substantially span the length of the aneurysm 24 when deployed. In one embodiment, the clips 512 are radiopaque to aid in placement of the main body 44.

Figure 26:
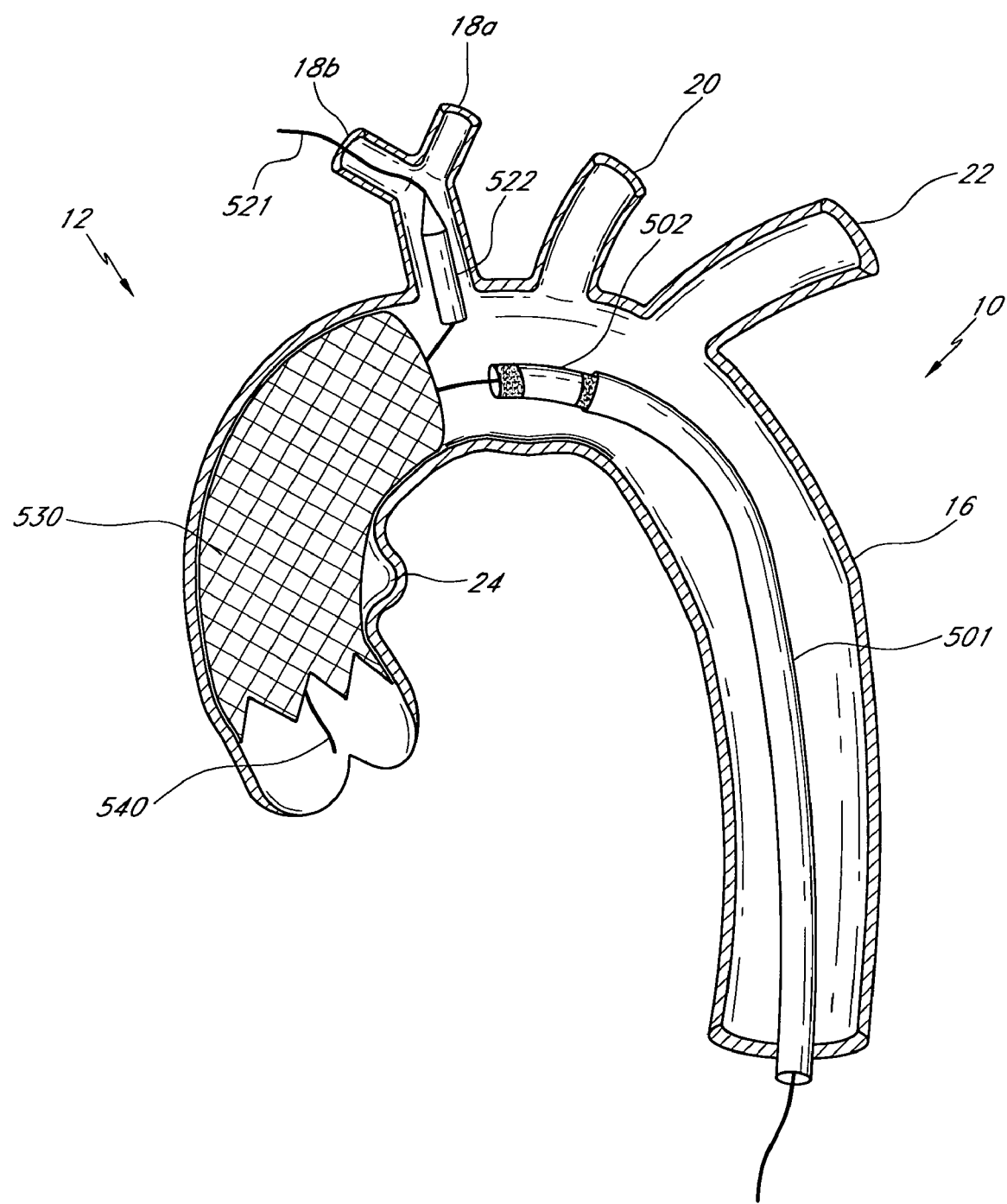
FIG. 26 is a schematic representation of a delivery system as in FIG. 23, with a main portion of the graft deployed in the ascending aorta.

With reference to FIG. 26, after satisfactory placement of the delivery sheath 502, the delivery sheath 502 can be retracted relative to the pusher 504 which holds the main body 44 in a substantially fixed longitudinal position relative to the delivery sheath 502. The delivery sheath 502 can be retracted until it reaches a position just distal to the branch graft portion 520, still enclosed in a branch sheath 522. This allow for consistent control of the system so as to minimize migration from the chosen delivery position for the graft. With reference to FIGS. 23D-F, during retraction of the delivery sheath 502, the joint 66 connecting branch body 46 to the main body 44 passes through the groove 507 in the delivery sheath 502 as it is retracted.

Once the main graft portion 530 has been deployed, the branch sheath 522 can be removed from the branch body 46 such that the branch body 46 can expand or partially expand within the branch vessel 18 with the main body 44 spanning the aneurysm 24. See e.g., FIG. 12.

Figure 27:
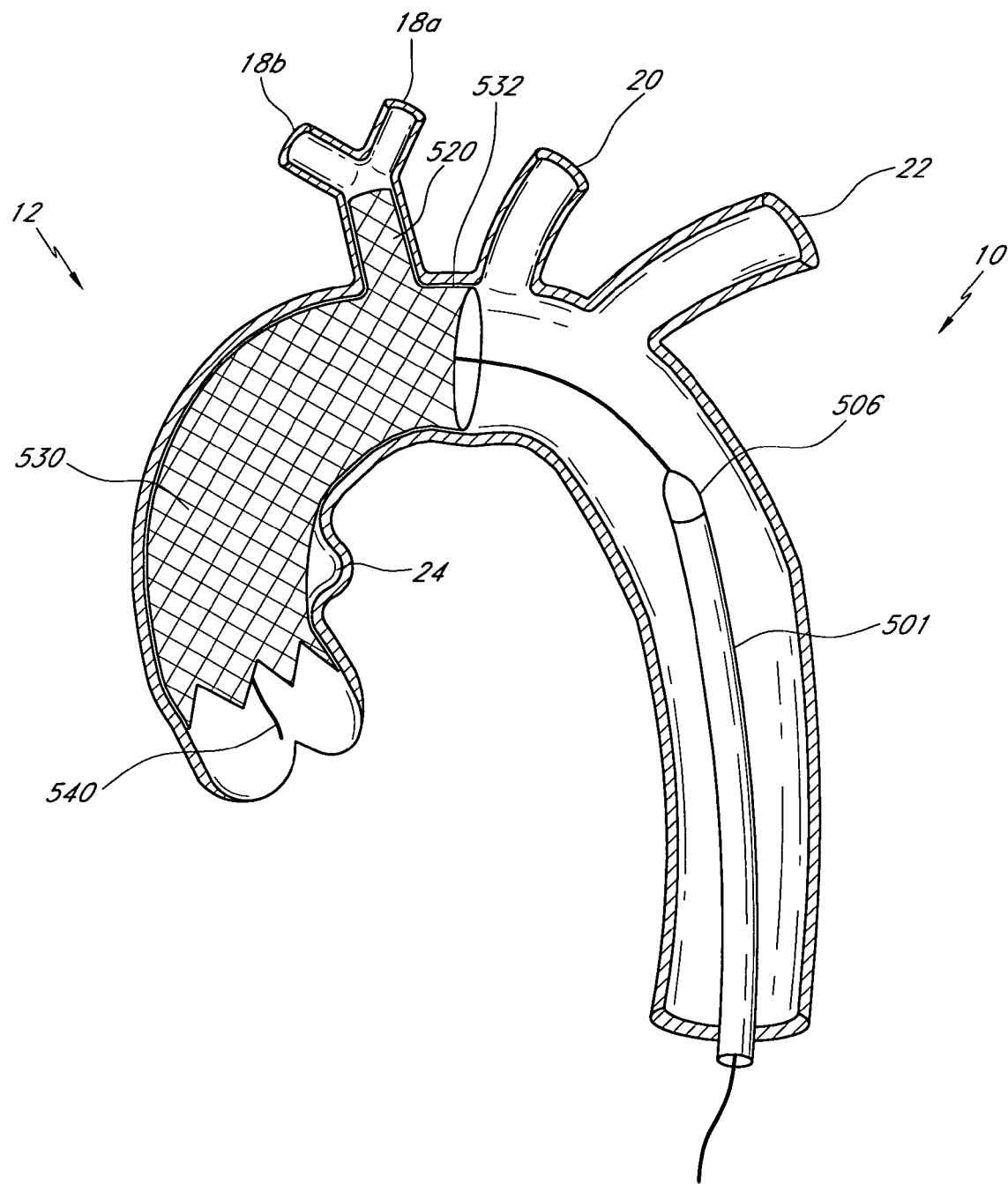
FIG. 27 is a schematic representation of a delivery system as in FIG. 23, with the branch portion of the graft deployed in the innominate artery.

As mentioned above, in certain embodiments, the prosthesis 42 can include a caudal portion 532 configured to extend proximally from the main body 44 beyond the joint 66 between the main body 44 and the branch body 46. In such embodiments, the delivery sheath 502 may be further retracted, as depicted in FIG. 27, to deploy the caudal graft portion 532, which can be stored within the tapered portion 509 of the delivery sheath 502. In a modified embodiment, the caudal graft portion 532 can be stored with a third sheath 508 (see FIG. 23B), which can be proximally retracted as depicted in FIG. 28 to release the caudal portion 532.

Figure 28:
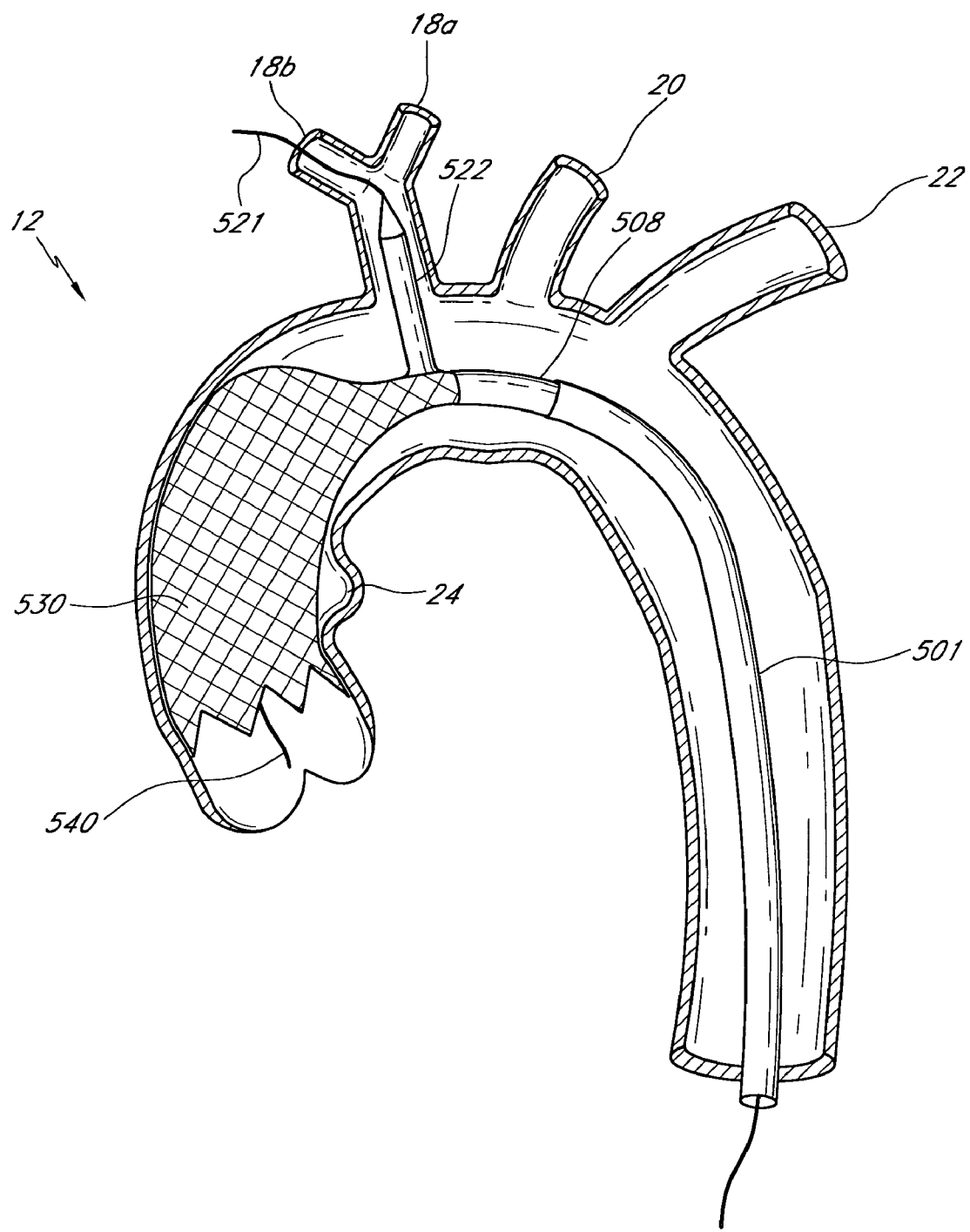
FIG. 28 is a schematic representation of an alternative delivery system comprising a third sheath containing a caudal portion of the graft.

Once the vascular graft has been fully deployed, as depicted in FIG. 27 or 28, the nose cone 506 can then retracted through the graft 42 and fully into the tip of the main sheath 501 and the system 500 can be withdrawn from the patient.

FIGS. 29-36 depict an embodiment of the branch sheath 552 that can be used in system 500 described above for restraining the branch body 46 in a compressed configuration. With reference to FIG. 29, the sheath 552 can be of variable length and diameter to accommodate varying sizes of branch body 46. The sheath 552 is operably coupled to the pull wire 551 through a hub 553 at the proximal end of the sheath 552. As further depicted in FIG. 30, the sheath can be cut longitudinally along its length on two sides so as to divide the sheath 552 generally into two halves 552a and 552b. The cut preferably dues not extend the entire length of the sheath 552, but rather terminates at a generally perpendicular slit 554 located on the proximal end of the sheath 552. Thus, the sheath halves 552a, b can remain connected, while the perpendicular slit 554 permits the sheath halves 552a, b to open in a fish mouth manner, as depicted in FIG. 31 to release a branch body 46 housed within the sheath 552. During delivery of the branch body 46 to a branch vessel, the sheath halves 552a, b can held closed, as depicted in FIG. 32, by a locking mechanism.

Figure 33:
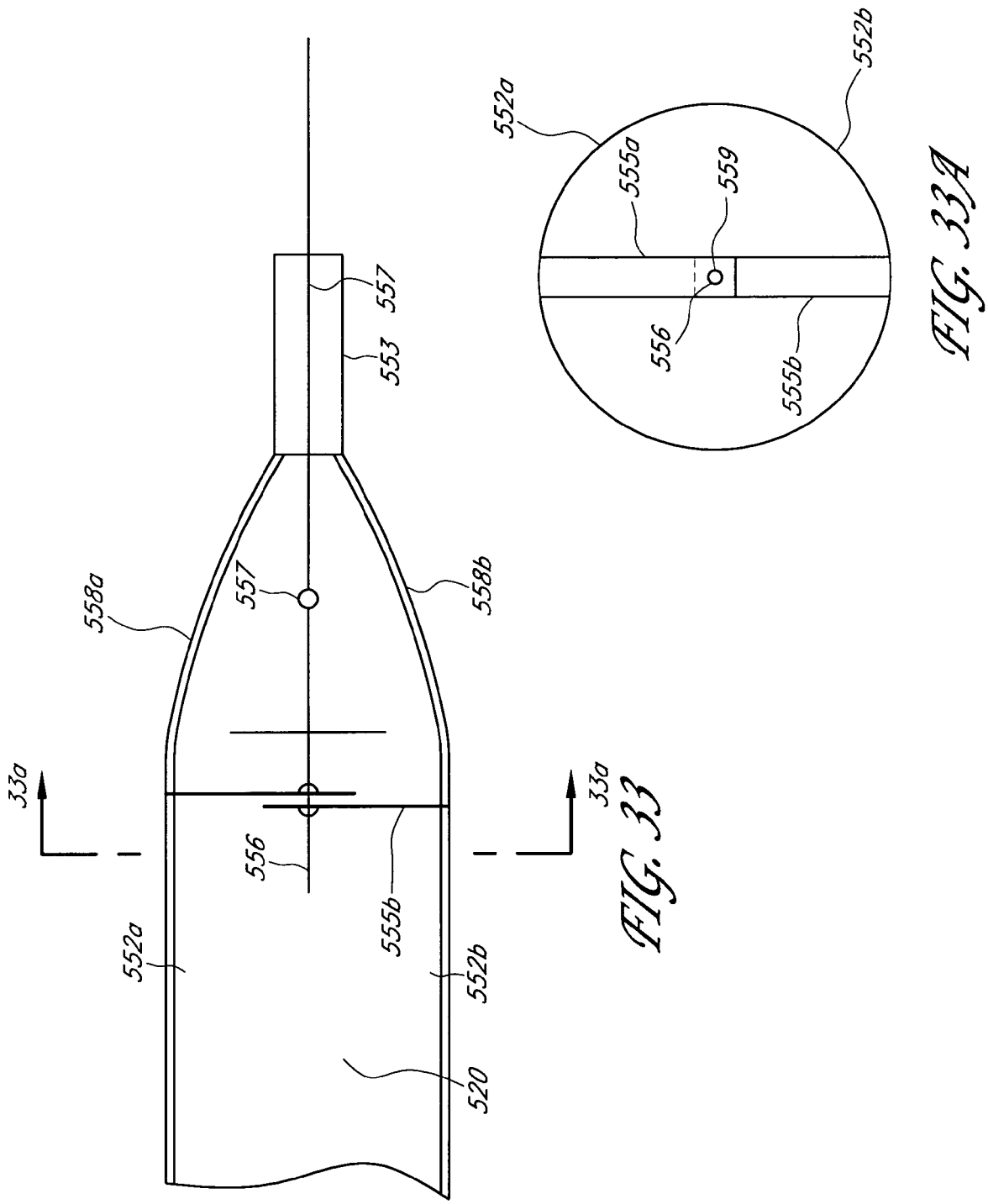
FIG. 33 is a side view of the branch graft delivery system of FIG. 29 showing the locking mechanism.
Figures 34, 34A:
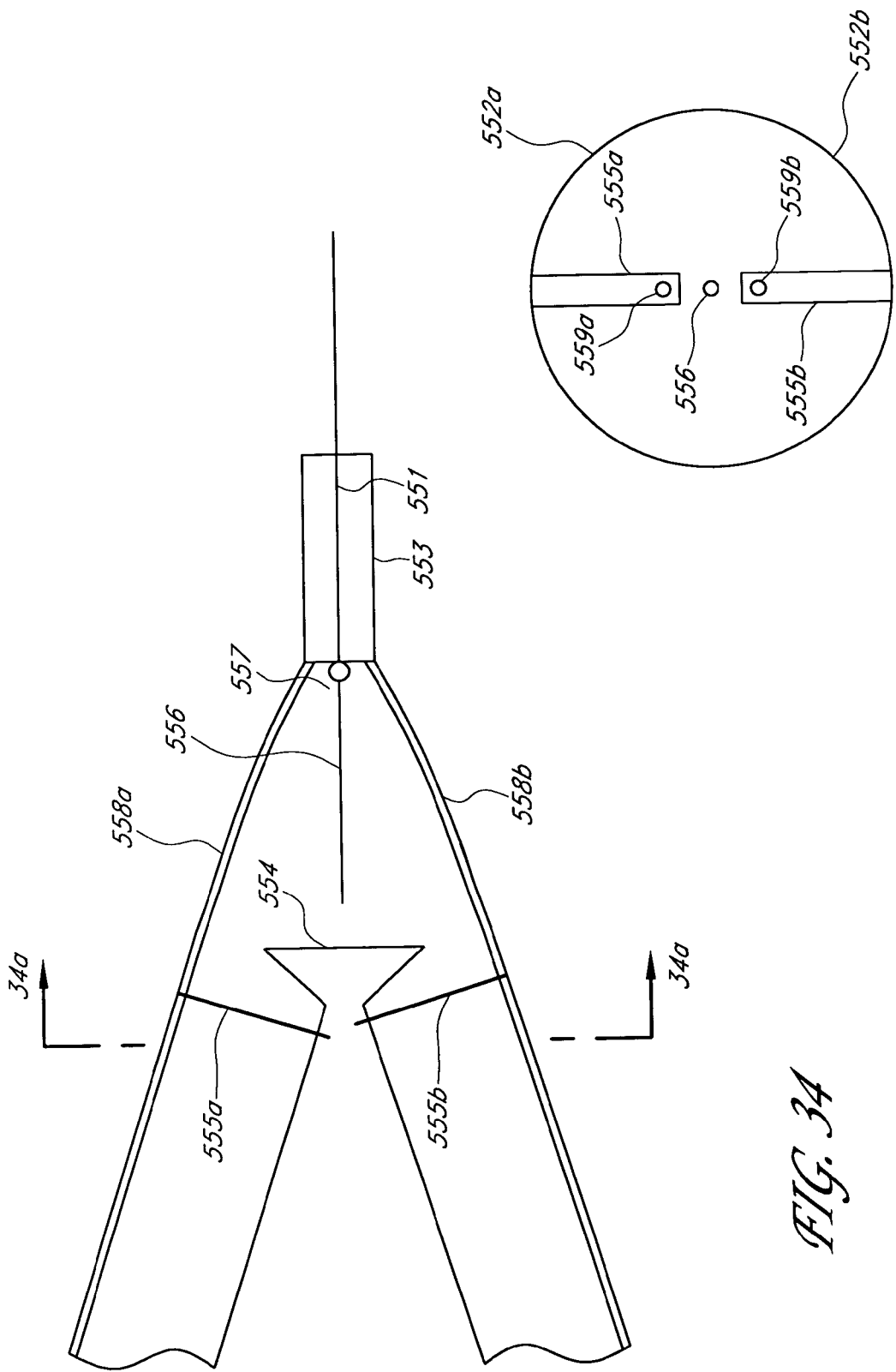
FIG. 34 is a side view of the branch graft delivery system of FIG. 29 showing the locking mechanism in an open position.
FIG. 34A a cross sectional view of the locking mechanism in an open position.

FIGS. 33-34 illustrate one embodiment of a locking mechanism 555a, b, which is couples to both sheath halves 552a, b. In the illustrated embodiment, the locking mechanism 555a, b can include planar portions 555a, 555b that are provided with holes 559a, b located A locking pin 556 is configured to be to be inserted through the holes 559a, b. As shown in FIGS. 33 and 33A, when the holes 559a, b on the locking mechanism portions 555a, b are aligned and the locking pin 556 is inserted through the locking mechanisms 555a, b, the sheath 552 held in a closed position. As shown in FIGS. 34 and 34a when the locking pin 556 is withdrawn from the holes 559a, b in the locking mechanism 555a,b, the sheath halves 552a, b will be released and open in a fish mouth manner allowing the constrained branch body (not shown) to expand.

In the illustrated embodiment shown in FIGS. 33-34, the locking pin 556 can be an extension of or coupled to the pull wire 551 used of the main delivery system 500 In this embodiment, the pull wire 551 may be threaded through the locking mechanism 555a, b to hold the sheath 552 closed during delivery. Then, when the pull wire 551 is retracted during deployment, the locking mechanism 555 will be released allowing the sheath halves 552a, b to open and permitting the branch body 46 to expand. In such an embodiment, the locking pin portion of the pull wire 551 may further comprise a retaining ball 557 coupled to the guide wire 551 at a fixed location relative to the hub 553. The retaining ball 557 prevents and/or inhibit the pull wire 551 from being pulled from the sheath hub 523 during deployment of the branch body 46 when the pull wire 551 is retracted from the locking mechanism 555 to open the sheath halves 552a, b. Thus, after deployment of the branch body 46, the sheath 552 remains connected to the pull wire 551 and thus may be withdrawn from the patient by further retraction of the pull wire 551.

Figure 35:
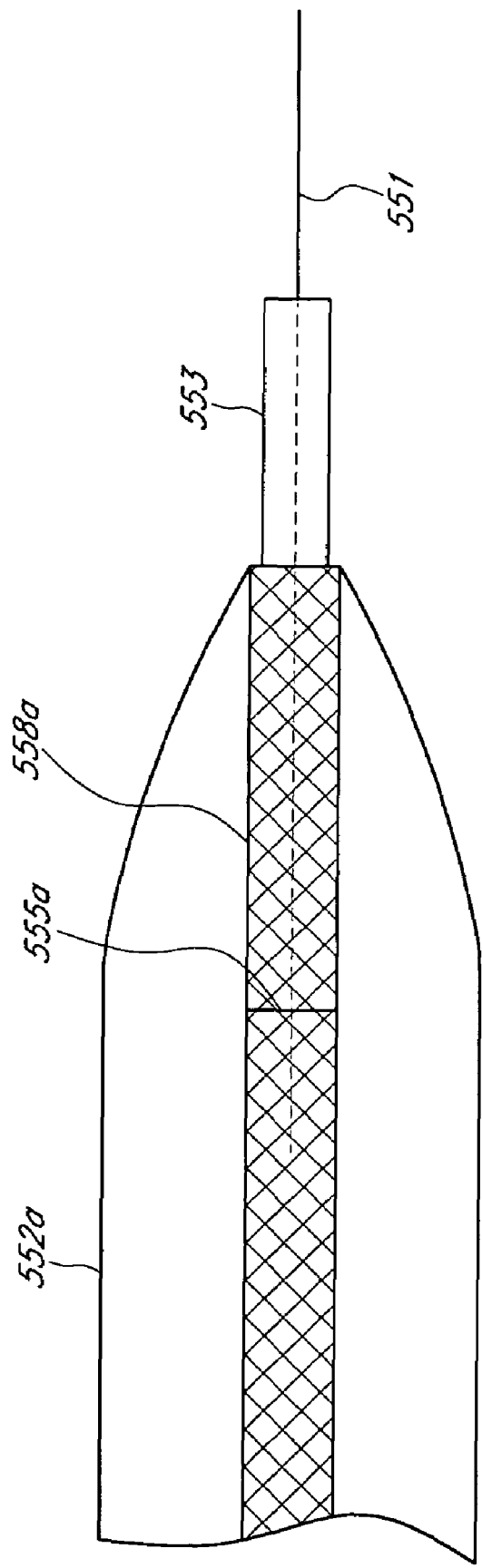
FIG. 35 is a top view of the branch graft delivery system of FIG. 29 showing the sheath support.

In the embodiments depicted in FIGS. 33, 34 and 35, the sheath halves 552a, b can also include a sheath support 558a, b that can extending from the hub 553 along the surface of the sheath 552 to the distal end of the sheath 552. The sheath support 558a, b be of variable width and length and may form a sort of exoskeleton to give support to the two sheath halves 552a, 552b, to help contain the branch body 46 in a compressed state during delivery.

In use, the branch delivery 550 may be used in conjunction with a main delivery system 500 as described above. During delivery, the branch delivery system is housed in the main lumen adjacent to the tapered portion 509 of the delivery sheath 502. Once the delivery system 500 is positioned in the aorta and the main sheath 501 retracted, the branch delivery system 550 can be released and may be positioned in a branch vessel by gentle traction. After the delivery sheath is retracted and the main graft portion 530 is deployed, the pull wire 551 may then be retracted to release the locking pin 556 and open the two halves of branch graft sheath 552a, b. In a modified embodiment, an 8FR guiding catheter may be inserted over the pull wire 551 to in providing counter traction on the pull wire 551 so as to move the locking pin 556 out of the locking mechanism 555a and b. Once the sheath halves 552a, b are opened, the branch graft 520 is released into the branch vessel, completing its delivery.

Once the branch graft has been deployed, the guide wire 551 may be further retracted to withdraw the sheath halves 552a and b, attached to the guide wire via the hub 553 and retaining ball 557, from the patient's vasculature.

Figure 36:
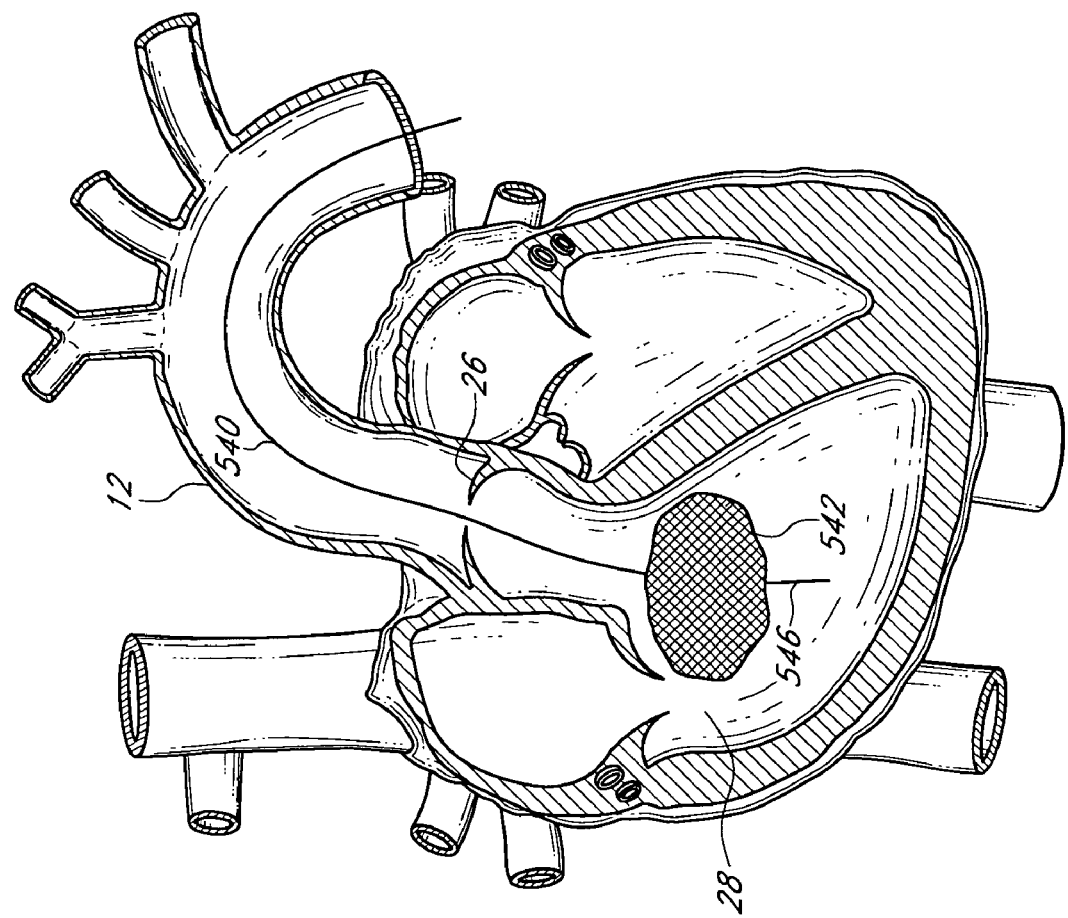
FIG. 36 is a schematic representation of a guide wire according to the present invention positioned in the descending aorta and left ventricle.

FIGS. 36-37 depict an embodiment of the main guide wire 540 that can be used in system 500 described above for delivering the branch graft deployment apparatus into the aortic arch. With reference to FIG. 37, the main guide wire 540 may preferably include a wire mesh or "wisk-like" ventricular segment 542 located in the distal region of the guide wire 540. A flexible tip 544 preferably extends distal of the ventricular segment 542 to prevent trauma to the vascular walls as the guidewire is advanced through the aorta. In use, as depicted in FIG. 36, the ventricular segment 542 of the guidewire 540 may be advanced through the aortic valve 26 and positioned in the left ventricle 28 to help stabilize the guidewire and prevent a whipping effect in the guidewire tip 544 due to the high pressure forces from the fluid flow in the aorta. This arrangement advantageously reduces the whip effect of the guidewire tip 544 which would irritate the ventricle and subsequently produce arrhythmias. In addition, this arrangement provides improved stability of the guidewire, thus allowing better tracking during delivery of the guiding catheter and preventing the possibility of a perforation of the ventricular wall. In one embodiment, the wire mesh of the ventricular segment 542 may be coated with lidocaine or any other suitable anesthetic to further reduce arrhythmias.

The apparatuses and methods described above have been described primarily with respect to thoracic aorta and aneurysms positioned therein. However, it should be appreciated that the apparatuses and methods may also be adapted for aneurysms and defects in other portions of the vascular anatomy. For example, it is anticipated that the apparatuses and methods described above may find utility in treating aneurysms or other defects in the abdominal aorta and/or its related branch vessels.

For example, it is envisioned that this system can be utilized for the delivery of a single piece endoluminal graft for the repair of an abdominal aortic aneurysm by utilizing the branch delivery technique for deployment of the contralateral limb of an aortic endoluminal graft. In such an embodiment, some diameters and lengths of the graft and deployment system will be modified to fit the natural anatomical dimensions of the vasculature in which the delivery system will be deployed.

While a number of preferred embodiments of the invention and variations thereof have been described in detail, other modifications and methods of using and medical applications for the same will be apparent to those of skill in the art. Accordingly, it should be understood that various applications, modifications, combinations, sub-combinations and substitutions may be made of equivalents without departing from the spirit of the invention or the scope of the claims.

What is claimed is:

1. A combination of a deployment apparatus and a vascular graft, the graft having a main portion and a branch portion that is connected to the main portion by an articulating joint, the combination comprising:
- a main elongate flexible member having a proximal end, a distal end, and a lumen extending therebetween;
- a second elongate member, slidably housed in the lumen of the main elongate member, having a proximal end, a distal end, a lumen extending therebetween, and a longitudinal groove located on the distal end;
- wherein the second elongate member comprises a plurality of adjacent segments along at least a portion of its length;
- wherein each of the plurality of adjacent segments lies substantially along a plane;
- wherein the plane of each adjacent segment is substantially parallel to the plane of a neighboring adjacent segment;
- wherein at least two neighboring segments of the plurality of adjacent segments are separated by a distance extending along a longitudinal axis of the second elongate member;
- wherein each of the at least two neighboring segments of the plurality of adjacent segments extends substantially along a perimeter of a cross-section of the second elongate member and is discontinuous at the longitudinal groove; and
- wherein each of the at least two neighboring segments of the plurality of adjacent segments comprises a reinforced portion that provides more radial reinforcement of the second elongate member than exists between the at least two neighboring segments of the plurality of adjacent segments, such that the main portion of the vascular graft is maintained within the lumen of the second elongate member;
- a pusher slidably housed in the lumen of the main elongate member, located proximal to the distal end of the second elongate member;
- wherein the main portion of vascular graft is positioned within the lumen of the second elongate member between the distal end of the second elongate member and the pusher;
- wherein the main portion comprises a proximal end, a distal end, and a lumen extending therebetween;
- wherein the branch portion comprises a proximal end, a distal end, and a lumen extending therebetween;
- wherein the proximal end and the distal end of the branch portion are each distinct from each of the proximal end and distal end of the main portion;
- wherein the articulating joint of the vascular graft extends, at least partially, through the longitudinal groove of the second elongate member; and
- wherein the main portion is configured such that when (a) the combination is at least partially in a main vessel, and (b) the main elongate member is retracted proximally relative to the main portion, and (c) the second elongate member is retracted proximally such that the articulating joint moves distally relative to the groove, then the main portion expands in the main vessel, such that after expansion of the main portion in the main vessel and after expansion of the branch portion in a branch vessel that branches off the main vessel, the proximal and distal ends of the main portion reside entirely within the main vessel while the proximal and distal ends of the branch portion reside entirely within the branch vessel.

2. The combination of claim 1, wherein a proximal region of the second elongate member is tapered such that a cross-sectional width of a proximal region of the second elongate member is less that a cross-sectional width of a distal region of the second elongate member.

3. The combination of claim 2, wherein the branch portion of the vascular graft is positioned in the lumen of the main elongate member, adjacent to the tapered proximal region of the second elongate member.

4. The combination of claim 2, wherein each of the reinforced portions is disposed along a region of the second elongate member extending from the distal end of the second elongate member to the tapered proximal region.

5. The combination of claim 4, wherein the reinforced portions are open along the longitudinal groove.

6. The combination of claim 5, wherein the main portion of the vascular graft further comprises a caudal graft extending beyond the articulating joint, wherein the caudal graft portion is housed in a compressed state in the tapered region of the lumen of the second elongate member between the main portion of the vascular graft and the pusher.

7. The combination of claim 1, wherein the pusher comprises proximal and distal ends, having a flexible tip located at the distal end, and having a lumen extending between the proximal and distal ends.

8. The combination of claim 1, further comprising a third elongate member having a distal and a proximal end and a lumen extending therebetween, wherein the third elongate member is slidably housed in the lumen of the main elongate member proximal to the second elongate member, and wherein the pusher is slidably housed in the lumen of the third elongate member.

9. The combination of claim 1, wherein the main portion of the vascular graft further comprises a caudal graft extending beyond the articulating joint connecting the branch portion, wherein the caudal graft portion is housed in a compressed state in the lumen of the third elongate member between the main portion of the vascular graft and the pusher.

10. The combination of claim 1, wherein, when the main portion is located in a thoracic aorta, the branch portion is positionable in a branch vessel of the thoracic aorta.

11. The combination of claim 1, further comprising:
- a elongate flexible member having a proximal end, a distal end, and a lumen extending therebetween;
- a protuberance positioned at the distal end of the elongate flexible member; and
- wherein, during deployment of the vascular graft, the elongate flexible member extends within the lumen of the first elongate member, such that the protuberance extends beyond the distal end of the first elongate member.

12. The combination of claim 11, wherein the protuberance comprises an open framework.

13. The combination of claim 11, wherein the protuberance is coated with an anesthetic.

14. The combination of claim 1, further comprising a guidewire assembly, comprising:
- a guidewire; and
- means for limiting lateral motion of a distal end of the guidewire relative to a longitudinal axis of the guide wire, when the guidewire is positioned in a lumen of a blood vessel.

15. The combination of claim 14, wherein the means for limiting lateral motion comprises a wire meshwork.

16. The combination of claim 1, further comprising a branch delivery sheath configured to maintain the branch portion of the vascular graft in a compressed state.

17. The combination of claim 16, wherein the branch delivery sheath is coupled to a pull wire that is configured to effect removal of the branch delivery sheath from the branch portion of the vascular graft.

18. The combination of claim 17, wherein the branch delivery sheath comprises first and second distal portions, coupled at a proximal portion of the sheath and separable at a distal portion of the branch delivery sheath, and wherein the branch delivery sheath is configured to surround at least partially the branch portion when the branch portion is in the compressed state.

19. The combination of claim 18, further comprising a sheath support extending along each of the first and second distal portions of the sheath.

20. The combination of claim 18, further comprising:
a locking mechanism configured to maintain the distal portions of the sheath in proximity to each other such that the branch portion is maintained in the compressed state; and
a release mechanism, configured to release the locking mechanism such that the first and second distal portions separate at the distal portion of the sheath.

21. The combination of claim 20, wherein the pull wire is coupled to the release mechanism, and wherein the pull wire is configured to effect release of the locking mechanism, such that the first and second distal portions separate at the distal portion of the sheath.

22. The combination of claim 20, wherein the locking mechanism comprises:
a hole located in a proximal portion of each of the first and second distal portions of the sheath; and
a retaining pin reversibly insertable into each hole;
wherein, when the retaining pin is inserted into each hole, the sheath maintains the branch portion of the vascular graft in the compressed state.

23. The combination of claim 16, further comprising:
a hub on a proximal end of the sheath;
a pull wire extending through the hub; and
a retaining pin coupled to the pull wire.

24. The combination of claim 23, wherein the hub further comprises a lumen, and the retaining pin comprises an extension from the pull wire that extends through the lumen of the hub.

25. The combination of claim 1, wherein the branch vessel of the thoracic aorta in which the branch portion is positionable is selected from the group consisting of a carotid artery, an innominate artery, and a subclavian artery.

26. A combination of a deployment apparatus and a vascular graft, the graft having a main portion and a branch portion that is connected to the main portion by an articulating joint, the combination comprising:
a main elongate flexible member having a proximal end, a distal end, and a lumen extending therebetween;
a second elongate member, slidably housed in the lumen of the main elongate member, having a proximal end, a distal end, a lumen extending therebetween, and a longitudinal groove located on the distal end;
wherein the second elongate member comprises a plurality of adjacent reinforcing segments along at least a portion of its length;
wherein no reinforcing segment overlaps with any other reinforcing segment;
wherein at least two neighboring segments of the plurality of reinforcing segments are separated by a distance extending along a longitudinal axis of the second elongate member;
wherein each of the at least two neighboring segments of the plurality of reinforcing segments extends substantially along a perimeter of a cross-section of the second elongate member and is discontinuous at the longitudinal groove; and
wherein each of the at least two neighboring segments of the plurality of reinforcing segments comprises a reinforced portion that provides more radial reinforcement of the second elongate member than exists between the at least two neighboring segments of the plurality of reinforcing segments, such that the main portion of the vascular graft is maintained within the lumen of the second elongate member;
a pusher slidably housed in the lumen of the main elongate member, located proximal to the distal end of the second elongate member;
wherein the main portion of vascular graft is positioned within the lumen of the second elongate member between the distal end of the second elongate member and the pusher;
wherein the main portion comprises a proximal end, a distal end, and a lumen extending therebetween;
wherein the branch portion comprises a proximal end, a distal end, and a lumen extending therebetween;
wherein the proximal end and the distal end of the branch portion are each distinct from each of the proximal end and distal end of the main portion;
wherein the articulating joint of the vascular graft extends, at least partially, through the longitudinal groove of the second elongate member; and
wherein the main portion is configured such that when (a) the combination is at least partially in a main vessel, and (b) the main elongate member is retracted proximally relative to the main portion, and (c) the second elongate member is retracted proximally such that the articulating joint moves distally relative to the groove, then the main portion expands in the main vessel, such that after expansion of the main portion in the main vessel and after expansion of the branch portion in a branch vessel that branches off the main vessel, the proximal and distal ends of the main portion reside entirely within the main vessel while the proximal and distal ends of the branch portion reside entirely within the branch vessel.

27. The combination of claim 26, wherein the branch vessel of the thoracic aorta in which the branch portion is positionable is selected from the group consisting of a carotid artery, an innominate artery, and a subclavian artery.

28. The combination of claim 26, wherein a proximal region of the second elongate member is tapered such that a cross-sectional width of a proximal region of the second elongate member is less that a cross-sectional width of a distal region of the second elongate member.

29. The combination of claim 28, wherein the branch portion of the vascular graft is positioned in the lumen of the main elongate member, adjacent to the tapered proximal region of the second elongate member.

30. The combination of 28, wherein each of the reinforced portions is disposed along a region of the second elongate member extending from the distal end of the second elongate member to the tapered proximal region.

31. The combination of claim 30, wherein the reinforced portions are open along the longitudinal groove.

32. The combination of claim 28, wherein the main portion of the vascular graft further comprises a caudal graft extending beyond the articulating joint, wherein the caudal graft portion is housed in a compressed state in the tapered region of the lumen of the second elongate member between the main portion of the vascular graft and the pusher.

33. The combination of claim 26, wherein the pusher comprises proximal and distal ends, having a flexible tip located at the distal end, and having a lumen extending between the proximal and distal ends.

34. The combination of claim 26, further comprising a third elongate member having a distal and a proximal end and a lumen extending therebetween, wherein the third elongate member is slidably housed in the lumen of the main elongate member proximal to the second elongate member, and wherein the pusher is slidably housed in the lumen of the third elongate member.

35. The combination of claim 34, wherein the main portion of the vascular graft further comprises a caudal graft extending beyond the articulating joint connecting the branch portion, wherein the caudal graft portion is housed in a compressed state in the lumen of the third elongate member between the main portion of the vascular graft and the pusher.

36. The combination of claim 26, wherein, when the main portion is located in a thoracic aorta, the branch portion is positionable in a branch vessel of the thoracic aorta.

37. The combination of claim 26, further comprising:
   a elongate flexible member having a proximal end, a distal end, and a lumen extending therebetween;
   a protuberance positioned at the distal end of the elongate flexible member; and
   wherein, during deployment of the vascular graft, the elongate flexible member extends within the lumen of the first elongate member, such that the protuberance extends beyond the distal end of the first elongate member.

38. The combination of claim 37, wherein the protuberance comprises an open framework.

39. The combination of claim 37, wherein the protuberance is coated with an anesthetic.

40. The combination of claim 26, further comprising a guidewire assembly, comprising:
   a guidewire; and
   means for limiting lateral motion of a distal end of the guidewire relative to a longitudinal axis of the guidewire, when the guidewire is positioned in a lumen of a blood vessel.

41. The combination of claim 40, wherein the means for limiting lateral motion comprises a wire meshwork.

42. The combination of claim 26, further comprising a branch delivery sheath configured to maintain the branch portion of the vascular graft in a compressed state.

43. The combination of claim 42, wherein the branch delivery sheath is coupled to a pull wire that is configured to effect removal of the branch delivery sheath from the branch portion of the vascular graft.

44. The combination of claim 43, wherein the branch delivery sheath comprises first and second distal portions, coupled at a proximal portion of the sheath and separable at a distal portion of the branch delivery sheath, and wherein the branch delivery sheath is configured to surround at least partially the branch portion when the branch portion is in the compressed state.

45. The combination of claim 44, further comprising a sheath support extending along each of the first and second distal portions of the sheath.

46. The combination of claim 44, further comprising:
   a locking mechanism configured to maintain the distal portions of the sheath in proximity to each other such that the branch portion is maintained in the compressed state; and
   a release mechanism, configured to release the locking mechanism such that the first and second distal portions separate at the distal portion of the sheath.

47. The combination of claim 46, wherein the pull wire is coupled to the release mechanism, and wherein the pull wire is configured to effect release of the locking mechanism, such that the first and second distal portions separate at the distal portion of the sheath.

48. The combination of claim 46, wherein the locking mechanism comprises:
   a hole located in a proximal portion of each of the first and second distal portions of the sheath; and
   a retaining pin reversibly insertable into each hole;
   wherein, when the retaining pin is inserted into each hole, the sheath maintains the branch portion of the vascular graft in the compressed state.

49. The combination of claim 42, further comprising:
   a hub on a proximal end of the sheath;
   a pull wire extending through the hub; and
   a retaining pin coupled to the pull wire.

50. The combination of claim 49, wherein the hub further comprises a lumen, and the retaining pin comprises an extension from the pull wire that extends through the lumen of the hub.

* * * * *

UNITED STATES PATENT AND TRADEMARK OFFICE
CERTIFICATE OF CORRECTION

PATENT NO. : 7,699,883 B2  Page 1 of 1
APPLICATION NO. : 11/337043
DATED : April 20, 2010
INVENTOR(S) : Myles Douglas et al.

It is certified that error appears in the above-identified patent and that said Letters Patent is hereby corrected as shown below:

In Column 24, Line 8: Replace "that", with --than--.

In Column 24, Line 20: Replace "5", with --2--.

Signed and Sealed this
Twenty-third Day of August, 2011

David J. Kappos
*Director of the United States Patent and Trademark Office*